(12) United States Patent
Leck et al.

(10) Patent No.: US 8,691,147 B2
(45) Date of Patent: Apr. 8, 2014

(54) APPARATUS FOR PROCESSING A SAMPLE IN A LIQUID DROPLET AND METHOD OF USING THE SAME

(75) Inventors: Kwong Joo Leck, Nanos (SG); Nam Yong Kim, Nanos (SG); Jackie Y. Ying, Nanos (SG); Li Li, Nanos (SG); Yong Yeow Lee, Nanos (SG)

(73) Assignee: Agency for Science, Technology and Research, Singapore (SG)

( * ) Notice: Subject to any disclaimer, the term of this patent is extended or adjusted under 35 U.S.C. 154(b) by 1333 days.

(21) Appl. No.: 11/984,197

(22) Filed: Nov. 14, 2007

(65) Prior Publication Data
US 2010/0285573 A1    Nov. 11, 2010

Related U.S. Application Data

(63) Continuation-in-part of application No. PCT/SG2006/000363, filed on Nov. 24, 2006.

(51) Int. Cl.
| | |
|---|---|
| *G01N 21/00* | (2006.01) |
| *G01N 1/00* | (2006.01) |
| *G01N 33/00* | (2006.01) |
| *B01L 9/00* | (2006.01) |

(52) U.S. Cl.
USPC .............................. 422/63; 422/561; 73/64.56

(58) Field of Classification Search
USPC ................... 422/500, 551, 504; 436/174, 180
See application file for complete search history.

(56) References Cited

U.S. PATENT DOCUMENTS

| | | |
|---|---|---|
| 3,754,872 A | 8/1973 | Zauft |
| 5,219,528 A | 6/1993 | Clark |
| 5,506,121 A | 4/1996 | Skerra et al. |
| 5,560,811 A | 10/1996 | Briggs et al. |

(Continued)

FOREIGN PATENT DOCUMENTS

| | | |
|---|---|---|
| DE | 10043042 C2 | 3/2000 |
| EP | 0 812 693 A1 | 12/1997 |

(Continued)

OTHER PUBLICATIONS

Luca, D., "Preparation of TiOx Thin Films by Reactive Pulsed-Laser Ablation," Journal of Optoelectronics and Advanced Materials, vol. 7, No. 2, Apr. 2005, p. 625-630.

(Continued)

*Primary Examiner* — Jill Warden
*Assistant Examiner* — Brittany Fisher
(74) *Attorney, Agent, or Firm* — Morgan, Lewis & Bockius LLP

(57) ABSTRACT

The invention provides an apparatus and a method of processing a biological and/or chemical sample in a liquid droplet. The apparatus comprises a processing compartment, which is defined by a reservoir and an immobilization member. The processing compartment is further adapted to accommodate a medium, which is immiscible with the liquid droplet, and of a lower surface energy than the liquid of the liquid droplet. The reservoir is defined by a circumferential wall and a base. The immobilization member is arranged within the reservoir and comprises a surface that is patterned in such a way that it comprises at least one predefined immobilization area. The predefined immobilization area within the patterned surface is of a higher surface energy than the medium. The liquid droplet is disposed onto the predefined immobilization area, whereby the liquid droplet is immobilized thereon via hydrophilic-hydrophilic or hydrophobic-hydrophobic interactions.

29 Claims, 34 Drawing Sheets

(56) References Cited

U.S. PATENT DOCUMENTS

| | | | |
|---|---|---|---|
| 6,048,908 A * | 4/2000 | Kitagawa | 521/56 |
| 6,086,825 A | 7/2000 | Sundberg et al. | |
| 6,103,493 A | 8/2000 | Skerra et al. | |
| 6,130,098 A * | 10/2000 | Handique et al. | 436/180 |
| 6,238,626 B1 | 5/2001 | Higuchi et al. | |
| 6,331,441 B1 | 12/2001 | Balch et al. | |
| 6,565,813 B1 * | 5/2003 | Garyantes | 422/553 |
| 6,578,952 B1 * | 6/2003 | Sugiyama et al. | 347/65 |
| 6,664,044 B1 | 12/2003 | Sato | |
| 6,716,629 B2 | 4/2004 | Hess et al. | 435/420 |
| 7,163,823 B2 | 1/2007 | Patno et al. | 435/287.2 |
| 7,344,877 B1 | 3/2008 | Camacho et al. | |
| 2003/0083474 A1 | 5/2003 | Schmidt | |
| 2003/0113813 A1 | 6/2003 | Heidaran et al. | 435/7.2 |
| 2003/0209560 A1 | 11/2003 | Hui et al. | |
| 2004/0106191 A1 | 6/2004 | Muser | 435/304.3 |
| 2004/0136876 A1 | 7/2004 | Fouillet et al. | |
| 2004/0208792 A1 | 10/2004 | Linton et al. | 422/99 |
| 2004/0234966 A1 | 11/2004 | Bryning et al. | |
| 2005/0045539 A1 | 3/2005 | Yu et al. | |
| 2005/0079105 A1 * | 4/2005 | Hunter et al. | 422/100 |
| 2006/0013031 A1 | 1/2006 | Ravkin et al. | |
| 2006/0051249 A1 | 3/2006 | Knebel et al. | |
| 2006/0105453 A1 | 5/2006 | Brenan et al. | 435/325 |
| 2007/0003448 A1 * | 1/2007 | Kanigan et al. | 422/102 |
| 2008/0003671 A1 | 1/2008 | Martin | 435/304.1 |
| 2010/0000304 A1 | 1/2010 | Kim et al. | 73/64.56 |

FOREIGN PATENT DOCUMENTS

| | | | |
|---|---|---|---|
| EP | 1 358 939 A2 | 11/2003 | |
| EP | 1 473 079 A1 | 3/2004 | |
| EP | 1 386 657 B1 | 4/2006 | |
| EP | 1 683 571 | 7/2006 | |
| EP | 1316360 B1 | 9/2006 | |
| EP | 1348533 B1 | 11/2006 | |
| EP | 1 788 047 | 5/2007 | |
| GB | 1 291 610 A | 10/1972 | |
| GB | 2332273 A1 | 6/1999 | |
| GB | 2334954 A | 9/1999 | |
| JP | 3120453 | 12/1998 | |
| JP | 2002/502955 | 1/2002 | |
| JP | 2003-033177 A | 2/2003 | |
| JP | 2004-020280 A | 1/2004 | |
| JP | 2004-077476 A | 3/2004 | |
| JP | 2004-535176 | 11/2004 | |
| JP | 2005-003803 | 1/2005 | |
| JP | 2005-099004 A | 4/2005 | |
| WO | WO9623879 | 8/1996 | |
| WO | WO 98/47003 | 10/1998 | G01N 33/543 |
| WO | WO 98/55852 A1 | 12/1998 | |
| WO | WO 99/39829 | 8/1999 | |
| WO | WO 99/55826 | 11/1999 | |
| WO | WO 00/14311 A1 | 3/2000 | |
| WO | WO 00/58735 A2 | 10/2000 | |
| WO | WO0104144 | 1/2001 | |
| WO | WO03029462 | 4/2003 | |
| WO | WO2004030820 | 4/2004 | |
| WO | WO2004111610 | 11/2004 | |
| WO | WO2005019254 | 3/2005 | |
| WO | WO2005019255 | 3/2005 | |
| WO | WO2005019256 | 3/2005 | |
| WO | WO 2006/004739 A2 | 1/2006 | |
| WO | WO2006046699 | 5/2006 | |
| WO | WO 2007/102785 A1 | 9/2007 | |
| WO | WO 2008/063136 | 5/2008 | G01N 31/20 |
| WO | WO 2010/120249 A1 | 10/2010 | |
| WO | WO 2012/011877 A2 | 1/2012 | |

OTHER PUBLICATIONS

Sundberg, et al., "Contact angle measurements by confocal microscopy for non-destructive microscale surface characterization," Journal of Colloid and Interface Science 313 (2007), 454-460.

Van Oss, C.J., "Long-range and short-range mechanisms of hydrophobic attraction and hydrophilic repulsion in specific and aspecific interactions," J. Mol. Recognit. (2003) 16, 177-190.
Wang, W.-H., "Flow-Focusing Generation of Monodisperse Water Droplets Wrapped by Ionic Liquid on Microfluidic Chips: From Plug to Sphere," Langmuir (2007) 23, 11924-11931.
Wang, W.-H., "In Situ Wilhelmy Balance Surface Energy Determination of Poly(3-hexylthiophene) and Poly(3,4-ethylenedioxythiophene) during Electrochemical Doping-Dedoping," Langmuir (2006) 22, 9287-9294.
West et al., "Microplasma writing for surface-directed millifluidics," Lab-on-a-Chip (2007) 7, 981-983.
Widom et al., "The hydrophobic effect," Phys. Chem. Chem. Phys. (2003) 5, 3085-3093.
Wixforth, A., et al., "Flatland fluidics," mstnews (2002) 5, 42-43.
Roach, et al., "Controlling Nonspecific Protein Adsorption in a Plug-Based Microfluidic System by Controlling Interfacial Chemistry Using Fluorous-Phase Surfactants," Analytical Chemistry, vol. 77, No. 3, pp. 785-796, Feb. 1, 2005.
Washizu, M., "Electrostatic Actuation of Liquid Droplets for Microreactor Applications," IEEE Transactions on Industry Applications, vol. 34, No. 4, Jul./Aug. 1998.
Australian Patent Office; Authorized Officer: Jayati Ray, Written Opinion of the International Searching Authority, International Application No. PCT/SG2007/000393, dated Feb. 20, 2008, 3 pages.
Supplementary Search Report for EP 07835548.4 / PCT/SG2007/000393 dated Jun. 30, 2010.
International Search Report and Written Opinion for International Application PCT/SG2010/000153 dated Sep. 17, 2010.
International Search Report and Written Opinion for International Application PCT/SG2011/000263 dated Feb. 29, 2012.
International Search Report and Written Opinion for International Application PCT/SG2006/000050 dated May 8, 2006.
Asberg, et al., "Surface Energy Modified Chips for Detection of Conformational States and Enzymatic Activity in Biomolecules," Langmuir (2006) 22, 5, 2205-2211.
Beck, M., et al., "Improving stamps for 10 nm level wafer scale nanoimprint lithography," Microelectron. Eng., (2002) 61-62, 441.
Benor, A., et al., "Microstructuring by microcontact printing and selective surface dewetting," Journal of Vacuum Science & Technology B, (2007) 25, 4, 1321-1326.
Beste, et al., "Small antibody-like proteins with prescribed ligand specificities derived from the lipocalin fold," Proc. Natl. Acad. Sci. USA (1999) 96, 1898-1903.
Biffinger, J.C., et al., "The Polar Hydrophobicity of Fluorinated Compounds," ChemBioChem (2004) 5, 622-627.
Burbulis, I., et al., "Quantifying small numbers of antibodies with a 'near-universal' protein-DNA chimera," Nature Methods (2007 DOI: 10.1038/NMETH1127).
Chiriac, H., et al., "Magnetic GMI sensor for detection of biomolecules," Journal of Magnetism and Magnetic Materials (2005) 293, 671-676.
Churaev, N.V. & Sobolev, V.D., "Wetting of low-energy surfaces," Advances in Colloid and Interface Science (2007) 134-135, 15-23.
Daniel, S., et al., "Vibration-Actuated Drop Motion on Surfaces for Batch Microfluidic Processes," Langmuir (2005), 21, 4240-4228.
Dill, K.A., et al., "Modeling Water, The Hydrophobic Effect, and Ion Solvation," Annu. Rev. Biophys. Biomol. Struct. (2005) 34, 173-199.
Gao, L. & McCarthy, T.J., "A Commercially Available Perfectly Hydrophobic Material (δA/δR) 180°/180°)," Langmuir (2007) 23, 18, 9125-9127.
Gascoyne, P.R.C., et al., "Dielectrophoresis-based programmable fluidic processors," Lab-on-a-Chip (2004), 4, 299-309.
Genua, et al., "Functional patterns obtained by nanoimprinting lithography and subsequent growth of polymer brushes," Nanotechnology (2007) 18, 215301.
Gill, D.S. & Damle, N.K., "Biopharmaceutical drug discovery using novel protein scaffolds," Current Opinion in Biotechnology (2006) 17, 653-658.
Giovambattista, et al., "Effect of Surface Polarity on Water Contact Angle and Interfacial Hydration Structure," J. Phys. Chem. B (2007) 111, 9581-9587.

(56) References Cited

OTHER PUBLICATIONS

Goddard & Hotchkiss, "Polymer surface modification for the attachment of bioactive compounds," Progress in Polymer Science (2007) 32, 7, 698-725.
Griffiths, A.D. & Tawfik, D.S., "Miniaturising the laboratory in emulsion droplets," Trends in Biotechnology (2006) 24, 9, 395-402.
Herrmann, M., et al., "Enzymatically-generated fluorescent detection in micro-channels with internal magnetic mixing for the development of parallel microfluidic ELISA," Lab-on-a-Chip (2006) 6, 555-560.
Holt, L.J., et al., "Domain antibodies: proteins for therapy," Trends Biotechnol. (2003), 21, 11, 484-490.
Hutten, A., et al., "New magnetic nanoparticles for biotechnology," J. Biotech. (2004), 112, 47-63.
Iliades, P., et al., "Triabodies: single chain Fv fragments without a linker form trivalent trimers," FEBS Lett (1997) 409, 437-441.
Jakobs and Hanein, "Micrometer scale gel patterns," Colloids & Surfaces A: Physciochem. Eng. Aspects (2006) 290, 33-40.
Jung, Y.C. & Bhushan, B., "Wetting transition of water droplets on superhydrophobic patterned surfaces," Scripta Materialia (2007) 57, 1057-1060.
Kanta, et al., "Preparation of Silica-on-Titania Patterns with a Wettability Contrast," Langmuir (2005) 21, 5790-5794.
Kwon, Y.-U., & Kodadek, T. J., "Quantitative Evaluation of the Relative Cell Permeability of Peptoids and Peptides," J. Am. Chem. Soc. (2007) 129, 1508-1509.
Kusumaatmaja, H. & Yeomans, J.M., "Controlling Drop Size and Polydispersity Using Chemically Patterned Surfaces," Langmuir (2007) 23, 956-959.
Li, et al., "What do we need for a superhydrophobic surface? A review on the recent progress in the preparation of superhydrophobic surfaces," Chem. Soc. Rev. (2007) 36, 1350-1368.
Stone, E., et al., "The assembly of single domain antibodies into bispecific decavalent molecules," Journal of Immunological Methods 318 (2007), 88-94.
Lundgren, M., et al., "Modeling of Wetting: A Study of Nanowetting at Rough and Heterogeneous Surfaces," Langmuir (2007) 23, 1187-1194.
Ma & Hill, "Superhydrophobic surfaces," Current Opinion in Colloid & Interface Science 11 (2006), 193-202.
Mardare, A.I., et al., "Microelectrochemical lithography: A method for direct writing of surface oxides,"Electrochimica Acta 52 (2007), 7865-7869.
Matsuda, T., et al., "Phosphorylcholine-endcapped oligomer and block co-oligomer and surface biological reactivity," Biomaterials 24 (2003), 4517-4527.
Meyer, et al., "Recent progress in understanding hydrophobic interactions," Proc. Natl. Acad. Sci. U.S.A. (2006) 103, 43, 15739-15746.
Mosavi, L.K., et al., "The ankyrin repeat as molecular architecture for protein recognition," Protein Science (2004) 13, 6, 1435-1448.
Opdahl, A., et al., "Polymer Surface Science," The Chemical Record (2001) 1, 101-122.
Pollack, M.G., et al., "Electrowetting-based actuation of liquid droplets for microfluidic applications,"Appl. Phys. Lett. (2000), 77, 1725-1726.
Popp, M.W., et al., "Sortagging: a versatile method for protein labeling," Nature Chemical Biology (2007) 3, 11, 707-708.
Rastogi, V. & Velev, O.D., "Development and evaluation of realistic microbioassays in freely suspended droplets on a chip," Biomicrofluidics (2007) 1, 014107-1-014107-17.
Ronaghi, M., "Pyrosequencing Sheds Light on DNA Sequencing," Genome Research (2001), 11, 3-11.
Roach, et al., "Controlling Nonspecific Protein Adsorption in a Plug-Based Microfluidic System by Controlling Interfacial Chemistry Using Fluorous-Phase Surfactants," Anal. Chem. (2005), 77, 785.
Rose, D., "Microdispensing technologies in drug discovery," Drug Discovery Today (1999), 4, 411-419.
Satriano, C., et al., "Bacterial adhesion onto nanopatterned polymer surfaces," Materials Science & Engineering C 26 (2006) 942-946.
Silverman, J., et al., "Multivalent avimer proteins evolved by exon shuffling of a family of human receptor domains," Nature Biotechnology (2005) 23, 1556-1561.
Skerra, A., "Engineered protein scaffolds for molecular recognition," J. Mol. Recognit. (2000) 13, 167-187.
Song, J.M. & Vo-Dinh, T., "Miniature biochip system for detection of *Escherichia coli* O157:H7 based on antibody-immobilized capillary reactors and enzyme-linked immunosorbent assay," Analytica Chimica Acta 507 (2004), 115-121.
Stephenson, et al., "Quantifying the Hydrophobic Effect. 1. A Computer Simulation-Molecular-Thermodynamic Model for the Self-Assembly of Hydrophobic and Amphiphilic Solutes in Aqueous Solution," J. Phys. Chem. B. (2007) 111, 1025-1044.
Kaori & Kobayashi, "Method of Manufacturing Pattern Formation," Abstract of JP2005003803, (2005).
Fielder, U., et al., "Fabrication of Beta-Pleated Sheet Proteins With Specific Binding Properties," Abstract of WO200104144, (2001).
Furukawa, Y., et al., "Process for Production of Substrates Having Water-Repellent Hydrophilic Films on the Surface," Abstract of WO2006046699, (2006).
Agency for Science, Technology and Research, International Preliminary Report on Patentability, PCT/SG2007/000393, May 26, 2009, 4 pgs.
Agency for Science, Technology and Research, Notification of Reasons for Refusal, JP 2009-538373, Nov. 10, 2011, 7 pgs.
Agency for Science, Technology and Research, Notification of the First Office Action, CN 200780048922.8, Nov. 12, 2010, 4 pgs (available in Chinese only).
Agency for Science, Technology and Research, Notification of the Second Office Action, CN 200780048922.8, May 17, 2011, 4 pgs.
Agency for Science, Technology and Research, Notification on the Grant of Patent Right for Invention, CN 200780048922.8, Sep. 22, 2011, 1 pg.
Curiox Biosystems Pte Ltd, International Preliminary Report on Patentability, PCT/SG2010/000153, Oct. 18, 2011, 15 pgs.
Curiox Biosystems Pte Ltd, International Preliminary Report on Patentability, PCT/SG2011/000263, Dec. 21, 2012, 5 pgs.
Curiox Biosystems Pte Ltd, International Search Report and Written Opinion, PCT/IB2013/000623, Jul. 10, 2013, 10 pgs.
Kim, Final Office Action, U.S. Appl. No. 13/264,913, Jun. 21, 2013, 11 pgs.
Kim, Notice of Allowance, U.S. Appl. No. 12/282,162, May 14, 2012, 7 pgs.
Kim, Office Action, U.S. Appl. No. 12/282,162, Jun. 27, 2011, 8 pgs.
Kim, Office Action, U.S. Appl. No. 13/264,913, Nov. 7, 2012, 9 pgs.
Kim, Office Action, U.S. Appl. No. 13/264,913, Sep. 26, 2013, 10 pgs.
Leck, Final Office Action, U.S. Appl. No. 11/984,197, May 8, 2012, 10 pgs.
Leck, Office Action, U.S. Appl. No. 11/984,197, Mar. 14, 2013, 11 pgs.
Leck, Office Action, U.S. Appl. No. 11/984,197, May 26, 2011, 11 pgs.
Leck, Office Action, U.S. Appl. No. 11/984,197, Jul. 31, 2013, 12 pgs.
Perfulorodecalin-FluoroMed, http://fluoromed.com/products/perfluorodecalin.html (no date).

* cited by examiner

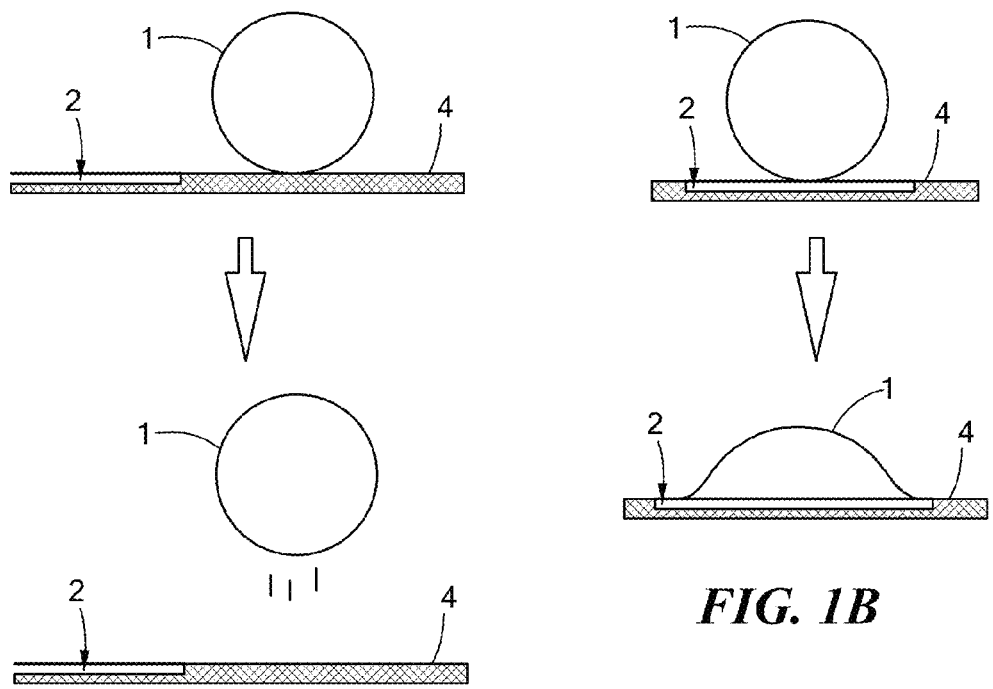
FIG. 1A
FIG. 1B
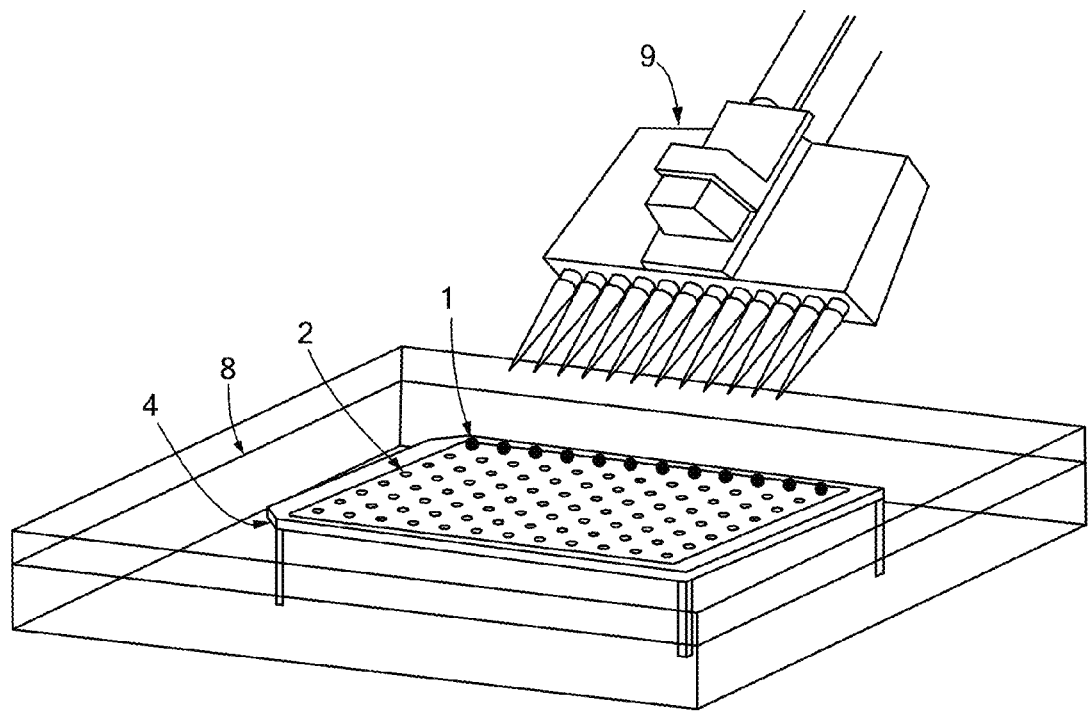
FIG. 1C

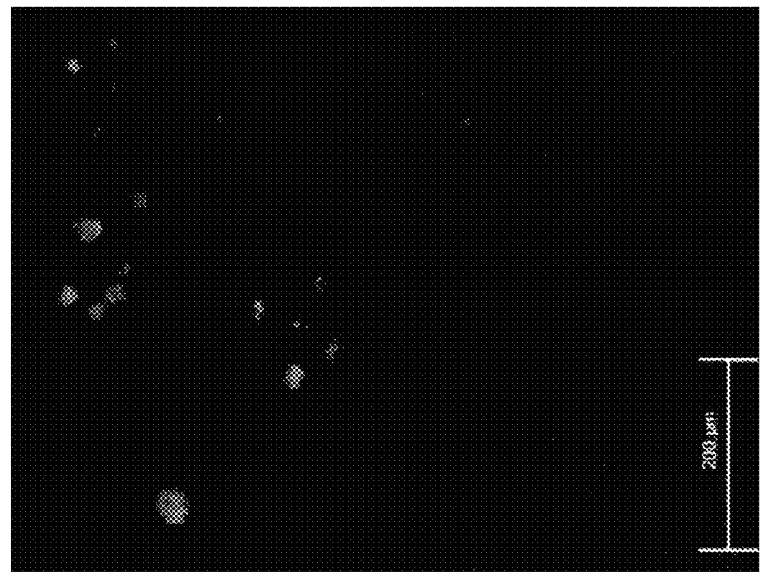
*FIG. 11B*
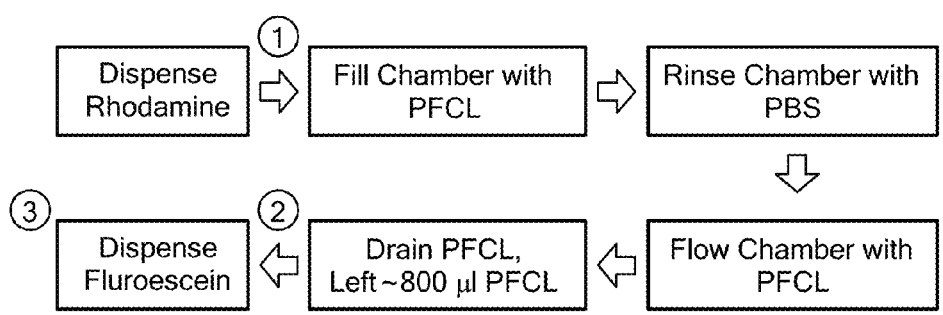
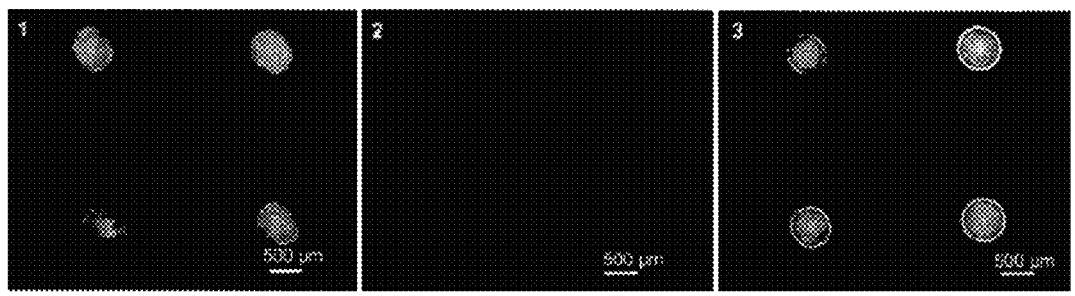
*FIG. 12*

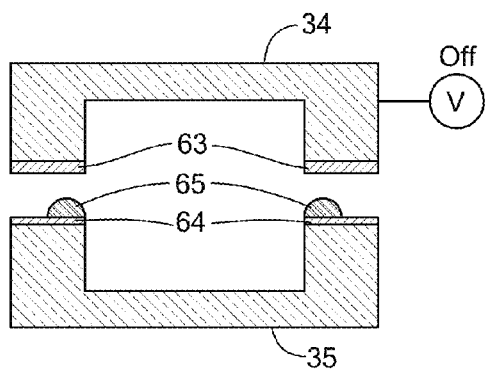 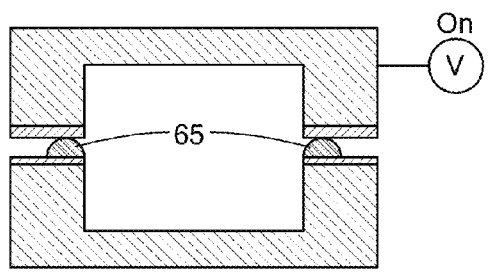
*FIG. 23A*  *FIG. 23B*
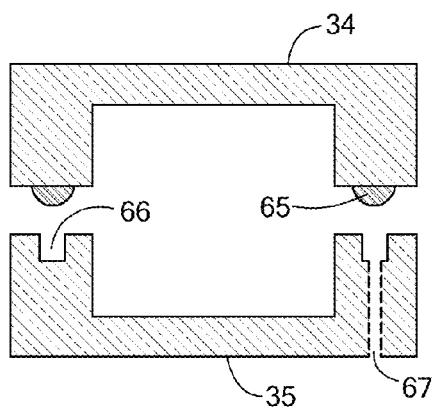 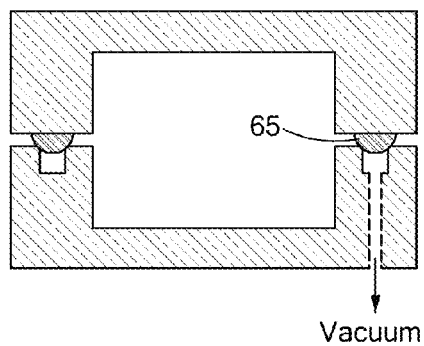
*FIG. 24A*  *FIG. 24B*
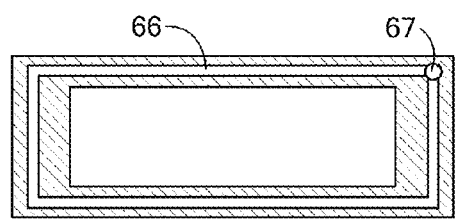
*FIG. 24C*

US 8,691,147 B2

APPARATUS FOR PROCESSING A SAMPLE IN A LIQUID DROPLET AND METHOD OF USING THE SAME

CROSS-REFERENCE TO RELATED APPLICATIONS

This application is a continuation-in-part of international patent application PCT/SG2006/000363 entitled "Apparatus for processing a sample in a liquid droplet and method of using the same" filed on Nov. 24, 2006 with the Intellectual Property Office of Singapore. The contents of said application filed on Nov. 24, 2006 is incorporated herein by reference for all purposes in its entirety.

FIELD OF THE INVENTION

The present invention relates to an apparatus and a method for processing a biological and/or chemical sample in a liquid droplet.

BACKGROUND OF THE INVENTION

Miniaturization continues to be an enabling technology in bioinstrumentation that offers key advantages to research in life sciences and pharmaceuticals. Miniaturization provides significant cost savings from low consumption of reagents, with potential time savings from faster reaction rates in methods involving heterogeneous solid supports. As a result, data throughput can be significantly increased without an associated increase in costs.

Efforts on miniaturization in bioinstrumentation have delivered a number of revolutionary tools and opened a new venue in life science and pharmaceutical research. Notably, miniaturization enabled large-scale analysis of biological samples at a lower cost, faster speed and simpler operation, and brought about the era of '-omics'. A well-known example of a miniaturized device is a DNA microarray. It allows for a large-scale parallel analysis or reaction of samples in a relatively short time and at a low cost. Efforts are currently taken to miniaturize the commonly used multiwell plate (also called "Micro-Titer Plate®"). By means of automation of sample handling high-throughput screening can be performed. It has been proposed to extend the respective miniaturization approach by disposing drops of cells onto a substrate, so that they are substantially arranged in a monolayer (cf. International Patent Application WO 2004/111610).

A problem not only occurring at solid-water, but also at air-water and, where applicable, oil-water interfaces is protein adsorption. Recently, Roach et al. (*Anal. Chem.* (2005), 77, 785) characterized non-specific protein adsorption at the aqueous-perfluorocarbon interface, as well as ways to control adsorption. In their work, an aqueous droplet of protein and enzyme was encapsulated by perfluorocarbon liquid containing perfluorocarbon-ethylene glycol surfactants. The perfluorocarbon liquid-aqueous interface minimized non-specific adsorption of fibrinogen and bovine serum albumin at the interface. The activities of ribonuclease A and alkaline phosphatase at nanoliter scale surrounded by the perfluorocarbon-aqueous interface were identical to those at the bulk scale. The interface between perfluorocarbon liquid and aqueous solution, particularly in embodiments where for instance a perfluorocarbon-ethylene glycol surfactant is present, provides a biocompatible surface in addition to minimizing evaporation of the aqueous solution. Perfluorocarbon liquid is known to provide one of the most biocompatible interfaces among water-immiscible liquids.

A further problem in the use of microdevices, particularly during incubation at for instance 37° C., prolonged storage and extended sample preparation using for instance large numbers of multiwell plates for screening purposes is evaporation. Currently used means to overcome this problem are the use of multiwell-plate covers or seal-strips, stacking, the use of closed microchips and the optimization of assay protocols in order to minimize waiting time. Evaporation is of particular practical concern, since it can falsify data if it occurs unevenly across multiwell plates.

The manipulation of droplets has recently received considerable interest due to the possibility of isolating and handling volumes down to the picoliter/femtoliter range (cf. e.g. International Patent Application WO 2004/030820). Biochemical reactions have for instance been carried out in emulsion droplets (Griffiths, A D, & Tawfik, D S, *Trends in Biotechnology* (2006) 24, 9, 395-402). Several lab-on-a-chip (LOC), micro total analysis (µTAS), and biological microelectromechanical systems (BioMEMS) have been developed for moving, merging/mixing, splitting, and heating of droplets on surfaces, such as electrowetting-on-dielectric (EWOD) [Pollack, M. G. et al., *Appl. Phys. Lett.* (2000), 77, 1725-1726], surface acoustic waves (SAW) [Wixforth, A. et al., mstnews (2002), 5, 42-43], dielectrophoresis [Cascoyne, P. R. C. et al., *Lab-on-a-Chip* (2004), 4, 299-309], and locally asymmetric environments [Daniel, S. et al., *Langmuir* (2005), 21, 4240-4228]. These methods are however not well suited for methods with a sequence of steps, such as separating, purifying and isolating starting material and/or reaction products from crude or complex mixtures. Such steps may, for example, require rinsing or washing, which can presently only be carried out in multiwell plates, using e.g. automated standard laboratory robots. In order to circumvent these disadvantages, ELISA platforms with microcapillaries and microchannels have been employed (Song, J M. & Vo-Dinh, T, *Analytica Chimica Acta* (2004), 507, 115-121; Herrmann, M, et al., *Lab-on-a-Chip* (2006) 6, 555-560). Such platforms are however more cumbersome and expensive, as well as less flexible and convenient to use.

Accordingly it is an object of the present invention to provide an apparatus and a method for processing a chemical and/or biological sample which avoids the above discussed disadvantages.

SUMMARY OF THE INVENTION

In a first aspect the present invention provides an apparatus for processing a biological and/or chemical sample in a liquid droplet. The apparatus includes a processing compartment. The processing compartment is defined by a reservoir and an immobilisation member. The processing compartment is further adapted to accommodate a medium. The medium is immiscible with the liquid droplet. Furthermore the medium is of a lower surface energy than the liquid of the liquid droplet. The reservoir is defined by a circumferential wall and a base. The immobilisation member is arranged within the reservoir. The immobilisation member includes a surface. The surface is patterned in such a way that it includes at least one predefined immobilisation area. The at least one predefined immobilisation area is of a higher surface energy than the medium. Furthermore the at least one predefined immobilisation area is of a higher surface energy than the respective remaining surface of the patterned surface of the immobilisation member. The at least one predefined immobilisation area is additionally of a sufficient width in the plane of the surface to allow, in the medium, the immobilisation of the liquid droplet on the at least one predefined immobilisation area via interfacial interactions. The remaining surface is of at most about the same surface energy as the medium that is immiscible with the liquid droplet.

According to some embodiments, the medium is a hydrophobic medium. The hydrophobic medium is immiscible with the liquid droplet and of higher hydrophobicity than the liquid of the liquid droplet. The immobilisation member of such embodiments includes a hydrophobic surface. The hydrophobic surface is patterned in such a way that it includes at least one predefined hydrophilic, such as a polar, immobilisation area. The at least one hydrophilic immobilisation area within the hydrophobic surface is of a sufficient width in the plane of the surface to allow, in the hydrophobic medium, the immobilisation of the liquid droplet on the hydrophilic area via hydrophilic-hydrophilic (e.g. polar) interactions. The remaining hydrophobic surface is of maximally the same hydrophobicity as a respective hydrophobic medium.

According to some embodiments, the apparatus includes an immobilisation member with a plurality of predefined immobilisation areas as described above. A respective immobilisation member thus defines a microarray of independently controllable bioreactors.

According to some particular embodiments of the apparatus of the present invention, the immobilisation member of the processing compartment is removably arranged within the apparatus. The immobilisation member may for example be removed or inserted from/into the reservoir via an opening of the apparatus, which may be located on a top of the reservoir.

According to some embodiments the apparatus includes an upper inlet, such as an opening. The immobilisation member can also be removed or inserted from/into the reservoir via this upper inlet.

In a second aspect the invention provides a device for attaching an inlet member and/or a cover to the reservoir of an apparatus according to the first aspect. The device includes a first holder and a second holder. The first holder is designed to accommodate the reservoir. The second holder is designed to accommodate an inlet member and/or a cover. The first and the second holder are fitted such the second holder can be positioned on a top of the first holder.

In a third aspect, the invention provides a device for guiding and/or positioning a dispenser on a top of the reservoir of an apparatus of the first aspect. The apparatus includes an upper inlet that is defined by an opening (see above). The device for guiding and/or positioning a dispenser is designed to be received by the upper opening of the apparatus.

In a fourth aspect, the invention provides a method of processing a biological and/or chemical sample in a liquid droplet. The method includes providing an apparatus as described above. The method also includes disposing the medium into the apparatus. Thereby the predefined immobilisation area, which is included within the patterned surface of the immobilisation member, is entirely covered by the medium. The method further includes providing the liquid droplet and disposing the liquid droplet onto the predefined immobilisation area that is included within the patterned surface of the immobilisation member. Thereby the liquid droplet is immobilised on said predefined immobilisation area via interfacial interactions. The method also includes performing a process on the biological and/or chemical sample in the liquid droplet.

According to some embodiments of the method of the present invention, providing the apparatus may include providing a device, which is then assembled to the apparatus as described above. A respective device may include a reservoir defined by a circumferential wall and a base. The reservoir is capable of receiving an immobilisation member. The immobilisation member may be disposed into the reservoir, whereby the processing compartment of the apparatus is formed.

According to some embodiments of the method of the present invention, performing a process on the biological and/or chemical sample includes rinsing or mixing the liquid droplet, or adding or subtracting liquid. For this purpose the immobilisation member may also be removed from the reservoir. Where the immobilisation member has a plurality of predefined immobilisation areas (supra), rinsing, mixing, adding or subtracting may be separately be performed for each individual predefined area of the patterned surface.

Accordingly, the apparatus and method of the invention allow a handling of the respective immobilisation member—and thus of a respective sample immobilised thereon, that may include any process that can be performed on a standard multi-well plate. A wide range of chemical processes and biological assay can therefore be performed on the micro scale and below, when using the apparatus and method of the present invention.

BRIEF DESCRIPTION OF THE DRAWINGS

The invention will be better understood with reference to the detailed description when considered in conjunction with the non-limiting examples and the accompanying drawings, in which:

FIG. 1 depicts a droplet contacting the patterned surface of an immobilisation member (4) (FIG. 1A), a predefined hydrophilic immobilisation area (2) included in a remaining hydrophobic surface (FIG. 1B), and dispensing multiple droplets onto a plurality of respective hydrophilic areas by means of a dispenser (9), once the immobilisation member has been immersed in a hydrophobic medium (8) (FIG. 1C).

FIG. 11 B depicts an immunofluorescence staining of the same cells using a Ki67 primary antibody, followed by an Alexa-633 secondary antibody.

FIG. 12 depicts fluorescent images of a glass slide patterned with 500-mm features: (1) dispensing of 50 nl of rhodamine dye, (2) washing with PBS buffer, and (3) dispensing of 50 nl of fluorescein dye.

FIG. 23 depicts a means of assembling a processing compartment (35) and a chamber cover (34) (A), and sealing by electromagnetic force via elastomeric contact (B). An electromagnet (63), either exposed at the surface or embedded below the surface and a metallic strip (64), either exposed at the surface or embedded below the surface, provide the means for sealing, together with an O-ring (65).

FIG. 24 depicts a means of assembling a processing compartment of an apparatus of the invention (35) and a chamber cover (34) and sealing by pressure difference, assisted by an O-ring (65). Side view (A before, B after sealing) and top view (C) show a fluid channel (66) embedded in the circumferential side wall of the apparatus around a slide chamber. A vacuum channel (67) allows for applying vacuum.

DETAILED DESCRIPTION OF THE INVENTION

Figure 2A:
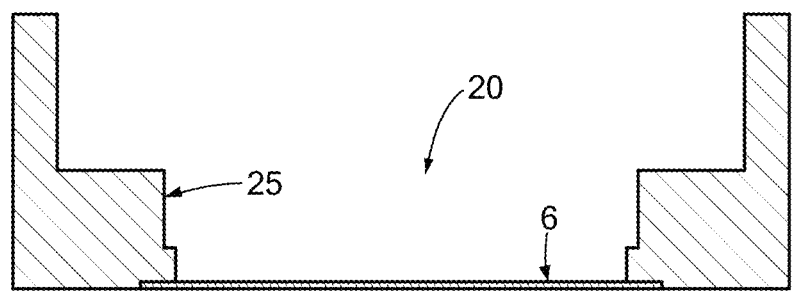
FIG. 2 depicts embodiments of an apparatus (A, B, C) of the invention where a chip is used (illustrated in D, E, F, G, H) that includes a plurality of predefined immobilisation areas within a patterned surface.

The present invention provides an apparatus and a method of processing a biological and/or chemical sample. The apparatus and method are suitable for any process, in particular a process that can be performed in a liquid on a miniaturized scale (cf. below).

The sample may be of any origin. It may for instance, but not limited to, be derived from humans, animals, plants, bacteria, viruses, spores, fungi, or protozoae, or from organic or inorganic materials of synthetic or biological origin. Accordingly, any of the following samples selected from, but not limited to, the group consisting of a soil sample, an air sample, an environmental sample, a cell culture sample, a bone marrow sample, a rainfall sample, a fallout sample, a sewage sample, a ground water sample, an abrasion sample, an archaeological sample, a food sample, a blood sample, a serum sample, a plasma sample, an urine sample, a stool sample, a semen sample, a lymphatic fluid sample, a cerebrospinal fluid sample, a nasopharyngeal wash sample, a sputum sample, a mouth swab sample, a throat swab sample, a nasal swab sample, a bronchoalveolar lavage sample, a bronchial secretion sample, a milk sample, an amniotic fluid sample, a biopsy sample, a cancer sample, a tumour sample, a tissue sample, a cell sample, a cell culture sample, a cell lysate sample, a virus culture sample, a nail sample, a hair sample, a skin sample, a forensic sample, an infection sample, a nosocomial infection sample, a production sample, a drug preparation sample, a biological molecule production sample, a protein preparation sample, a lipid preparation sample, a carbohydrate preparation sample, a space sample, an extraterrestrial sample or any combination thereof may be processed in the method. Where desired, a respective sample may have been preprocessed to any degree. As an illustrative example, a tissue sample may have been digested, homogenised or centrifuged prior to being used with the device of the present invention. The sample may furthermore have been prepared in form of a liquid, such as a solution. Examples include, but are not limited to, a solution or a slurry of a nucleotide, a polynucleotide, a nucleic acid, a peptide, a polypeptide, an amino acid, a protein, a synthetic polymer, a biochemical composition, an organic chemical composition, an inorganic chemical composition, a metal, a lipid, a carbohydrate, a combinatory chemistry product, a drug candidate molecule, a drug molecule, a drug metabolite or of any combinations thereof. Further examples include, but are not limited to, a suspension of a metal, a suspension of metal alloy, and a solution of a metal ion or any combination thereof, as well as a suspension of a cell, a virus, a microorganism, a pathogen, a radioactive compound or of any combinations thereof. It is understood that a sample may furthermore include any combination of the aforementioned examples.

Often, but not necessarily, the sample will include, or will be expected to include, target matter or a precursor thereof. Such embodiments shall be illustrated by a number of examples: The target matter may for instance be a cell or a molecule added to or included in the sample, and it may be desired to obtain it in a purified or enriched form. As another example, the target matter may be a compound known or theorized to be obtainable from a precursor compound by means of a chemical process. In this case the sample may for instance include a solution of such a precursor compound. As further example, a cell culture media may be suspected to be contaminated. In this case, the method of the present invention may be used to identify the type of contaminant.

The target matter or precursor thereof may thus be of any nature. Examples include, but are not limited to, a nucleotide, an oligonucleotide, a polynucleotide, a nucleic acid, a peptide, a polypeptide, an amino acid, a protein, a synthetic polymer, a biochemical composition, a glycoprotein, a radioactive compound, a polyelectrolyte, a polycation, a polyanion, a polycatanion, a pathogen, an organic chemical composition, an inorganic chemical composition, a lipid, a carbohydrate, a combinatory chemistry product, a drug candidate molecule, a drug molecule, a drug metabolite, a cell, a virus, a microorganism or any combinations thereof. In embodiments where the target matter is for example a protein, a polypeptide, a peptide, a nucleic acid, a polynucleotide or an oligonucleotide, it may contain an affinity tag. Examples of affinity tags include, but are not limited to biotin, dinitrophenol or digoxigenin. Where the target matter is a protein, a polypeptide, or a peptide, further examples of an affinity tag include, but are not limited to, oligohistidine (such as a penta- or hexahistidine-tag), polyhistidine, a streptavidin binding tag such as the STREP-TAGS® described in US patent application US 2003/0083474, U.S. Pat. Nos. 5,506,121 or 6,103,493, an immunoglobulin domain, maltose-binding protein, glutathione-S-transferase (GST), calmodulin binding peptide (CBP), FLAG-peptide (e.g. of the sequence Asp-Tyr-Lys-Asp-Asp-Asp-Asp-Lys-Gly), the T7 epitope (Ala-Ser-Met-Thr-Gly-Gly-Gln-Gln-Met-Gly), maltose binding protein (MBP), the HSV epitope of the sequence Gln-Pro-Glu-Leu-Ala-Pro-Glu-Asp-Pro-Glu-Asp of herpes simplex virus glycoprotein D, the Vesicular Stomatitis Virus Glycoprotein (VSV-G) epitope of the sequence Tyr-Thr-Asp-Ile-Glu-Met-Asn-Arg-Leu-Gly-Lys, the hemagglutinin (HA) epitope of the sequence Tyr-Pro-Tyr-Asp-Val-Pro-Asp-Tyr-Ala and the "myc" epitope of the transcription factor c-myc of the sequence Glu-Gln-Lys-Leu-Ile-Ser-Glu-Glu-Asp-Leu. Where the target matter is a nucleic acid, a polynucleotide or an oligonucleotide, an affinity tag may furthermore be an oligonucleotide tag. Such an oligonucleotide tag may for instance be used to hybridize to an immobilised oligonucleotide with a complementary sequence. A respective affinity tag may be located within or attached to any part of the target matter. As an illustrative example, it may be operably fused to the amino terminus or to the carboxy terminus of any of the aforementioned exemplary proteins.

The apparatus of the present invention is designed to process the biological and/or chemical sample when included in a liquid droplet. This sample may be deposited into the liquid droplet by any means (cf. below).

The droplet may contain or essentially consist of any desired liquid whether an aqueous or non aqueous liquid, an organic liquid (solvent), or a nonpolar aprotic, nonpolar protic, dipolar protic, dipolar aprotic, or an ionic liquid. It should be understood that suitable liquids will allow for the desired process to take place. Examples of nonpolar aprotic liquids include, but are not limited to, hexane, heptane, cyclohexane, benzene, toluene, pyridine, dichloromethane, chloroform, carbon tetrachloride, carbon disulfide, tetrahydrofuran, dioxane, diethyl ether, diisopropylether, ethylene glycol monobutyl ether or tetrahydrofuran. Examples of dipolar aprotic liquids are methyl ethyl ketone, methyl isobutyl ketone, acetone, cyclohexanone, ethyl acetate, isobutyl isobutyrate, ethylene glycol diacetate, dimethylformamide, acetonitrile, N,N-dimethyl acetamide, nitromethane, acetonitrile, N-methylpyrrolidone, and dimethylsulfoxide. Examples of polar protic liquids are water, methanol, ethanol, butyl alcohol, formic acid, dimethylarsinic acid [$(CH_3)_2AsO(OH)$], N,N-dimethylformamide, N,N-diisopropylethylamine, or chlorophenol. Examples of nonpolar protic liquids are acetic acid, tert.-butyl alcohol, phenol, cyclohexanol, or aniline. Two illustrative examples of ionic liquids are 1,3-dialkylimidazolium-tetrafluoroborates and 1,3-dialkylimidazolium-hexafluoroborates. In some embodiments the liquid of the droplet is or includes a hydrophilic liquid. In some embodiments the liquid of the droplet is dipolar, such as for example a dipolar hydrophilic liquid (see also below). In some embodiments the liquid droplet may include regions, including phases, of different composition, such as regions that are defined by different liquids.

In this conjunction it is noted that a droplet that may be used in the invention may be of any viscosity that is suitable for the desired process to be carried out. Besides including or being an aqueous solution of low viscosity that is typically used in enzymatic assays or an organic solvent, the droplet may for instance also include, or consist of, highly viscous material, for instance castor oil, a molten polymer or a peptide hydrogel such as peptide hydrogels commercially available from Becton, Dickinson and Co, if used for the cultivation of cells. The droplet may, for example, also be of high viscosity if it is used for protein crystallization and thus has a high salt concentration or includes precipitation agents such as polyethylene 8000, polyethylene 4000 or polyethylene 1000 which are commonly used for protein crystallization.

An illustrative example of a droplet that may be used in the invention is a hydrosome, an optically-trappable aqueous nanodroplet. A hydrosome is surrounded by a fluorocarbon medium that is immiscible with water. A hydrosome is surrounded by a medium that has an index of refraction that is lower than water. Thus a hydrosome is not only stable but also optically trappable by a focused laser beam. At the same time an encapsulated molecule in the hydrosome can be interrogated and examined by e.g. fluorescence excitation, including for instance time-resolved fluorescence anisotropy studies. A molecule inside such a nanodroplet is able to rotate freely and does not stick or aggregate at the boundary. As further explained below, various other media may be used in the method of the invention, whether of lowe, comparable, identical or higher index of refraction than the liquid of the liquid droplet.

The droplet may also contain more than one liquid. If more than one liquid is used, the liquids may be generally miscible with each other in the selected ratio. In other embodiments the liquid droplet may include two or more liquids that are immiscible, thereby forming separate phases within the liquid droplet. Nevertheless the droplet in its entirety is of a surface energy that is higher than the surface energy of the medium. As an illustrative example, the predefined surface area may be a hydrophilic, including a polar, surface area. In such embodiments at least such an essential part of the liquid droplet is of a hydrophilic liquid that the liquid droplet is capable of being attracted via e.g. hydrophilic (including polar) interactions to the hydrophilic surface, and of being immobilised thereon. The liquid droplet may for instance be a water droplet. In some embodiments the droplet in its entirety is also of a surface energy that is about similar or higher than the surface energy of the predefined area of the patterned surface of the immobilisation member. As further explained below there is however no particular relationship in surface energy required between the liquid droplet and the predefined immobilisation area. The surface energies of the droplet and the immobilisation area are only required to be higher than the surface energies of the residual surface of the immobilisation member and of the medium that is immiscible with the liquid droplet.

Hydrophilic ("water-loving") matter, including surfaces and liquids, also termed lipophobic ("fat-fearing"), contains molecules which can form dipole-dipole interactions with water molecules. Hydrophilic liquids thus dissolve therein. Hydrophobic ("water-fearing") matter has a tendency to separate from water. A related term is the indication lipophilic ("fat-loving"). Lipophilic matter attracts non-polar organic compounds, such as oils, fats, or greases. It is understood that the terms "hydrophobic" and "lipophilic" are not synonymous. For example, perfluorocarbon compounds are both hydrophobic and oleophobic, i.e. lack an affinity for oils. Such compounds accordingly have a tendency to separate from both water and hydrocarbons, though the latter to a lesser extent than from water (see also below).

In many embodiments a hydrophilic liquid or surface is at the same time a polar liquid or surface and a hydrophobic liquid or surface is often a non-polar liquid or surface. Similarly, in relative terms, a more hydrophilic liquid or surface is often at the same time more polar and a more hydrophobic liquid or surface less polar than a respective liquid/surface to which it is compared. A measure for the relative hydrophobicity/hydrophilicity of liquids is the entropy of aqueous solvation. Introducing a hydrocarbon molecule into water is accompanied by an increase in an associated free energy. Noteworthy, the solubility of a hydrocarbon compound in water decreases with increasing temperature at low temperatures. With increasing temperatures solubility often reaches a minimum, whereafter it may increase again with a further increase in temperature. As this effect cannot be explained in terms of polarity, it is clear that the pairs "polar"/"non-polar" and "hydrophilic"/"hydrophobic" are not synonymous. The terms "hydrophilic" and "hydrophobic" as used herein within the context of a medium, and in particular of liquids, generally refer—unless stated otherwise—to the entropy of aqueous solvation at 20° C. When used in the context of a surface, such as a solid surface, the terms "hydrophilic" and "hydrophobic" generally refer—unless stated otherwise—to the wettability and non-wettability, respectively, of a surface in question for water. As an example, a first surface area that is more hydrophobic than a second surface area is more water-repellent than the second surface area.

An interesting example of a highly dipolar chemical bond—much more polar than a carbon-hydrogen bond—is the carbon-fluorine bond. A carbon-fluorine bond provides a molecule, in which it is included with hydrophobic properties (see e.g. Biffinger, J. C., et al. *ChemBioChem* (2004) 5, 622-627; incorporated herein by reference in its entirety for all purposes). A compound with a high number of carbon-fluorine bonds is therefore typically particularly hydrophobic. The carbon-fluoron bond is at the same time relatively non-polarizable, nevertheless fluorinated hydrocarbon compounds can in the gas phase undergo or participate in dipole-dipole and point-dipole interactions. Carbon-fluorine bonds do however not form dipole-dipole interactions with water molecules in the liquid phase. A further interesting property provided by the carbon-fluoron bond concerns perfluorocarbon compounds. These compounds can form a fluorous phase which is a phase immiscible not only with water or hydrophilic solvents but also with hydrophobic solvents such as hydrocarbons. This property has been provided with the words "perfluorophilic" ("perfluoro-carbon-loving") and "perfluoro-phobic". Using a composition that includes a fluorine containing copolymer, a surfactant and an aqueous medium a surface can be provided with a coating that is both water- and oil-repellent (European Patent Application 1 788 047).

The unfavourable free energy change upon dissolving a hydrocarbon molecule in water are in the art explained as resulting from structural changes in water around each solute molecule and as being correlated to the hydrogen bonding geometry of water, which determines fixed angular interactions (for an overview see Dill, K. A. et al., *Ann Rev. Biophys Biomol. Struct.* (2005) 34, 173-199). The hydrophobic effect of liquids has been reviewed by Widom et al. (*Phys. Chem. Chem. Phys.* (2005) 5, 3085-3093; incorporated herein by reference in its entirety for all purposes). A further review on the hydrophobic effect of surfaces, including liquid-liquid, liquid-solid and solid solid surfaces, with a focus on direct force measurements has been given by Meyer et al. (*Proc. Natl. Acad. Sci. U.S.A.* (2006) 103, 43, 15739-15746). A computer simulation-molecular thermodynamic model on the hydrophobic effect, including a demonstration on oil aggregates, has been presented by Stephenson et al. (*J. Phys. Chem. B* (2007) 111, 1025-1044; incorporated herein by reference in its entirety for all purposes).

Examples of a hydrophilic liquid include, but are not limited to water, acetone, methanol, ethanol, propanol, isopropanol, butanol, tetrahydrofuran, pyridine, chloroform, ethylene glycol monobutyl ether, pyridine, ethyl acetate, acetonitrile, dimethylformamide, N,N-dimethyl acetamide, N-methylpyrrolidone, formic acid, formamide, and a polar ionic liquid. Examples of a polar ionic liquid include, but are not limited to, 1-ethyl-3-methylimidazolium tetrafluoroborate, N-butyl-4-methylpyridinium tetrafluoroborate, 1,3-dialkylimidazolium-tetrafluoroorate, 1,3-dialkylimidazolium-hexafluoroborate, 1-ethyl-3-methylimidazolium bis(pentafluoroethyl)phosphinate, 1-butyl-3-methylimidazolium tetrakis(3,5-bis(trifluoromethylphenyl)borate, tetrabutyl-ammonium bis(trifluoromethyl)imide, ethyl-3-methylimidazolium trifluoromethanesulfonate, 1-butyl-3-methylimidazolium methylsulfate, 1-n-butyl-3-methylimidazolium ([bmim]) octylsulfate, and 1-n-butyl-3- methylimidazolium tetrafluoroborate. Examples of a non-polar liquid include, but are not limited to mineral oil, hexane, heptane, cyclohexane, benzene, toluene, dichloromethane, chloroform, carbon tetrachloride, carbon disulfide, dioxane, diethyl ether, diisopropylether, methyl propyl ketone, methyl isoamyl ketone, methyl isobutyl ketone, cyclohexanone, isobutyl isobutyrate, ethylene glycol diacetate, and a non-polar ionic liquid. Examples of a non-polar ionic liquid include, but are not limited to, 1-ethyl-3-methylimidazolium bis[(trifluoromethyl)sulfonyl]amide bis(triflyl)amide, 1-ethyl-3-methylimidazolium bis[(trifluoromethyl)sulfonyl] amide trifluoroacetate, 1-butyl-3-methyl-imidazolium hexafluorophosphate, 1-hexyl-3-methylimidazolium bis(trifluoromethylsulfonyl)imide, 1-butyl-3-methylimidazolium bis(trifluoromethylsulfonyl)imide, trihexyl(tetradecyl)phosphonium bis[oxalato(2-)]borate, 1-hexyl-3-methyl imidazolium tris(pentafluoroethyl)-trifluorophosphate, 1-butyl-3-methyl-imidazolium hexafluorophosphate, tris (pentafluoroethyl)-trifluorophosphate, trihexyl(tetradecyl) phosphonium, N"-ethyl-N,N,N',N'-tetramethylguanidinium, 1-butyl-1-methylpyrroledinium tris(pentafluoroethyl)trifluorophosphate, 1-butyl-1-methylpyrrolidinium bis(trifluoromethylsulfonyl)imide, 1-butyl-3-methyl imidazolium hexafluorophosphate, 1-ethyl-3-methylimidazolium bis(trifluoromethylsulfonyl)imide and 1-n-butyl-3-methylimidazolium.

The surface energy as defined by Thomas Young in 1805 is the interaction between forces of cohesion and forces of adhesion, thereby determining whether wetting or spreading of a liquid droplet on a surface occur. Surface energy can also be taken as the work required to increase the surface of a material by a defined area. Thus surface energy indicates the disruption of chemical bonds upon creation of a surface. Surfaces have to be less energetically favourable than a bulk phase, since otherwise surface energy would generate surfaces. Adhesion of matter is favoured if the free energy of adhesion at a given surface is negative. Generally, molecules at a surface tend to reduce free energy by interacting with other matter. Matter with the smallest difference of surface energy tends to undergo interactions with each other rather than with matter with a larger difference of surface energy, as such interaction is thermodynamically most stable. Accordingly, surfaces of matter of comparable surface energy attract each other. An illustrative example of a liquid is water, which is matter with high surface energy. While interactions of surfaces with liquids can generally be described using surface energy, interactions of other surfaces with water are typically described in terms of hydrophobicity, as water is one of most hydrophilic materials.

Hydrophobicity generally decreases with increasing surface energy. As an illustrative example, a hydrophilic surface such as glass has relatively high surface energy, while a hydrophobic surface such as a fluoropolymer (e.g. polytetrafluoroethylene) has a relatively low surface energy. It is noted in this regard that the same often applies for polar vs. non-polar surfaces. A correlation between surface polarity and surface energy is not disputed in the art and has recently been discussed by Giovambattista et al. (*J. Phys. Chem. B* (2007) 111, 9581-9587). However, a non-polar surface does not always have a lower surface energy than a polar surface. In this regard the above example of a perfluorocarbon compound, compared to a hydrocarbon compound, can also serve as an example in terms of surface energy. As observed above, a hydrocarbon compound is less polar than a perfluorocarbon compound, and the same holds for a perfluorocarbon surface vs. a hydrocarbon surface. However, a perfluorocarbon surface typically shows a lower surface energy than a hydrocarbon surface. Accordingly, the terms "polar" and "non-polar" differ from the terms "hydrophilic" and "hydrophobic", as noted above.

An illustrative example of a surface area of high surface energy is accordingly a, for instance predefined hydrophilic immobilisation area. Where other matter comes into contact with a hydrophilic immobilisation area, interactions with matter of comparable surface energy is typically preferred over interactions of matter that is of significantly different surface energy. Considering only the respective hydrophilic immobilisation area (and ignoring the residual surface area), this area thus rather undergoes interactions with matter of higher surface energy, such as hydrophilic matter, than with matter of lower surface energy—such as a less hydrophilic medium in the reservoir of the processing compartment. In the apparatus and method of the invention the liquid of the liquid droplet and the medium that is immiscible therewith compete to interact with a respective predefined immobilisation area. As far as the liquid droplet has a surface energy that is higher than the surface energy of the respective medium, the liquid droplet will interact with the predefined, in this example hydrophilic, immobilisation (surface) area since the predefined immobilisation area and the liquid droplet have a higher surface energy than the medium. As can be taken from this illustration, the surface energies of the liquid droplet, the immobilisation area and the medium need to be selected in an order that corresponds to the above generalisation that surfaces of higher surface energy preferably interact with each other. As an illustrative example, a liquid droplet of water with a surface energy of 72 dynes/cm may be provided. The predefined immobilisation area may have a surface energy of 24 dynes/cm (typical for a hydrocarbon). The medium may be a perfluorocarbon liquid with a surface energy of 18 dynes/cm. In this case, the water will interact preferably with predefined immobilisation area. As can be taken from this example, the order of the respective surface energies and not a difference between the matter used determines whether immobilisation of the liquid droplet can occur.

As a further illustration, a liquid droplet may for instance include or consist of toluene and the medium immiscible therewith may for instance be a perfluorocarbon liquid. If the predefined immobilisation area on the immobilisation member is a hydrophilic area, an interfacial interaction with toluene will occur rather than a respective interaction with the perfluorocarbon liquid, because the surface energy of toluene is higher than the surface energy of the perfluorocarbon liquid and furthermore the closer to the surface energy of such a hydrophilic area than that of the perfluorocarbon liquid.

It is recalled that in the method and apparatus of the present invention the immobilisation member includes not only a predefined hydrophilic immobilisation area, but also a remaining, i.e. residual, hydrophobic surface area. This remaining area is accordingly an example of an area of a lower surface energy when compared to the respective hydrophilic area. This residual area is accordingly (relatively) more hydrophobic when compared to the predefined immobilisation area. In the current example the residual surface area of the immobilisation member may thus be hydrophobic. When other matter such as a liquid droplet enters a system, where a surface with hydrophobic and hydrophilic areas is immersed in a medium, such other matter (e.g. the liquid droplet) could in theory interact with either the hydrophilic (immobilisation) area, the hydrophobic residual area or with neither of both. Upon contact of such introduced matter with the hydrophilic area and the hydrophobic residual area the occurrence or absence of interactions depends on certain aspects of the order of surface energy of the four relevant elements of the system: the surface energies of the hydrophilic area, of the hydrophobic area, of the medium and the introduced matter (e.g. the liquid droplet). For a given condition the occurrence of an interaction of a liquid droplet or other introduced matter with the hydrophilic immobilisation area firstly requires that the hydrophobic residual surface area has the lowest surface energy. Secondly the medium needs to have similar or higher surface energy compared to the hydrophilic immobilisation area, but lower surface energy than the liquid droplet or other introduced matter and the hydrophilic area. If these two conditions are fulfilled, interaction will occur only between e.g. a liquid droplet and a hydrophilic immobilisation area (i.e. surface area of higher surface energy). Finally, the liquid droplet (or other matter) and the hydrophilic surface have the highest surface energy (and are least hydrophobic) of the four relevant elements of the system. In this regard the relative surface energy and hydrophobicity between the introduced matter (such as a liquid droplet) and the hydrophilic immobilisation area is of no particular relevance.

Furthermore surfaces of high surface energy have a higher tendency to reduce energy by adsorption of matter. Thus even hydrophilic-hydrophobic interaction can occur, for instance between a hydrophilic glass surface and an organic solvent as illustrated above, when the medium is both hydrophobic and oleophobic (such as a perfluorocarbon liquid). Such phenomena can be defined as perfluorophobic-perfluorophobic interaction.

Summarizing the above, all conditions that have to be satisfied in the method and device of the invention, when expressed in terms of surface tension, can be simplified/illustrated as follows. It should be borne in mind in this context that 'more hydrophilic' (and typically 'less polar') also mean higher surface tension (cf. also above). 1. Droplet vs. Medium: Droplet>Medium which means the droplet is of higher surface tension than medium and is immiscible with the medium 2. Medium vs. hydrophobic area: the surface tension of the medium is greater or about the same (>≈) than that of the hydrophobic area. 3. Hydrophobic vs. (more) hydrophilic immobilisation area: the surface tension of the hydrophobic area is smaller than that of the more hydrophilic immobilization area. 4. Medium vs. hydrophilic immobilisation area: the surface tension of the hydrophilic area is greater than that of medium.

Surface energy can be quantified by measuring the contact angle (also termed wetting angle) between a droplet of a liquid such as water in thermal equilibrium on a horizontal surface, which is generally smooth and homogeneous, typically surrounded by a gas such as air. The contact angle thus also defines the wettability of a surface for a liquid (for an introduction into wetting and factors affecting the contact angle see e.g. Churaev, N. V., & Sobolev, V. D., *Advances in Colloid and Interface Science* (2007) 134-135, 15-23). The contact angle for water is an indication of the hydrophobicity of a surface as compared to other surfaces (see Gao, L., & McCarthy, T. J., *Langmuir* (2007) 23, 18, 9125-9127 for an example). A surface with a higher contact angle (with respect to water) can therefore generally be taken to be of higher hydrophobicity than a surface with a lower contact angle. It is understood that the surface geometry also affects the contact angle (see e.g. Jung, Y. C., & Bhushan, B., *Scripta Materialia* [2007] 57, 1057-1060; or Lundgren, M., et al., *Langmuir* [2007] 23, 1187-1194). In this respect, a person skilled in the art will be aware of the fact that for contact angles above 90° an increasing roughness of a surface typically increases the hydrophobicity. For contact angles below 90° an increasing roughness of a surface typically increases the hydrophilicity.

Depending on the type of surface and liquid, the droplet takes a certain shape upon contacting a surface as illustrated in FIG. 1B. A contact angle θ is given by the angle between the interface of the droplet and the horizontal surface. Such a contact angle θ is a thermodynamic variable that depends on the interfacial tensions of the surfaces involved. It reflects the balance of forces exerted by an attraction of molecules within the droplet to each other versus the attraction or repulsion those droplet molecules experience towards the surface molecules. The most commonly used technique of determining the contact angle is the so called static or sessile drop method. The measurement usually involves a successive addition of liquid droplets until a plateau in the contact angle is reached. The value at a respective plateau is called the advancing contact angle. A further value may be used to characterise a surface is the so called receding contact angle. It is obtained by measured when the contact point of a liquid droplet on a surface begins to change upon retracting the liquid of the droplet. The difference between advancing and receding contact angles can be taken as an indication as to the non-uniformity of the chemical and/or physical nature of a surface. Further means of determining the contact angle include the Wilhemly Plate method, the Captive Air Bubble method, the Capillary Rise method, and the Tilted-drop measurement. Where desired, the contact angle can be determined for a certain embodiment of the invention. Interference microscopy or confocal microscopy may be used, in particular with fluorescent droplets, or a combination of both methods. A respective combination technique has for example been described by Sundberg et al. (*Journal of Colloid and Interface Science* [2007] 313, 454-460).

A contact angle θ of zero results in wetting, while a contact angle θ between about 0 and about 90 results typically in spreading of the liquid droplet, in particular at values in the range below about 45 degrees. Contact angles θ greater than about 90 indicate the liquid tends to bead or shrink away from the solid surface. In some embodiments it may be desired to perform a simultaneous electrochemical and contact angle measurement. For this purpose a so called Wilhelmy balance is known in the art, which records the total force acting on a surface as the latter is being moved vertically (for further details see e.g. Wang, X., et al. *Langmuir* (2006) 22, 9287-9294).

Two further means of determining surface energy are atomic force microscopy and sum frequency generation, a vibrational spectroscopy method (see for example Opdahl, A., et al., *The Chemical Record* (2001) 1, 101-122).

The liquid droplet may include further matter, for example dissolved, emulsified or suspended therein. As an illustrative example, where an aqueous liquid is used, it may include one or more buffer compounds. Numerous buffer compounds are used in the art and may be used to carry out the various processes described herein. Examples of buffers include, but are not limited to, solutions of salts of phosphate, carbonate, succinate, citrate, acetate, formate, barbiturate, oxalate, lactate, phthalate, maleate, cacodylate, borate, N-(2-acetamido)-2-amino-ethanesulfonate (also called (ACES), N-(2-hydroxyethyl)-piperazine-N'-2-ethanesulfonic acid (also called HEPES), 4-(2-hydroxyethyl)-1-piperazine-propanesulfonic acid (also called HEPPS), piperazine-1,4-bis(2-ethane-sulfonic acid) (also called PIPES), (2-[Tris(hydroxylmethyl)-methylamino]-1-ethansulfonic acid (also called TES), 2-cyclohexylamino-ethanesulfonic acid (also called CHES) and N-(2-acetamido)-iminodiacetate (also called ADA). Any counter ion may be used in these salts; ammonium, sodium, and potassium may serve as illustrative examples. Further examples of buffers include, but are not limited to, triethanolamine, diethanolamine, ethylamine, triethylamine, glycine, glycylglycine, histidine, tris(hydroxymethyl)aminomethane (also called TRIS), bis-(2-hydroxyethyl)-imino-tris(hydroxymethyl)-methane (also called BIS-TRIS), and N-[Tris (hydroxymethyl)-methyl]-glycine (also called TRICINE), to name a few. The buffers may be aqueous solutions of such buffer compounds or solutions in a suitable polar organic solvent. As an illustrative example, a buffer may be deposited in solid form, for example freeze-dried. In such a case the solid buffer, e.g. a powder, may be dissolved in an aqueous phase by merging and or mixing, for instance assisted or performed by means of ultrasound. In such a case the amount of volume of a respective aqueous phase used may for instance be used to obtain the desired final buffer concentration.

Further examples of matter included in the liquid droplet include, but are not limited to, reagents, catalysts and reactants, for carrying out a chemical or biological process. As an illustrative example, salts, substrates or detergents may be added in order to maintain cells or proteins in an intact state. As a further illustrative example, chelating compounds may be required, for instance to protect organisms from traces of otherwise toxic salts or to increase the yield of a chemical reaction. As yet further illustrative examples, protease, RNase, or DNase inhibitors may be added in order to maintain proteins, RNA, or DNA in an intact state. A further example of a possible additive to a phase of the liquid droplet includes magnetically attractable particles (see above).

As yet a further illustrative example, magnetically attractable particles may be included in the liquid droplet. Such particles may be able to attract target matter. In some embodiments the magnetic particles can be functionalised with specific affinity for target matter and capturing target matter, therefore acting as a binding means (see below).

The droplet may be of any desired volume. It may for instance have a volume in the range of about 0.1 nl to about 50 µl, for instance about 1 nl to about 200 nl. In typical embodiments the droplet is of a volume of less than about 10 µl. The skilled artisan will be aware that when using a droplet of large volume (such as e.g. 10 µl or 50 µl), the respective droplet may split into smaller droplets when contacting a medium. Where such splitting is undesired, suitable volumes for a droplet of a selected liquid can easily be determined experimentally.

In some embodiments the invention the liquid of the droplet is of lower density than the medium that is immiscible with the liquid droplet. In these embodiments the respective droplet floats on the surface of the medium once disposed therein. In other embodiments of the invention the liquid of the droplet is of higher density than the respective medium. In these embodiments the respective droplet sinks into the medium once disposed therein.

The apparatus of the invention furthermore includes a processing compartment. The processing compartment is defined by a reservoir and an immobilisation member. The immobilisation member is designed to immobilise a liquid droplet in the processing compartment (cf. below, cf. e.g. FIG. 1 for an illustration). The reservoir is defined by a circumferential wall and a base. The circumferential wall together with the base also determines the shape of the reservoir (cf. e.g. FIGS. 2A-2C). In some embodiments the immobilisation member is attached to the circumferential wall of the reservoir and defines a pocket where an immiscible liquid can be stored along with sample droplets.

The circumferential wall and the base of the reservoir may include or consist of any desired material. Typically, the circumferential wall and the base are solid and do not interfere with the processing of a biological and/or chemical sample that is performed or desired to be carried out therein. The circumferential wall and the base of the reservoir may for instance include an organic, inorganic or metallic substrate, such as plastic—for instance a perfluorocarbon polymer, a hydroperfluorocarbon polymer, glass, quartz, silicon, anodized aluminium, or stainless steel. The inner surface of the circumferential wall and the base of the processing compartment, in the following also commonly addressed as "the inner walls", consist in some embodiments of exactly the same material. They may also consist of, or at least include, the same material as the immobilisation member. In other embodiments the respective material of the circumferential wall includes the same or at least similar components as the base and/or the immobilisation member, but for instance in different amounts or ratios. In yet other embodiments at least one of the circumferential wall, the base and the immobilisation member include additional or completely different material. In further embodiments the circumferential wall and the base are of entirely different material. In one of these embodiments the immobilisation member is of yet a further entirely different material.

The inner walls of the processing compartment may possess any internal surface characteristics, as long as they allow for the accommodation of a desired medium that immiscible with the liquid droplet. The terms "accommodate", "accommodation" and "accommodating" as used herein refer both to receive and receiving matter and to have, to house or harbour, or having, housing and harbouring matter, and includes the capability or being capable to allow the respective presence of matter. The inner walls may thus for instance be of any surface energy. They may for example be either hydrophilic or hydrophobic. Furthermore, inner walls of the processing compartment may provide different surface characteristics. Thus, some inner walls or wall-portions, may for example be hydrophilic, while others may be hydrophobic.

Any part of the inner walls of the reservoir may also be treated in such a way that they provide a desired surface energy, such that they for instance provide respective hydrophilic or hydrophobic surface characteristics. A respective treatment may for instance be desired in order to provide a surface that possesses altered, e.g. reduced or negligible, interactions with the liquid of a selected liquid droplet. For example the base region of the reservoir may be treated respectively. In some embodiments the inner walls of the reservoir are furthermore inert against the medium that is desired to be accommodated therein. Such embodiments allow for multiple reusing of the device. An illustrative example of a material that is inert against most corrosive media is a fluoropolymer such as fluoroethylenepropylene (FEP), polytetrafluoroethylene (PFTE, Teflon), ethylene-tetrafluoroethylene (ETFE), tetrafluoroethylene-perfluoromethylvinylether (MFA), vinylidene fluoride-hexafluoropropylene copolymer, tetrafluoroethylene-hexafluoropropylene copolymer, vinylidene fluoride-hexafluoropropylene-tetrafluoroethylene terpolymer, perfluoromethyl vinyl ether-tetrafluoroethylen copolymer, perfluoroalkoxy copolymer (PFA), poly(vinyl fluoride), polychlorotrifluoroethylene, fluoro-silicones, or fluorophosphazenes.

The processing compartment may be of any desired form and volume. In some embodiments it may for example be designed or adapted to provide a volume that limits the freedom of movement of a droplet disposed therein. In such an embodiment the volume of the reservoir may for instance be of about 1 nl to about 500 ml, or a volume of about 100 nl to about 10 µl. In other embodiments the reservoir may be designed or adapted to be capable of accommodating large quantities of droplets at the same time. In such an embodiment the volume of the reservoir may for instance be of about 0.1 ml to about 500 ml, or a volume of about 1 ml to about 100 ml. Where a medium is filled into reservoir, only a part of the volume of the reservoir may be filled with the respective medium. The remainder of the reservoir may for instance be occupied by other media, such as a fluid, for instance air or an inert gas.

The processing compartment may be dismountable or include or consist of parts that can be assembled to form a processing compartment when required. In some embodiments the base is removably connected to the circumferential wall as for instance depicted in FIG. 17. In some embodiments a carrier-frame and a base can be assembled to define a processing compartment. A respective carrier frame is designed to match the base, such that a reservoir can be formed, i.e. such that the processing compartment is designed to be capable of accommodating a medium. The carrier frame has a central passage defined by a circumferential wall. Upon assembly to the processing compartment this circumferential wall becomes the circumferential wall of the processing compartment. In some embodiments the base may be adhered or glued to the carrier frame upon assembly. The base may be any element or device that is of a suitable geometry and size to cover the central passage of the carrier frame and to define a reservoir as explained above. In some embodiments the base may be identical with the immobilisation member. In such embodiments the immobilisation member may be, for instance removably, attached to the carrier frame.

The apparatus of the invention can in some embodiments also be taken to include an immobilisation member, and a carrier-frame, wherein the carrier-frame includes a central passage defined by a circumferential wall. Following this conception, the immobilization member is in some of such embodiments removably arranged on the first side of the central passage of the carrier-frame. The second side of the central passage of the carrier-frame may in some embodiments define an opening. In other embodiments a further element or device, such as an inlet member, may be—for instance removably—arranged on the second side of the central passage of the carrier-frame. Accordingly, the carrier-frame and the immobilization member are arranged to define a processing compartment.

As already indicated above, besides the reservoir the processing compartment also includes an immobilisation member. The immobilisation member, which is arranged within the reservoir, may be located anywhere within the reservoir. The immobilisation member may also have any desired orientation within the reservoir. It may for example be arranged in any angle relative to the surface of a medium inserted into the processing compartment. It may for instance be inclined to a desired degree relative to the surface of a medium. In some embodiments a part of the immobilisation member may also protrude from the reservoir, as long as the predefined immobilisation area included in its patterned surface (see below) is arranged within the reservoir. In other embodiments the processing compartment of the apparatus is capable of receiving a respective immobilisation member in its entirety (cf. e.g. FIG. 2C). Such embodiments may for instance be selected where the processing compartment is desired to receive or accommodate a liquid. Accordingly, in such embodiments the immobilisation member will be entirely immersed in a medium, once the processing compartment has received and accommodates the latter. In some of these embodiments the processing compartment provides a separate inlet for a respective immobilisation member to be placed into the processing compartment. Some embodiments may allow for a respective immobilisation member to be immersed in several reservoirs or apparatuses at the same time, by for instance providing corresponding sealable openings in each reservoir/apparatus. In one embodiment a respective immobilisation member may be moved from one reservoir/apparatus to another one. In this context it will be understood that the apparatus and method of the present invention do generally not require a transfer of a sample from one reservoir to another.

The immobilisation member may, for instance, be arranged on a top of the base of the reservoir or be an integral part of this base. In some embodiments the immobilisation member is an integral part of the apparatus. It may for instance project from a circumferential wall or the base of the processing compartment. In other embodiments the immobilisation member is removably arranged in the apparatus. In such embodiments the immobilisation member may also be designed to match a frame. Such a frame may for example assist in fixing or securing the immobilisation member within the reservoir. In some embodiments the immobilisation member is removable from the device that provides the reservoir. Providing the apparatus may in such embodiments include providing a device that includes a reservoir that is capable of receiving an immobilisation member, providing a respective immobilisation member, and disposing the immobilisation member into the reservoir, thus forming the processing compartment of the apparatus.

The terms "on top" and "on a top of" as used herein, refer to a position where the apparatus of the present invention is held in such a way that the base is oriented in the direction of gravity. In this position the apparatus would, under the influence of gravity, fall in the direction to which the base is orientated. In some embodiments this position reflects an orientation of the apparatus, where any inlet member or cover is oriented away from the direction of gravity and/or in which the apparatus can be placed onto a flat surface.

The circumferential wall of the reservoir, which forms the processing compartment once the immobilisation member is provided therein, is in some embodiments designed or adapted to support the immobilisation member. In such embodiments the position of the immobilisation member may be determined by the respective design of the circumferential wall. The circumferential wall may for instance include a support dent or a reception recess that are suitable for supporting the immobilisation member. As a further example, the circumferential wall of the reservoir may be extending into the interior of the processing compartment, thereby forming a step, by which the immobilisation member can be supported. In such embodiments the step may be designed or located to provide a distance to the base that prevents direct contact between the base and the immobilisation member. In such embodiments the processing compartment includes a space between the base and at least a part of the immobilisation member.

Figure 2B:
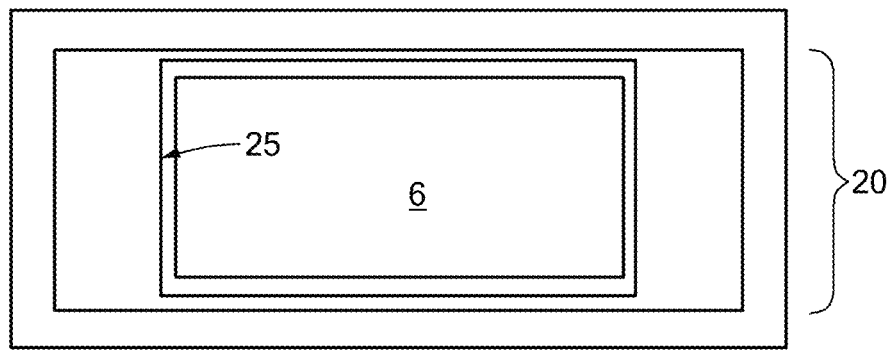

FIG. 2A depicts an example of a respective circumferential wall that is designed or adapted to support a biochip as an immobilisation member by means of a step (see also FIG. 2B and cf. FIG. 1C). Once the biochip is inserted into the reservoir (cf. e.g. FIG. 2G) and supported by the circumferential wall, the processing compartment is assembled (see FIG. 2C). In other embodiments the circumferential wall of the reservoir is designed or adapted to support the immobilisation member without providing a distance between the base and the immobilisation member. In some of these embodiments a space within, or a part of, the processing compartment may be separated from the residual processing compartment. As an illustrative example, the immobilisation member may include a hollow space at its lower end. In some of these embodiments the immobilisation member may provides at least a part of the circumferential wall of the processing compartment. In some of these embodiments the physical separation may allow for several processing compartments to be present within the same apparatus (cf. e.g. FIG. 4F). In some embodiments the apparatus of the invention includes or is adapted to include a plurality, such as two, three or more, immobilisation members. Respective immobilisation members may be patterned in the same, a similar or a different way and include (immobilisation) surface areas with the same, similar or different surface energies. The reservoir may for instance be designed to be capable of receiving a plurality of immobilisation members.

The immobilisation member may be of any shape and any material. It may for instance be a plate, a brick or a disk (cf. also below). Examples of materials, which may be included in such an immobilisation member, include, but are not limited to, a metal, quartz, glass, silicone, a plastic, a polymer, a ceramic, an insulator, a semiconductor, organic material, inorganic material and composites thereof. Like the base of the apparatus, the surfaces of the immobilisation member may include the same and/or different material as the remainder of the immobilisation member. Furthermore, the surfaces of the immobilisation member may possess any surface characteristics, as long as they allow for receiving or the accommodation of the immobilisation member in a desired medium (cf. above). The surface of the immobilisation member, or a part thereof, may for example be concave or convex rounded or a combination thereof. The patterned surface of the immobilisation member (see below), including the predefined immobilisation area(s) included therein, is in some embodiments at least essentially flat. In one embodiment all surfaces of the entire immobilisation member are at least essentially flat. Furthermore, different areas of the surface of the immobilisation member may provide different surface characteristics. As an illustrative example, some areas on the surface may be rendered rough, while other areas may be rendered at least essentially smooth.

As explained in detail below, the immobilisation member includes a surface, for example, but not limited to a hydrophobic surface, including for example a superhydrophobic surface of for instance a contact angle for water of more than 150°. The making of superhydrophobic surfaces has for instance been reviewed by Ma & Hill (*Current Opinion in Colloid & Interface Science* [2007] 11, 193-202) or by Li et al. (*Chem. Soc. Rev.* [2007] 36, 1350-1368). Compounds and other matter listed in this review are generally suitable materials for selected surface areas of the immobilisation member of the apparatus of the invention. This surface is patterned in such a way that it includes at least one predefined immobilisation area, for instance a hydrophilic immobilisation area. Such surface patterning may for example be obtained by a surface treatment. A treatment that may be carried out to alter surface characteristics may include various means, such as mechanical, thermal, electrical or chemical means. A method that is commonly used in the art is a treatment with chemicals having different levels of affinity for the liquid sample. As an example, the surface (or a part thereof) of plastic materials can be rendered hydrophilic via treatment with dilute hydrochloric acid or dilute nitric acid. As another example, a polydimethylsiloxane (PDMS) surface can be rendered hydrophilic by an oxidation with oxygen or air plasma. As a further example, the surface properties of any hydrophobic surface can be rendered more hydrophilic by coating with a hydrophilic polymer or by treatment with surfactants. Examples of a chemical surface treatment include, but are not limited to exposure to hexamethyldisilazane, trimethylchlorosilane, dimethyldichlorosilane, propyltrichlorosilane, tetraethoxysilane, glycidoxypropyltrimethoxy silane, 3-aminopropyltriethoxysilane, 2-(3,4-epoxy cyclohexyl)ethyltrimethoxysilane, 3-(2,3-epoxy propoxyl)propyltrimethoxysilane, polydimethylsiloxane (PDMS), γ-(3,4-epoxycyclohexyl)-ethyltrimethoxysilane, poly(methyl methacrylate), a polymethacrylate co-polymer, urethane, polyurethane, fluoropolyacrylate, poly(methoxy polyethylene glycol methacrylate), poly-(dimethyl acrylamide), poly[N-(2-hydroxypropyl)methacrylamide] (PHPMA), α-phosphorylcholine-o-(N,N-diethyldithiocarbamyl)undecyl oligoDMAAm-oligo-STblock co-oligomer (see Matsuda, T et al., *Biomaterials* (2003), 24, 4517-4527), poly(3,4-epoxy-1-butene), 3,4-epoxycyclohexylmethylmethacrylate, 2,2-bis [4-(2,3-epoxy propoxy)phenyl]propane, 3,4-epoxycyclohexylmethylacrylate, (3',4'-epoxycyclohexylmethyl)-3,4-epoxycyclohexyl carboxylate, di-(3,4-epoxycyclohexylmethyl)adipate, bisphenol A (2,2-bis-(p-(2, 3-epoxy propoxy)phenyl)-propane) or 2,3-epoxy-1-propanol. Both surfaces areas of low and high surface energies, e.g. a hydrophobic surface and a hydrophilic surface area included therein, may be obtained by patterning a surface with different coating agents.

As an illustrative example, European patent application EP 1 683 571 discloses the use of a hydrophobic group-containing silane compound and a hydrophilic group-containing silane compound. Other illustrative examples of hydrophilic-hydrophobic micropatterns that can be used in the present invention are silica pattern on a titania surface which are obtained by photolitography as described by Kanta et al. (*Langmuir* [2005] 21, 5790-5794), followed by silica coating and subsequent heat exposure. Other illustrative examples includes method of manufacturing hydrophobicity difference patterns by irradiating fluoroalkylsilane coated glass in the presence of an additional titanium oxide coated glass plate as described in Japanese patent application 2005-003803. A further illustrative example of suitable micropatterns is described in International Patent Application WO 2006/046699. In this reference a surface with silicon-hydrogen bonds is generated and then reacted in desired areas with a water-repellent compound in a hydrosilylation reaction, while in other areas this surface is reacted to a hydrophilic area.

Any part of the patterned surface of the immobilisation member may be selected as the respective predefined surface area. The predefined immobilisation area is of a higher surface energy than the medium that is immiscible with the liquid of the liquid droplet. As an illustrative example, the predefined immobilisation area may be characterised by an advancing contact angle for water that is at least about 5° or about 10° lower than the advancing contact angle for water of the respective medium. Furthermore the respective predefined surface area is of a higher surface energy than the residual surface. The predefined immobilisation surface area may, for example, be characterised by an advancing contact angle for water that is at least 5°, for example 10° lower than the advancing contact angle for water of the residual surface. In contrast thereto, the residual surface of the immobilisation member is of about the same or a lower surface energy than the medium. The residual surface area is furthermore of a lower surface energy than the predefined immobilisation surface area. The medium, which is thus of about the same or a higher surface energy than the residual surface area, is in turn of a lower surface energy than the liquid of the liquid droplet (see also above and below).

The remaining area of the patterned surface, which may be of any desired dimension, is of at most about the same surface energy as said medium or is of a lower surface energy. Accordingly, the residual area of the patterned surface is generally of a lower surface energy than the liquid of the liquid droplet. As an illustrative example, the residual area of the patterned surface may be a hydrophobic surface area. In some embodiments the residual (i.e. remaining) area of the patterned surface is water-repellent.

As an example, a surface of the immobilisation member may be treated in such a way that it provides respective wettability surface characteristics (cf. above). The residual surface of the immobilisation member, i.e. the surface area not corresponding to the predefined immobilisation area of the immobilisation member is an area of the patterned surface of the immobilisation member that is of at most a comparable surface energy as the medium that is immiscible with the liquid of the liquid droplet. This surface area is in these cases typically of at most about the same surface energy as a respective medium. In embodiments where the immiscible medium, which is intended to be filled into the reservoir (see below), is a hydrophobic medium, a respective surface is in these cases of at least about the same hydrophobicity as a hydrophobic medium. The residual surface area may for instance be a hydrophobic surface area. As noted above, the respective residual surface area is generally of a lower surface energy than the liquid of the liquid droplet.

In typical embodiments the residual surface area, i.e. the area differing from the predefined immobilisation area of the patterned surface, is of such a low wettability for the liquid of the liquid droplet that a low affinity to the liquid of a droplet results. A respective low affinity of the liquid of the liquid droplet to the residual surface area occurs in the presence of a medium that has a surface energy that is (i) similar or higher than that of the hydrophilic immobilisation area and (ii) lower than that of the liquid droplet (supra). Such a low affinity to the liquid of a droplet is characterised in that no permanent immobilisation of the liquid droplet occurs, as illustrated in FIG. 1A. The surface may for instance be of such low affinity to the liquid of the droplet that the maximal force, which the affinity of the material is capable of exerting on the droplet in a medium in the reservoir of the apparatus (cf. below), is below the force exerted by the buoyancy force or by gravity. Accordingly, hardly any or no interaction between the residual (differing from the predefined) immobilisation surface area and a respective droplet is detectable. In some embodiments the liquid droplet may be repelled from the residual surface area of the patterned surface of the immobilisation member.

Where desired, the residual surface of the immobilisation member may include a material that is inert against most corrosive media and at the same time is of such low affinity to the liquid of the droplet that the maximal force, which the affinity of the material is capable of exerting on the droplet in said medium, is below the buoyancy force or respectively gravitation. Such embodiments allow for multiple reusing of the immobilisation member. An illustrative example of such a material is a fluoropolymer such as fluoroethylenepropylene (FEP), polytetrafluoroethylene (PFTE) ethylene-tetrafluoroethylene (ETFE), tetrafluoroethylene-perfluormethylvinylether (MFA), or perfluoroalkoxy copolymer (PFA).

As an illustrative example, a method of providing an immobilisation member with a patterned surface is briefly described in the following. In this example, an immobilisation member with a surface of any desired properties may be provided. The surface may for instance be of any shape and material, as long as it is capable of accommodating a photocatalytic matter and oxidisable matter, and as long as it is compatible with the selected conditions for depositing and irradiating (see below). Photocatalytic matter such as titanium oxide may be used for patterning, in the following also abbreviated as $TiO_x$ (in which x is typically 1 or 2), for example titanium dioxide, $TiO_2$ (in e.g. anatase or rutile forms). Such photocatalytic matter may be deposited onto the surface of the immobilisation member by any means. It may for example be deposited by flame hydrolysis deposition (FHD), plasma enhanced chemical vapour deposition (PECVD), inductive coupled plasma enhanced chemical vapour deposition (ICP-CVD), the sol-gel method or sputtering. In some embodiments the photocatalytic matter is deposited by means of the sol-gel process. As an illustrative example, a titanate sol may be generated by hydrolysis of tetrabutyl-titanate or tetrapropyl-titanate. Any suitable protocol, such as sol-gel protocols using acid-catalysed, base-catalysed and two-step acid-base catalysed procedures may be followed. As a further example, the photocatalytic matter may be deposited by means of chemical vapour decomposition.

Oxidisable matter may then be deposited onto the surface of the immobilisation member, for example in form of a film. A respective film may for example be a monolayer. Suitable methods for depositing include, but are not limited to, microcontact printing, microfluidic patterning, microfluidic lithography, cleaved edge overgrowth, or shadowed evaporation may be used.

The oxidisable matter used in such cases is of a surface energy that differs from the surface energy of the photocatalytic matter. As a result, the wettability of these two matters differs. As an illustrative example, the oxidisable matter may be characterised by an advancing contact angle (see below) for water that is at least 5° higher or 5° lower than the advancing contact angle for water of the photocatalytic matter. As an example, the oxidisable matter may have an advancing contact angle for water that is 10° higher than the advancing contact angle for water of the photocatalytic matter. As a further example, the oxidisable matter may have an advancing contact angle for water that is 10° lower than the advancing contact angle for water of the photocatalytic matter. The oxidisable matter may for example be hydrophobic. Examples of suitable oxidisable matter include, but are not limited to, a wax, a fat, an oil, a fatty acid, a silane, a siloxane, a perfluoroalkane, a silazane, a stannane, a polymer and a composite of a polymer and inorganic particles.

As yet another example, a mask, such as a photomask, may be used both when patterning the surface of the substrate and/or when depositing photocatalytic matter, e.g. by means of sputtering (see above). A respective mask may cover the residual surface of the substrate, thus preventing the deposition of photocatalytic matter thereon. A method of such an embodiment may include first covering the residual surface of the substrate with a mask and subsequently depositing the photocatalytic matter on the surface. Thereby photocatalytic matter is deposited only on the predefined immobilisation surface area of the immobilisation member.

Furthermore, in this example the entire surface, or at least the patterned surface, of the immobilisation member may be exposed to electromagnetic radiation. The electromagnetic radiation may be of any intensity and the exposure of any length as long as it is sufficient to render the photocatalytic matter capable of catalysing the oxidation of the selected oxidisable matter. The required exposure time will typically depend on the power of the electromagnetic radiation used. In typical embodiments where UV light is used as electromagnetic radiation, the energy density is of at least 50 mJ/cm$^2$, such as for example of at least 100 mJ/cm$^2$. Accordingly, the photocatalytic matter catalyses the oxidation of such oxidisable matter that is in contact therewith.

As a result, oxidisable matter that is in contact with photocatalytic matter is removed from the at least one predefined immobilisation surface area. Accordingly, only the residual area of the surface retains, at least essentially, the wettability provided by the oxidisable matter. As an illustrative example the residual area of the surface remains hydrophobic in embodiments where hydrophobic oxidisable matter is used. In contrast thereto, the photocatalytic matter in the plurality of surface areas is being exposed. This is due to the fact that exposing the surface to electromagnetic radiation shows little or no impact on the oxidisable matter that is not in contact with the photocatalytic matter. In the absence of matter with the catalytic properties described above, oxidation, including degradation of the oxidisable matter by electromagnetic radiation is very slow, so that, if at all, marginal or insignificant effects on the oxidisable matter are observed.

As a further example, direct writing may be used to form a patterned surface, for example in the form of a micro- or nanoelectrochemical reaction to form oxide dots on a metal surface (Mardare, A. I., et al. *Electrochimica Acta* [2007] 52, 7865-7869). As another example, the surface of an immobilisation member may covered with a coating, such as a coating of a functionalized polymer, on which a pattern may be formed by nanoimprinting lithography. Following etching of the remaining polymer, polymer brushes of a desired wettability (e.g. hydrophilic or hydrophobic brushes) may be grown thereon as described by Genua et al. (*Nanotechnology* [2007] 18, 215301). As yet another example, hydrophilic patterns may be formed on a hydrophobic surface of an immobilisation member by means of writing using a dielectric barrier discharge microplasma jet as described by West et al. (*Lab on a Chip* [2007] 7, 981-983). As yet a further example, dewetting with the microcontact printing technique, e.g. of film of polydimethylsiloxane on the immobilisation member with a stamp having a film of octadecyltrichlorosilane in a solvent (Benor, A., et al., *Journal of Vacuum Science & Technology B* [2007] 25, 4, 1321-1326), may be used to obtain a patterned surface.

By avoiding significant interactions between the droplet and the residual surface of the immobilisation member with at most about the same surface energy as the medium, the immobilisation of the liquid droplet on a selected immobilisation area of the surface of the immobilisation member is facilitated. The selected immobilisation area is designed to fix and immobilise the droplet in the processing compartment. This selected immobilisation area is provided by the patterned surface of the immobilisation member, in that the surface is patterned in such a way that it includes at least one predefined immobilisation area, such as a hydrophilic area. As explained below, typically an attraction occurs between the liquid of the liquid droplet and the surface of the predefined area, since the latter is typically of higher surface energy than the residual surface.

It is understood that any desired means and method may be used to obtain a patterned surface as described above on the immobilisation member of the apparatus of the invention. Where desired, further matter may be disposed on a selected area of the patterned surface, such as the predefined immobilisation area. As an illustrative example, a hydrogel may be formed on the predefined immobilisation area by disposing a pregel-solution and subsequent spin-coating as described by Jakobs and Hanein (*Colloids & Surfaces A: Physiochem. Eng. Aspects* (2006) 290, 33-40).

This predefined immobilisation area may have any shape, size and geometry as long as it is of such a texture, e.g. roughness and waviness, that the liquid droplet remains intact upon being contacted therewith, and can be immobilised on the immobilisation member. The term "intact" refers to the existence of a defined droplet, which may take various shapes according to the surface characteristics of the predefined area (see e.g. FIG. 1B). The liquid droplet is thus understood to remain intact, while it is for instance spread to a desired extend, or merged with another droplet. The predefined immobilisation surface area may for example be flat or at least essentially flat, concave or convex rounded (cf. FIG. 3, right hand side) or a combination thereof. Examples of respective shapes of a hydrophobic surface area include, but are not limited to, the shape of a circle, an egg, letters X or Y, a triangle, a rectangle, a square, or any oligoedron. As an illustrative example, the predefined surface area may be of circular shape. In such embodiments a respective circular area may for instance be of a diameter selected in a range of about 1 µm to about 10 mm, such as a range of about 10 µm to about 8 mm or a range of about 100 µm to about 5 mm.

The immobilisation member may before, during or after disposing a liquid droplet on the predefined immobilisation surface area have any orientation relative to the ground. In embodiments where an essentially flat surface is provided and the liquid droplet is handled in a gas such as air, it may for convenience be desired to dispose the liquid droplet on top of the respective surface. As a further example, in embodiments where an immobilisation member with a concave or convex surface is provided and the liquid droplet is handled in a gas such as air, it may for instance for convenience be desired to pattern the surface thereof in such a way that the liquid droplet can be disposed at a top or bottom position of a dent, relative to the direction of action of gravitation.

The predefined immobilisation area is of a sufficient wettability and sufficient width in the plane of the surface to allow the immobilisation of the liquid droplet on the predefined immobilisation area via interfacial interactions, at least once a medium that is immiscible with the liquid droplet has been filled into the reservoir. The respective interfacial interactions may be or include any form of interaction. Such interactions may for instance be or include attractions, such as non-covalent forces that result in an overall attraction of the liquid of the liquid droplet to the respective surface area. Examples of respective interfacial interactions include, but are not limited to hydrophilic-hydrophilic (such as polar), hydrophobic-hydrophobic, oleophilic-oleophilic and perfluorophobic-perfluorophobic interactions. Non-covalent short- to long-range macroscopic scale interactions between different surfaces include, but are not limited to, Lifshiz-van der Waals attractions, electrical double layer repulsion and electron-acceptor/electron-donor interactions (for an overview see e.g. van Oss, C. J., *J. Mol. Recognit.* (2003) 16, 177-190).

Accordingly, upon contacting the predefined immobilisation area, the liquid droplet is immobilised on the immobilisation member, as illustrated in FIG. 1B. The predefined immobilisation area thus prevents a liquid droplet from spontaneously detaching from the immobilisation member and for instance floating through the reservoir, sinking to the base thereof, or ascending to the surface of a respective medium included therein. In some embodiments the predefined immobilisation (surface) area is of such a high wettability for the liquid of the liquid droplet and of such a width in the plane of the surface of the immobilisation member that the maximal force, which the interfacial interactions are capable of exerting on the droplet in the medium that is immiscible with the liquid droplet, is higher than the buoyancy force. In some embodiments the wettability of the predefined immobilisation (surface) area for the liquid of the liquid droplet, and its width in the plane of the surface of the immobilisation member are so high that the respective maximal force is higher than a Bernoulli force (flow force) exerted by the medium. The Bernoulli force may for instance be generated upon moving the immobilisation member, moving the reservoir or moving the entire apparatus. In some embodiments the predefined immobilisation (surface) area is of such a high respective wettability and width that the maximal force, which the interfacial interactions are capable of exerting on the droplet in the respective medium, is higher than the force exerted by the medium upon rinsing the immobilisation member therewith. Accordingly in such embodiments the respective wettability and dimension of the immobilisation area are stronger than the forces acting on an immobilised droplet that are caused by the movement of medium during rinsing (e.g. shear forces, flow forces).

Besides including the predefined immobilisation area within the patterned surface, the immobilisation member may include other devices or components such as for instance a barcode-area or a handle.

In some embodiments of the invention, the apparatus provides a plurality of predefined immobilisation areas, for example as described above. Any arrangement of predefined immobilisation areas within the patterned surface may be chosen in such an embodiment. In one embodiment all predefined immobilisation areas are identical (cf. e.g. FIG. 1C or FIGS. 2D-2F). In such an embodiment several droplets of the same diameter and for instance also of the same liquid may be used with the apparatus at the same time. In another embodiment several predefined immobilisation areas may be provided that differ in their shape or in their width in the plane of the surface of the immobilisation member. Predefined immobilisation areas of a respective plurality may also differ in their surface properties, such as their hydrophilicity.

As already noted, the apparatus of the present invention as described above is furthermore adapted to accommodate a medium. The medium is immiscible with the liquid droplet (supra). It is furthermore of a lower surface energy than the liquid of the liquid droplet (see above). As an illustrative example, the medium may be a hydrophobic medium. The medium may for example be a fluid, such as for instance a liquid. As an illustrative example of a respective liquid, where the liquid contained in the droplet is water, a suitable immiscible liquid is octane. As a consequence, the droplet does not dissolve in the respective liquid, if disposed therein. Accordingly, the liquid droplet remains intact once inserted into the respective medium. In some embodiments the position of the immobilisation member remains unchanged upon disposing a respective medium into the processing compartment or upon removing the medium from the processing compartment. In some embodiments gravity or buoyancy force in the medium may assist in positioning the immobilisation member in the reservoir or in fixing the immobilisation member in its position.

Further examples of a suitable medium, including a liquid, in embodiments where the liquid of the droplet is or includes water include, but are not limited to, a mineral oil, a silicone oil, a carbonic acid (such as oleic acid), triolein, soybean oil, a hydrocarbon compound (such as e.g. hexadecane or tetradecane), a hydroperfluoro carbon compound, a perfluoro-carbon compound or an ionic liquid such as 1-n-butyl-3-methylimidazolium hexafluorophosphate [BMIM][PF$_6$] (see e.g. Wang, W.-H., *Langmuir* (2007) 23, 11924-11931). A perfluoro-carbon (PFC) compound is a perfluorinated, i.e. a fully fluorine-substituted carbon compound. A hydroperfluorocarbon compound is a partly fluorinated hydrocarbon compound, i.e. a fluorine- and hydrogen-substituted carbon compound. Perfluorocarbon and hydroperfluoro-carbon compounds consist of straight- or branched alkyl chains and/or rings, which may contain one or more unsaturated carbon-carbon bonds, as well as aromatic moieties. The chain/ring of a perfluorocarbon compound may contain heteroatoms, i.e. atoms that differ from carbon. Examples of such heteroatoms include, but are not limited to, O, N, S and Si.

Numerous perfluorocarbon and hydroperfluoro carbon compounds are known in the art. Examples of perfluorocarbon compounds include, but are not limited to, docosafluorodecane [Chemical Abstract No 307-45-9], dodecafluoro-pentane [CAS No 678-26-2], 1,1,1,2,2,3,3,4,4,5,5,6,6,7,7,8,8-heptadecafluoro-octane [CAS No 335-65-9], perfluorodecalin [CAS No 306-94-5], tetratriacontafluoro-hexadecane [CAS No 355-49-7], n-perfluorohexane, 1,1,1,2,2,3,3,6,6,7,7,8,8-tetradecafluoro-4-octene [CAS No 3910-82-5], 1,1,2-trihydroperfluoro-1-decene [CAS No 21652-58-4], 1,1,2-trihydroperfluoro-1-octene [CAS No 25291-17-2], 1,1,1,2,2,3,3,4,4,5,5,6,6,7,7,8,8-heptadecafluoro-decane [CAS No 77117-48-7], 1,1,1,2,2,3,3,4,4-nonafluoro-6-pentadecene [CAS No 118202-35-0], 8,8,9,9,10,10,11,11,12,12,13,13,14,14,15,15,15-heptadecafluoro-5-pentadecene [CAS No 118642-83-4], 2,2,3,3,4,4,5-heptafluorotetrahydro-5-(nonafluorobutyl)-furan [CAS No 335-36-4], and 4-[difluoro(undecafluorocyclohexyl)methyl]-2,2,3,3,5,5,6,6-octafluoro-morpholine [CAS No 132252-23-4], 1,1,2,2,3,3,3-heptafluoro-N,N-bis(heptafluoropropyl)-1-propanamine [CAS No 338-83-0], to name a few. Examples of hydroperfluoro carbon compounds include, but are not limited to, 2,2,3,3-tetrafluoro-hexane [CAS No 83225-48-3], 1,1,1,2,2,3,3-heptafluoropentane [CAS No 754-68-7], 1,1,1,2,2,3,3-heptafluoro-nonane [CAS No 755-89-5], 1,2,3,4,5,6-hexafluoro-cyclohexane [CAS No 22060-80-6], trifluoromethyl-benzene [CAS-No 98-08-8], 1,2,3,4-tetrafluoro-naphthalene [CAS No 711-55-7], 1,1'-oxybis[3,3,4,4,5,6,6,6-octafluoro-5-(trifluoromethyl)-hexane [CAS No 220469-12-5], to name only a few.

Additionally, and in particular where the liquid of the liquid droplet is water, the liquid of the liquid droplet or the medium that is immiscible therewith may include an ionic or non-ionic surfactant, for example a perfluorocarbon-surfactant. Typically the surfactant adsorbs primarily at the solid-liquid and liquid-liquid and liquid-vapour interfaces near the contact line region, where applicable. As an illustrative example, it may be desired to use a surfactant in order to reduce non-specific interactions of a sample included in the inner phase of the fluid droplet with a surface. It is noted in this regard that non-ionic surfactants often alter contact angles, with high contact angles above 90° typically being reduced (see e.g. Churaev & Sobolev, 2007, supra). Numerous surfactants, which are partly hydrophilic and partly lipophilic, are used in the art, such as for instance alkyl benzene sulfonates, alkyl phenoxy polyethoxy ethanols, alkyl glucosides, secondary and tertiary amines such as diethanolamine, Tween, Triton 100 and triethanolamine, or e.g. fluorosurfactants such as ZONYL® FSO-100 (DuPont).

Accordingly, the method of the present invention may for instance include providing a surfactant and disposing the surfactant into the reservoir such that it is able to contact the medium and dissolve therein. Any surfactant may be used. Typically the surfactant will be selected according to the medium in the processing compartment and the liquid of the droplet, since surfactants accumulate at surfaces. The surfactant may for instance be selected to lower the surface tension of the liquid of the droplet and/or where the medium is also a liquid, the surface tension of the respective liquid in the processing compartment. It may also be selected to lower or minimize interactions between the medium in the processing compartment and the inner walls thereof, such as the base or the circumferential wall(s). Typically the surfactant is an amphipathic organic compound, including an anionic, cationic, zwitterionic, or nonionic compound.

The surfactant may for instance be a hydrocarbon compound, a hydroperfluoro carbon compound or a perfluorocarbon compound (supra), which is substituted by a moiety selected from the group consisting of a sulfonic acid, a sulphonamide, a carboxylic acid, a carboxylic acid amide, a phosphate, or a hydroxyl group. Numerous perfluorocarbon-surfactants are for instance known in the art. Examples include, but are not limited to, pentadecafluorooctanoic acid, heptadecafluorononanoic acid, tridecafluoroheptanoic acid, undecafluoro-hexanoic acid, 1,1,1,2,4,4,5,5,6,6,7,7,8,8,9,9,10,10,11,11,11-heneicosafluoro-3-oxo-2-unde-canesulfonic acid, 1,1,2,2,3,3,4,4,5,5,6,6-tridecafluoro-1-hexanesulfonic acid, 2,2,3,3,4,4,5,5-octafluoro-5-[(tridecafluorohexyl)oxy]-pentanoic acid [Chemical Abstracts No 174767-00-1], 2,2,3,3-tetrafluoro-3-[(tridecafluorohexyl)oxy]-propanoic acid] [CAS No 376-39-6], N,N'-[phosphinicobis(oxy-2,1-ethanediyl)]bis[1,1,2,2,3,3,4,4,5,5,6,6,7,7,8,8,8-heptadecafluoro-N-propyl-1-octanesulfonamide [the sodium salt has CAS No 82393-02-0], 1,1,2,2,3,3,4,4,5,5,6,6,7,7,8,8,8-heptadecafluoro-1-octanesulfonic acid, 1,1,2,2,3,3,4,4,5,5,6,6,7,7,8,8,8-heptadecafluoro-1-octanesulfonyl fluoride, [CAS No 190002-24-5], 2-[(3-D-galactopyranosyloxy)methyl]-2-[(1-oxo-2-propenyl)amino]-1,3-propanediyl carbamic acid (3,3,4,4,5,5,6,6,7,7,8,8,8-tridecafluorooctyl)-ester [CAS No 190002-24-5], 6-(3,3,4,4,5,5,6,6,7,7,8,8,8-tridecafluorooctyl hydrogen phosphate)-D-glucose, [the monosodium salt has CAS No 142740-63-4], 3-(3,3,4,4,5,5,6,6,7,7,8,8,9,9,10,10,10-heptadecafluorodecyl hydrogen phosphate)-D-glucose [the monosodium salt has CAS No 142740-66-7], 2-(perfluorohexyl)ethyl isocyanate [CAS No 142010-49-9], 2,2,3,3,4,4,5,5,6,6,7,7,8,8,8-pentadecafluoro-N-phenyl-octanamide [CAS No 3316-17-4], 1,1,2,2,3,3,4,4,5,5,6,6,7,7,8,8,9,9,10,10,11,11,12,12,12-pentacosafluoro-N-(2-hydroxyethyl)-N-propyl-1-dodecanesulfonamide [CAS No 84002-45-9], 2-methyl-2-[[(heptadecafluorooctyl)sulfonyl]methylamino]-2-propenoic acid ethyl ester [CAS No 14650-24-9], 3-(2,2,3,3,4,4,5,5,6,6,7,7,8,8,8-pentadecafluoro-1-oxooctyl)-benzenesulfonic acid [the sodium salt has CAS No 131666-65-4], 3-(heptadecafluorooctyl)-benzenesulfonic acid [the sodium salt has CAS No 146444-79-3], 4-[(2,2,3,3,4,4,5,5,6,6,7,7,8,8,8-pentadecafluoro-1-oxooctyl)amino]-benzenesulfonic acid [the monosodium salt has CAS No 176515-54-1], 3-[(o-perfluorooctanoyl)phenoxy]propanesulfonic acid [the sodium salt has CAS No 176515-56-3], N-ethyl-1,1,2,2,2-pentafluoro-N-(26-hydroxy-3,6,9,12,15,18,21,24-octaoxahexacos-1-yl)-ethanesulfonamide [CAS No 173219-11-9], 3-[ethyl[(heptadecafluorooctyl)sulfonyl]amino]-1-propanesulfonic acid [the sodium salt has CAS No 75032-81-4], 1,2,2,3,3,4,5,5,6,6-decafluoro-4-(pentafluoroethyl)-cyclohexanesulfonic acid [the sodium salt has CAS No 151017-94-6], 2-[1-[difluoro(pentafluoroethoxy)methyl]-1,2,2,2-tetrafluoroethoxy]-1,1,2,2-tetrafluoroethanesulfonic acid [the potassium salt has CAS No 70755-50-9], N-[3-(dimethyloxido-amino)propyl]-2,2,3,3,4,4-hexafluoro-4-(heptafluoropropoxy)-butanamide [CAS No 87112-48-9], N-ethyl-N-[(heptadecafluorooctyl)sulfonyl]-glycine [the potassium salt has CAS No 2991-51-7], or 2,3,3,3-tetrafluoro-2-[1,1,2,3,3,3-hexafluoro-2-[(tridecafluorohexyl)oxy]propoxy]-1-propanol [CAS No 484001-47-0], to name only a few.

Examples of perfluorocarbon-surfactants also include polymeric compounds such as α-[2-[bis(heptafluoropropyl)amino]-2-fluoro-1-(trifluoromethyl)ethenyl]-ω-[[2-[bis(heptafluoropropyl)amino]-2-fluoro-1-(trifluoromethyl)ethenyl]oxy]-poly(oxy-1,2-ethanediyl) [CAS No 135089-94-0], α-[2-[[(nonacosafluorotetradecyl)sulfonyl]propylamino]ethyl]-ω-hydroxypoly(oxy-1,2-ethanediyl) [CAS No 83995-63-5], polyethylene glycol diperfluorodecyl ether [CAS No 37382-58-4], α-[2-[ethyl[(heptadecafluorooctyl)sulfonyl]amino]ethyl]-ω-hydroxypoly(oxy-1,2-ethanediyl) [CAS No 29117-08-6], α-[2-[ethyl[(pentacosafluorododecyl)sulfonyl]amino]ethyl]-ω-hydroxy-poly(oxy-1,2-ethanediyl) [CAS No 82397-47-5], α-[2-[[(heptadecafluorooctyl)sulfonyl]propylamino]ethyl]-ω-hydroxy-poly(oxy-1,2-ethanediyl) [CAS No 52550-45-5], N-(2,3-dihydroxypropyl)-2,2-difluoro-2-[1,1,2,2-tetrafluoro-2-[(tridecafluorohexyl)oxy]ethoxy]-acetamide [CAS No 141483-28-5], α-(2-carboxyethyl)-ω-[[(tridecafluorohexyl)oxy]methoxy]-poly(oxy-1,2-ethanediyl) [the lithium salt has CAS No 496850-57-8], α-[2,3,3,3-tetrafluoro-2-[1,1,2,3,3,3-hexafluoro-2-(heptafluoropropoxy)propoxy]-1-oxopropyl]-ω-hydroxy-poly(oxy-1,2-ethanediyl) [CAS No 37541-12-1], and 2,3,3,3-tetrafluoro-2-(heptafluoropropoxy)-propionic acid polymer [CAS No 26099-32-1].

In one embodiment the surfactant has the structure $CF_3(CF_2)_m—(CH_2)_n—(OCH_2CH_2)_k—OH$, in which m is an integer from 3 to 100, n is an integer from 0 to 10, and k is an integer from 0 to 200, such as from 1 to 200. An illustrative example of a respective surfactant is α-(2,2,3,3,4,4,5,5,5-nonafluoropentyl)-w-hydroxy-poly(oxy-1,2-ethanediyl) [CAS No 82397-48-6]. An illustrative example of a hydroperfluoro-surfactant is 1-deoxy-1-[(4,4,5,5,6,6,7,7,8,8,9,9,9-tridecafluoro-1-oxononyl)amino]-xylitol [CAS-No 487027-48-5].

Typically the apparatus includes an upper inlet, which may for instance be or include an opening. This upper inlet is capable of providing a fluid communication between the processing compartment and the environment of the apparatus. Such an inlet may be used for introducing matter into the processing compartment or removing matter therefrom, such as a medium, a droplet or the immobilisation member. It may thus serves as a loading port, for instance for the immobilisation member. The opening defining the inlet or included therein is accordingly in some embodiments of a size sufficient to allow the insertion and/or removal of the immobilisation member. A respective inlet may be located on a top of the processing compartment, being at least essentially opposite to the base. In one embodiment the inlet is positioned and shaped to assist the positioning of a droplet when disposed into the processing compartment. In this embodiment the inlet may also assist in preventing a droplet from splitting into smaller droplets when contacting a medium in the processing compartment. In some embodiments a respective inlet may be sealable, for example by means of a lid or in the form of a valve. As will become apparent below, the device and method of the invention can however conveniently be used without sealing inlets of the processing compartment.

In some embodiments the upper inlet includes a guide, for example for positioning, moving or removing matter. The terms "positioning" and "to position" as used herein broadly relate to placing and removing matter into and out of a certain position. It thus includes bringing matter to and into a desired location and removing matter therefrom, i.e. bringing matter away from a certain location.

Figure 27:
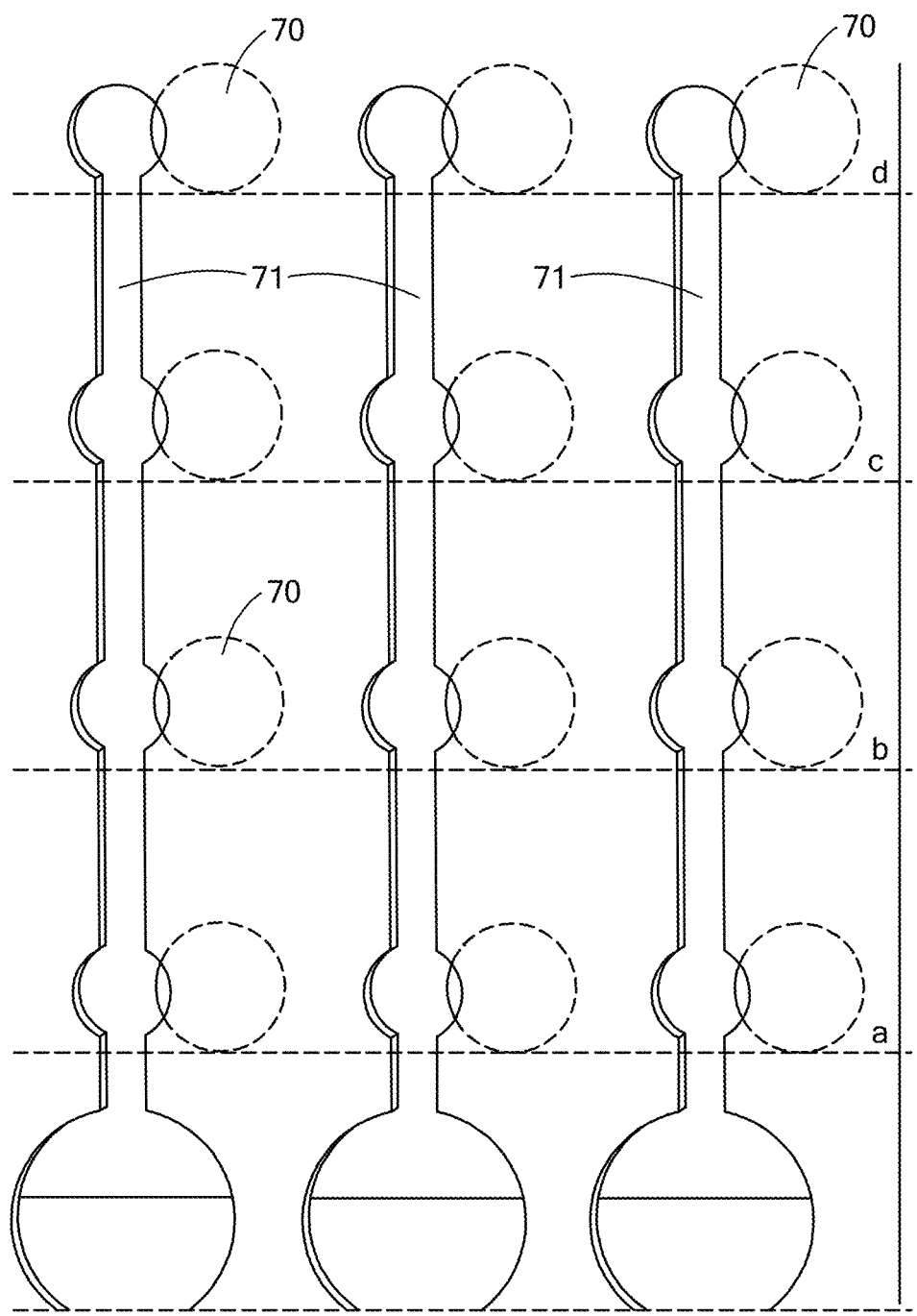
FIG. 27 illustrates an arrangement of through-holes of the pipetting guide shown in FIG. 26, in which the slots (71) of the pipetting guide are slightly offset from the predefined areas (70) of the patterned surface of a slide, included in an apparatus of the invention. Dashed lines labelled 'a', 'b', 'c' and 'd' indicate the arrangement of predefined areas (70) in form of columns.

A respective guide may for example provide guidance for the insertion or removal of matter in/from the processing compartment, such as into or out of the reservoir. In typical embodiments the guide is designed to allow positioning matter on the reservoir and/or into the reservoir of the processing compartment. In some embodiments the guide provides guidance for dispensing a liquid droplet onto the predefined immobilisation area within the surface of the immobilisation member. The apparatus may for instance be designed to guide positioning one or more dispensing devices. In some embodiments the guide provides guidance for inserting and/or removing an immobilisation member into/out of the reservoir. The guide may be of any desired geometry and orientation and may include any desired positioning means that assist or serve the positioning of matter. Examples of a suitable positioning means include, but are not limited to, a bore, a mount, a rail, a slide, a grove, a notch, an aperture, a channel or any combination thereof. An aperture may for example include a through hole that is arranged on a top of a predefined immobilisation area of the immobilisation member. In one embodiment the respective aperture is designed to avoid direct contact between a device used for dispensing or inserting matter, such as a nozzle or a pipette tip, and the predefined immobilisation area of the immobilisation member. For this purpose the aperture may for example be included in an inclined channel or the aperture may be positioned slightly offset from the predefined immobilisation area of the immobilisation member (FIG. 27). In some embodiments the guide has a pair of interacting positioning means. The pair of interacting positioning means may be designed to position a dispensing device relative to the predefined immobilisation area within the surface of the immobilisation member. Positioning a dispensing device may for instance be achieved in such a way that one or both elements of the pair of interacting positioning means are designed to receive the respective dispensing device. In some embodiments the pair of interacting positioning means may be designed to position, including to receive, a plurality of dispensing devices.

The pair of interacting positioning means may for instance include a bore and a mount. In such an embodiment the bore may be designed to receive the mount. The mount may for instance be designed to receive further matter. As an illustrative example, a mount that is designed to receive a nozzle or a pipette tip may be received by a bore or by a pair of bores (see e.g. FIG. 28). Accordingly, in some embodiments a respective interacting combination of a bore and a mount is designed to guide positioning a dispensing device. In some embodiments the mount is designed to guide positioning a dispensing device. In some embodiments the mount is designed to receive a positioning device. The mount may for instance include an aperture, for example for receiving a dispensing device such as a pipette tip. In some embodiments the mount includes a plurality of apertures, e.g. for receiving a plurality of dispensing devices.

In this regard the invention also provides a device for guiding and/or positioning a dispenser on a top of the reservoir of an apparatus of the invention, the apparatus having an upper opening. The guiding and/or positioning device is designed in such a way that it can be received by the upper opening of the apparatus. It may for instance have dimensions that match the dimensions of the opening of the apparatus or it may be equipped with an adapter that allows the apparatus to receive the guiding and/or positioning device. In some embodiments the guiding and/or positioning device is designed to receive a dispenser, e.g. a pipette tip. The guiding and/or positioning device may for example include a positioning means as described above, i.e. including or being a bore, a mount, a rail, a slide, a groove, a notch, an aperture, a channel or any combination thereof. The guiding and/or positioning device may also include pair of interacting positioning means as described above.

An upper inlet of the apparatus of the invention is in some embodiments included in an inlet member. In such embodiments an inlet member is arranged on a top of the reservoir of the processing compartment. The inlet member includes one or more inlets. The inlet member may be of any desired geometry, size or surface characteristics. It may for example have a hydrophilic or a hydrophobic surface facing the reservoir of the processing compartment. The inlet member may be fixed or removably arranged on the processing compartment or form a part thereof. In some embodiments the reservoir defined by the circumferential wall and the base of the processing compartment can be sealed from the ambience by means of the inlet member. A respective seal may be based on any desired mechanism, such as by mechanical force, electromagnetic force or pressure difference.

A respective seal may be applied to the inlet member, the processing compartment or both, so as to allow for a complete and tight connection of the reservoir and the cover or the inlet member. In typical embodiments the seal is accordingly designed to impermeably connect the inlet member to the processing compartment. A respective seal may likewise be used to impermeably connect a cover to the processing compartment. In some embodiments the seal is arranged in a position on the inlet member that corresponds to the position of the circumferential wall of the reservoir, once the inlet member is arranged on a top of the reservoir. In some embodiments the seal is arranged in a position on the circumferential wall of the reservoir of the processing compartment that corresponds to the position of the contact surface of the cover or the inlet member after being positioned on the reservoir.

The seal may be a sealing material such as a sealing fluid. Examples of such sealing materials include, but are not limited to, gels or liquids. A respective sealing may for example be a glue. Any glue that is compatible with desired measurements of sample fluid in the reactor module(s) may be used. A sealing material may also include a polymer that is derived from a photosensitive and/or heat-sensitive polymer precursor. Thus, the sealing material may be formed from a respective precursor after dispensing at a contact surface between reservoir (e.g. the circumferential wall thereof) and cover or inlet member, by polymerisation. Alternatively, an isolation medium may—once dispensing at a respective contact surface—be able to change its aggregation state, for instance by curing. Finally, a respective sealing material may also be of a solid state, but of such a nature that it is activated mechanically, electrically, and/or magnetically. In embodiments, where the sealing material is a polymer, it may upon such activation change its aggregation state, so that it can be dispensed onto the respective contact surface. Upon polymerisation, curing or "deactivation" of a respective material, the fluid on the respective contact surface solidifies, thus providing rigid or semi-rigid enclosure surfaces. Currently used sealing materials include, but are not limited to, polydimethylsiloxane (PDMS) and "Room Temperature Vulcanizing" (RTV) silicon.

Additionally, a person skilled in the art will be aware of the fact that a sealing process may be of reversible or irreversible nature. As an example, without oxidative treatment PDMS forms a noncovalent reversible seal with smooth surfaces. In some embodiments it may be desired to remove a cover or inlet member from the reservoir after a selected period of time. In such cases it may be desirable to use a reversible sealing. An irreversible sealing of PDMS contacting for instance glass, silicon, polystyrene, polyethylene or silicon nitride can be achieved by an exposure to an air or oxygen plasma.

In some embodiments the seal is an elastomeric contact device, e.g. a gasket such as an O-ring. In some embodiments the seal is an elastomeric contact element of the inlet member, a cover or of the processing compartment (such as the circumferential wall). It is recalled that sealing the apparatus of the invention may also be achieved by using another device than an inlet member, e.g. using a cover. A respective cover may likewise be removably arranged on a top of the reservoir.

In typical embodiments a cover may be designed to cap and/or close an upper opening of the apparatus (see above). The cover may in some embodiments be physically connected to the processing compartment. Thereby the cover and the processing compartment may define a closed space. The contact between the cover and the processing compartment may for example include the afore described seal, in order to prevent a fluid communication between the reservoir and the ambience. In other embodiments the cover may allow fluid communication between the reservoir and the ambience. As an illustrative example, it may be designed to prevent certain matter such as matter of a certain size from entering the reservoir, for instance by falling through an upper opening, and at the same time allow fluid such as air to pass via a gap between the cover and the circumferential wall of the processing compartment.

It may be desired to arrange a seal in such a way that, if at all, only a minimal dead space is formed adjacent to a seal. Such a dead space may for example be formed next to an O-ring between a cover (or an inlet member) and the circumferential wall of the processing compartment (e.g. FIG. 21). Such a dead space may be avoided by arranging the seal close to the inner surface of the reservoir (e.g. lower section of FIG. 21). It may also be avoided by matching the dimensions of the seal to the contact areas of the cover or inlet member, in particular in embodiments where the seal is a gel or a liquid, for instance a glue.

As noted above, the circumferential wall, the base and an inlet member or a cover define in some embodiments a closed space. Where sealing means are used to attach the inlet member to the processing compartment this space may for example be air-tight. A cover, as well as an inlet member, may include a void, which may be designed in any form, for example as a recess. In some embodiments a cover may be of a shape resembling a vat or a bowl (cf. FIG. 18, FIG. 19). Upon being arranged on the reservoir of the processing compartment such a void, including a recess, of the cover or inlet member may face the reservoir of the processing compartment. Thereby an additional space may be provided on a top of the processing compartment. In some embodiments a continuous space, provided by the respective void, including a recess, and the reservoir of the processing compartment may be formed.

The inlet member may for instance be arranged removably on a top of the reservoir of the processing compartment or in a fixed manner. In embodiments where the inlet member is removably arranged it may be replaced by other devices or elements such as a cover. In some embodiments the inlet member includes a guide as described above. In embodiments where the inlet member includes a plurality of inlets a respective guide may be designed to provide guidance for each of the respective inlets. In some embodiments a guide may be designed to provide guidance for only selected inlets, such as a single inlet. In some embodiments each inlet of a plurality of inlets is provided with a guide.

Figure 28A:
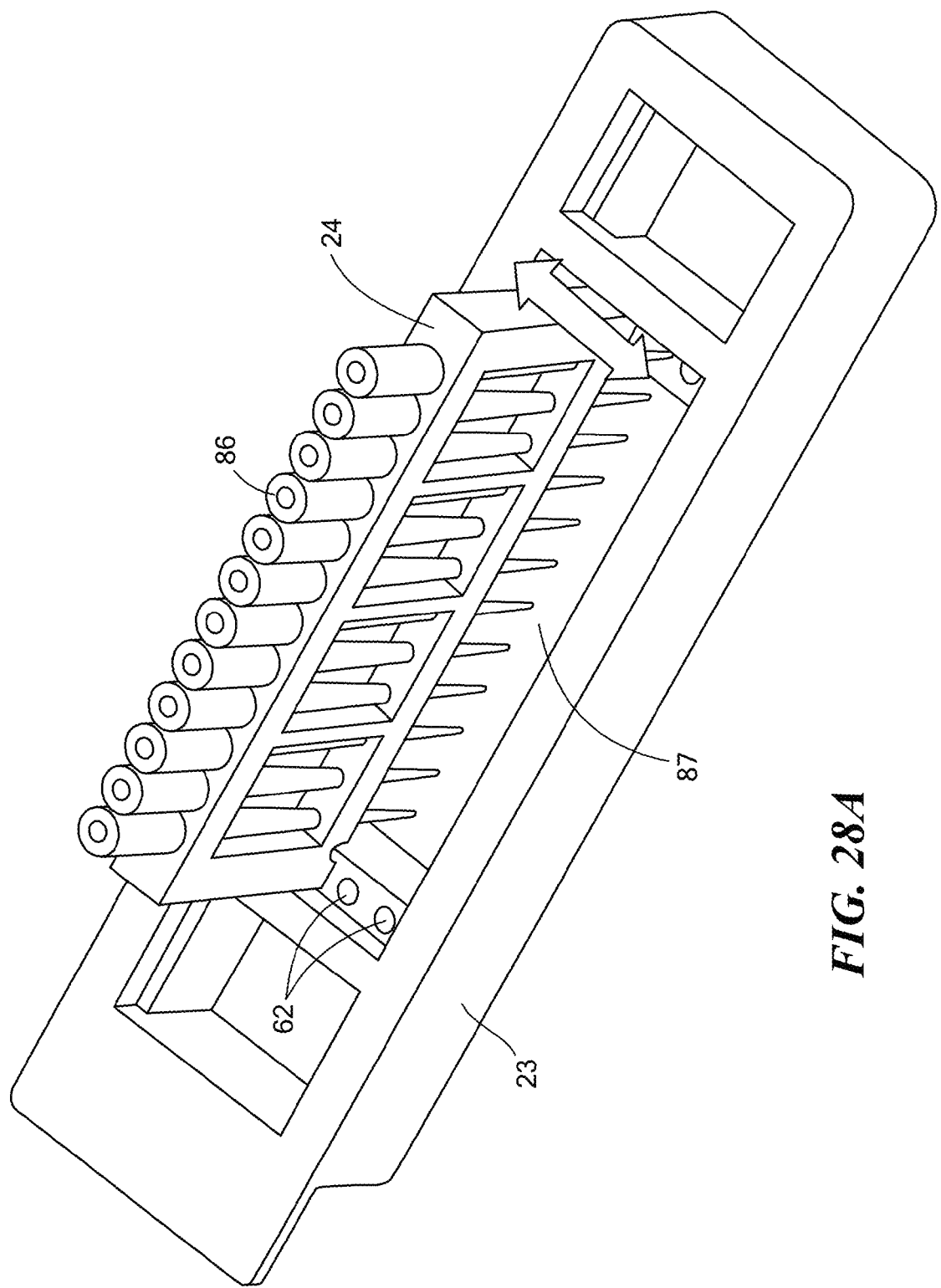
FIG. 28 depicts an example of an inlet member that includes a pair of interacting positioning means, a frame (23) with bores (62) and a mount (24) in top view (A) and seen from below (B).
Figure 28B:
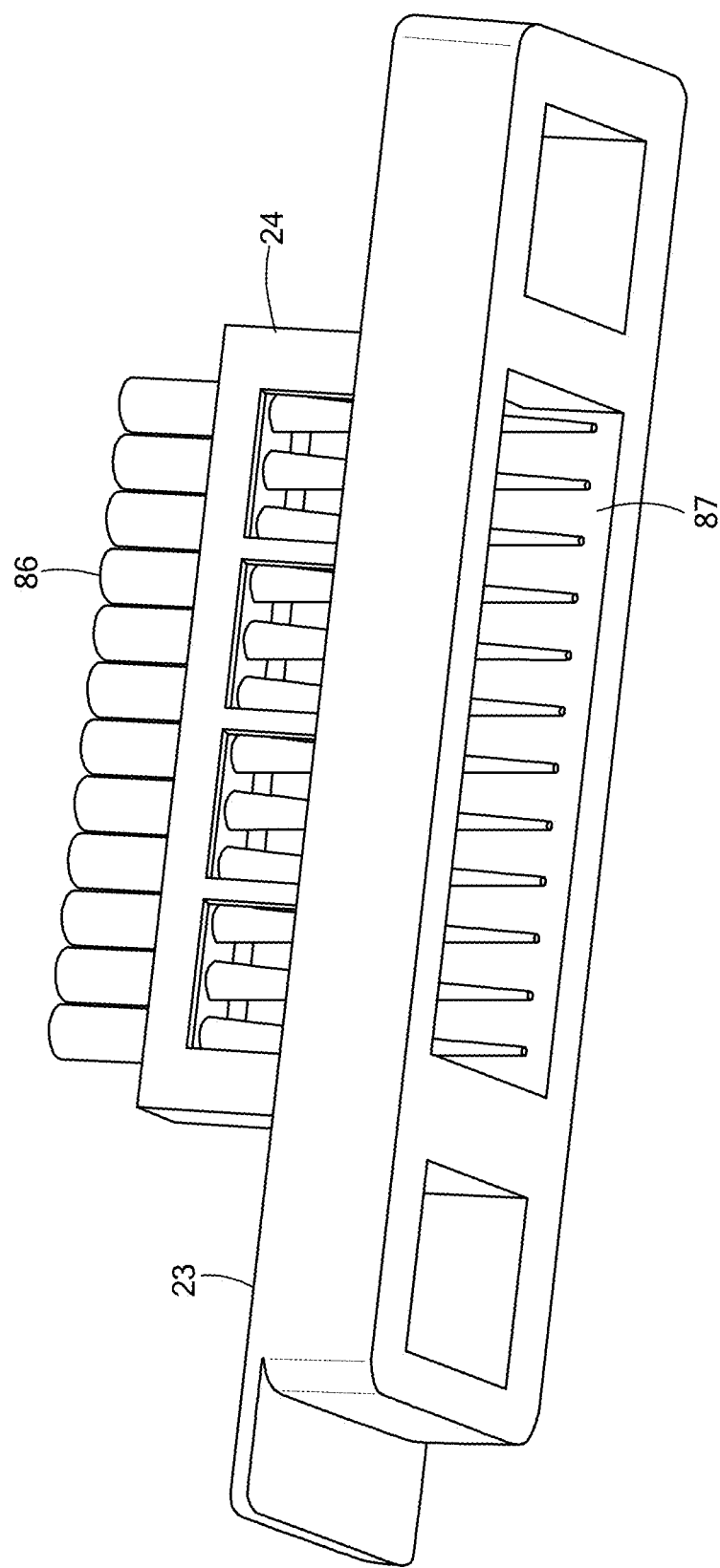

In some embodiments a respective guide, typically included in an inlet member, includes a bore and a mount, for instance in combination (see above). In such embodiments the bore may be designed to receive a mount. The mount may be designed to guide the dispensing of liquid, in particular liquid droplets, into the reservoir. The mount may for instance be designed to guide a dispensing device such as a pipette or a pipette tip. As an illustrative example, one or more pairs of bores may be designed to position a mount. The mount may match the dimensions of a nozzle or pipette tip. It may for instance be a pipetting guide as depicted in FIG. 28 and FIG. 29.

In some embodiments the apparatus of the invention includes an inlet member positioner. The inlet member positioner is coupled, for example connected, attached or attachable to the inlet member. In some embodiments the inlet member positioner is removably coupled (e.g. attached) to the inlet member. The inlet member positioner is further coupled, for example connected, attached or attachable to the reservoir. In some embodiments the inlet member positioner is removably coupled (e.g. attached) to the reservoir. In some embodiments both the reservoir and the inlet member are coupled to the inlet member positioner. In some embodiments both the reservoir and the inlet member are removably coupled to the inlet member positioner. The inlet member positioner is designed to position the inlet member on a top of the reservoir. In some embodiments the inlet member positioner is designed to assist in attaching (or to attach) the inlet member on a top of the processing compartment and thus on a top of the reservoir thereof. In some embodiments the inlet member positioner is further designed to seal the processing compartment by sealing the connection of the inlet member on a top of the reservoir of the processing compartment. As an illustrative example, the inlet member positioner may exert mechanical force on the inlet member to actuate a lock or to apply pressure on a gasket arranged between the inlet member and the top of the reservoir of the processing compartment. In some embodiments the inlet member positioner includes a pivoting means such as for example depicted in FIG. 20. The inlet member positioner may for example be a swing device. In an apparatus with a respective device with a pivoting means the inlet member may be pivotally mounted on a top of the reservoir, for example when coupled or attached to the inlet member positioner. Thereby the inlet member may be allowed to be pivoted relative to the reservoir.

In this regard the invention also relates to a device for attaching an inlet member and/or a cover to the reservoir of an apparatus of the invention. The device is typically designed to allow the inlet member and/or the cover to be positioned on a top of the reservoir and to allow an attachment of inlet member/cover and reservoir, once in the respective position. The device includes a first and a second holder. The first holder is designed to receive the reservoir of the apparatus of the invention. The second holder is designed to receive an inlet member and/or a cover. The first and the second holder are fitted such that the second holder can be positioned on a top of the first holder. Thereby an inlet member/cover received by the second member can be positioned on a top of a reservoir received by the first member. The term "fitted" broadly refers to a geometric and/or a functional match, i.e. including the meanings "arranged", "suited", "put in place", "of proper orientation", "of proper size", "adapted" and "qualified for". In some embodiments the device includes a pivoting means (supra, FIG. 20). By such a pivoting means the first mount and the second mount may be pivotally connected, e.g. swivel-mounted. In some embodiments the device includes a lever for mounting the second holder into a position on a top of the first holder (cf. FIG. 20). In one embodiment the two holders can thereby be manually positioned. In some embodiments the lever is coupled to the first holder. In some embodiments the lever is coupled to the second holder. In some embodiments the lever is coupled to both holders. In some embodiments the lever may include a locking means for the lever to be locked, for example to prevent it from being accidentally actuated.

As explained above, the immobilisation member includes a predefined immobilisation area. In some embodiments this predefined immobilisation area may include a molecule with a linking moiety. A respective molecule may be hydrocarbon-based (including polymeric) and include nitrogen-, phosphorus-, sulphur-, carben-, halogen- or pseudohalogen groups. As an illustrative example, the immobilisation area of the surface of the immobilisation member may include, for instance be coated with, a brush-like polymer, for example with short side chains. The immobilisation surface may also include a polymer that includes a brush-like structure, for example by way of grafting. It may for example include functional groups that allow for the covalent attachment of target matter, for example a molecule such as a protein or a nucleic acid molecule. Examples of a respective linking moiety include, but are not limited to, an amino group, an aldehyde group, a thiol group, a carboxy group, an ester, an anhydride, a sulphonate, a sulphonate ester, an imido ester, a silyl halide, an epoxide, an aziridine, a phosphoramidite and a diazoalkane. A general introduction into aspects of covalent immobilisation via a linking moiety has for example been given by Goddard & Hotchkiss (*Progress in Polymer Science* (2007) 32, 7, 698-725). It is noted in this regard that non-covalent immobilisations are likewise suitable for the method of the invention.

In some embodiments the linking moiety is a receptor molecule for a target molecule such as a protein, a nucleic acid, a polysaccharide or any combination thereof. In such embodiments the linking moiety and the target molecule may define a specific binding pair. Examples of a respective receptor molecule include, but are not limited to an immunoglobulin, a mutein based on a polypeptide of the lipocalin family, a glubody, a protein based on the ankyrin or crystalline scaffold, an avimer, the T7 epitope, maltose binding protein, the HSV epitope of herpes simplex virus glycoprotein D, the hemagglutinin epitope, and the myc epitope of the transcription factor c-myc, an oligonucleotide, an oligosaccharide, an oligopeptide, biotin, dinitrophenol, digoxigenin and a metal chelator (cf. also below). As an illustrative example, a respective metal chelator, such as ethylenediamine, ethylenediamine-tetraacetic acid (EDTA), ethylene glycol tetraacetic acid (EGTA), diethylenetriaminepenta-acetic acid (DTPA), N,N-bis(carboxymethyl)glycine (also called nitrilotriacetic acid, NTA), 1,2-bis(o-aminophenoxy)ethane-N,N,N',N'-tetraacetic acid (BAPTA), 2,3-dimercapto-1-propanol (dimercaprol), porphine or heme may be used in cases where the target molecule is a metal ion. As an example, EDTA forms a complex with most monovalent, divalent, trivalent and tetravalent metal ions, such as e.g. silver ($Ag^+$), calcium ($Ca^{2+}$), manganese ($Mn^{2+}$), copper ($Cu^{2+}$), iron ($Fe^{2+}$), cobalt ($Co^3$) and zirconium ($Zr^{4+}$), while BAPTA is specific for $Ca^{2+}$. In some embodiments a respective metal chelator in a complex with a respective metal ion or metal ions defines the linking moiety. Such a complex is for example a receptor molecule for a peptide of a defined sequence, which may also be included in a protein. As an illustrative example, a standard method used in the art is the formation of a complex between an oligohistidine tag and copper ($Cu^{2+}$), nickel ($Ni^{2+}$), cobalt ($Co^{2+}$), or zink ($Zn^{2+}$) ions, which are presented by means of the chelator nitrilotriacetic acid (NTA).

As an illustrative example, a mixture of a polyelectrolyte such as poly(3-8(S)-5-amino-5-methoxycarboxyl-3-oxapentyl]2,5-thiophenylene hydrochloride) and a peptide (e.g. a synthetic peptide or a peptide isolated from natural sources) or a mixture of poly(3-[(S)-5-amino-5-carboxyl-3-oxapentyl]-2,5-thiophenylene hydrochloride) and calmodulin may be immobilised on a surface area of poly(dimethylsiloxane) by incubation of a respective buffered aqueous solution thereon and subsequently drying the same as described by Åsberg et al. (*Langmuir* (2006) 22, 5, 2205-2211).

In some embodiments a respective linking moiety has been obtained by a reaction of a functional group of a first linking moiety with a second linking moiety. This may for example be desired to obtain a linking moiety that has a chosen degree of specifity for selected target matter. The linking moiety may for instance be reacted with a receptor molecule for a target molecule. The receptor molecule and the target molecule define a specific binding pair (see above and below). By a respective reaction a complex, such as a coordinative complex, or a covalent bond may be formed. By forming such a complex or bond the previous linking moiety is being converted into another linking moiety. As an illustrative example, a respective method of the present invention may include contacting the surface of the substrate with a receptor molecule for a target molecule (see also above). The receptor molecule is capable of interacting with the linking moiety, such that a complex between the receptor molecule and the linking moiety is formed. The formation of this complex may, in some embodiments, result in, or be part of, the formation of a covalent bond. As a result, the receptor molecule is immobilised on the plurality of surface areas via the linking moiety. The linking moiety has in turn been converted into another linking moiety.

Aldehyde, amino or thiol groups may for example be reacted with a peptide, protein, oligosaccharide, an oligonucleotide or any other molecule that has a desired specifity for a selected target molecule (see e.g. Sanghvi et al., 2005, supra, for a specific example). The resulting moiety may for instance be a moiety that is known in the art as an "affinity tag". Examples of such moieties include, but are not limited to biotin, dinitrophenol, digoxigenin, oligohistidine, polyhistidine, an immunoglobulin domain, maltose-binding protein, glutathione-S-transferase (GST), calmodulin binding peptide (CBP), FLAG'-peptide, the T7 epitope (Ala-Ser-Met-Thr-Gly-Gly-Gln-Gln-Met-Gly), maltose binding protein (MBP), the HSV epitope of the sequence Gln-Pro-Glu-Leu-Ala-Pro-Glu-Asp-Pro-Glu-Asp of herpes simplex virus glycoprotein D, the hemagglutinin (HA) epitope of the sequence Tyr-Pro-Tyr-Asp-Val-Pro-Asp-Tyr-Ala and the "myc" epitope of the transcription factor c-myc of the sequence Glu-Gln-Lys-Leu-Ile-Ser-Glu-Glu-Asp-Leu.

As a further illustrative example, a respective moiety may also be an antibody, a fragment thereof or a proteinaceous binding molecule with antibody-like functions. Examples of (recombinant) antibody fragments are Fab fragments, Fv fragments, single-chain Fv fragments (scFv), diabodies, triabodies (Iliades, P., et al., *FEBS Lett* (1997) 409, 437-441), decabodies (Stone, E., et al., *Journal of Immunological Methods* (2007) 318, 88-94) and other domain antibodies (Holt, L. J., et al., *Trends Biotechnol*. (2003), 21, 11, 484-490). An example of a proteinaceous binding molecule with antibody-like functions is a mutein based on a polypeptide of the lipocalin family (WO 2003/029462; WO 2005/019254; WO 2005/019255; WO 2005/019256; Beste et al., *Proc. Natl. Acad. Sci. USA* (1999) 96, 1898-1903). Lipocalins, such as the bilin binding protein, the human neutrophil gelatinase-associated lipocalin, human Apolipoprotein D, human tear lipocalin, or glycodelin, posses natural ligand-binding sites that can be modified so that they bind to selected small protein regions known as haptens. Other non-limiting examples of further proteinaceous binding molecules so-called glubodies (see WO 96/23879), proteins based on the ankyrin scaffold (Mosavi, L. K., et al., *Protein Science* (2004) 13, 6, 1435-1448) or the crystalline scaffold (WO 2001/04144), the proteins described by Skerra (*J. Mol. Recognit.* (2000) 13, 167-187), AdNectins, tetranectins, avimers and peptoids. Avimers contain so called A-domains that occur as strings of multiple domains in several cell surface receptors (Silverman, J, et al., *Nature Biotechnology* (2005) 23, 1556-1561). Adnectins, derived from a domain of human fibronectin, contain three loops that can be engineered for immunoglobulin-like binding to targets (Gill, D. S. & Damle, N. K., *Current Opinion in Biotechnology* (2006) 17, 653-658). Tetranectins, derived from the respective human homotrimeric protein, likewise contain loop regions in a C-type lectin domain that can be engineered for desired binding (ibid.). Peptoids, which can act as protein ligands, are oligo(N-alkyl) glycines that differ from peptides in that the side chain is connected to the amide nitrogen rather than the a carbon atom. Peptoids are typically resistant to proteases and other modifying enzymes and can have a much higher cell permeability than peptides (see e.g. Kwon, Y. -U., and Kodadek, T., *J. Am. Chem. Soc.* (2007) 129, 1508-1509). Where desired, a modifying agent may be used that further increases the affinity of the respective moiety for any or a certain form, class etc. of target matter.

In some embodiments the apparatus includes an electrode, a magnet (e.g. a bar magnet), an electromagnet, an array of magnets or electromagnets, or any combination thereof. A respective electrode, magnet or electromagnet may be positioned anywhere in the apparatus and is capable of providing an electric, magnetic or electromagnetic field respectively. As an illustrative example, it may be included in the base of the reservoir. As a further illustrative example, an electrode may be included in an immobilisation member, for example in form of an electro-chip (e.g. FIG. 4F).

In some embodiments the apparatus includes one or more devices for stacking a plurality of identical or similar apparatuses. Such devices may be designed for securing an apparatus on top of another apparatus. An illustrative example are circular indentions depicted in FIG. 16B and FIG. 17. Respective indentions may for example match corresponding protrusions of a further apparatus according to the invention. In some embodiments the apparatus includes one or more devices for attaching and/or securing the apparatus on or to another apparatus, such as a detection instrument (see e.g. FIG. 15) or an apparatus that provides a desired ambience such as a desired temperature or atmosphere.

In some embodiments the apparatus further includes a feeding module. The feeding module is fluidly connected to the processing compartment. It generally allows the flow of fluid into and/or out of the processing compartment, in particular into and/or out of the reservoir. The feeding module may for example be physically connected to the reservoir, for instance via a port. A respective port may be arranged anywhere in the processing compartment, such as the base, the circumferential wall or a cover or an inlet member. In some embodiments the feeding module includes an inlet channel. A respective inlet channel is designed to allow the flow of medium into the reservoir. In some embodiments the feeding module includes an outlet channel. A respective outlet channel is designed to allow the flow of medium out of the reservoir. In some embodiments the feeding module includes a multi-purpose channel, which can serve as both an inlet and an outlet channel. In some embodiments the feeding module includes both an inlet and an outlet channel. Liquid that is miscible with the liquid of the liquid droplet may for example be allowed to flow into the reservoir and/or out of the reservoir via the feeding module. Medium immiscible with the liquid of the liquid droplet may also be allowed to flow into the reservoir and/or out of the reservoir via the feeding module.

In some embodiments the feeding module also includes a pressurizing device for applying pressure to any element or part of the apparatus that is fluidly connected to the pressurizing device. The pressurizing device may for example be designed to exert pressure onto medium, such as a liquid, present in an inlet channel of the feeding module. Thereby the pressure may cause the medium to flow into the reservoir, to which the respective inlet channel is fluidly connected. The pressure applied by the pressurizing device may in some embodiments engage a sealing device such as a valve. In some embodiments, pressure applied by the pressurizing device acts on a medium present in the reservoir, thereby for example causing it to flow out of the reservoir. In some embodiments the pressurizing device is designed for applying negative pressure, thereby causing medium, e.g. fluid, to flow in the direction of the pressurizing device. A pressurizing device designed for applying negative pressure may for instance be fluidly connected to an outlet channel of the feeding module, thereby causing medium in the reservoir, to which it is fluidly connected, to flow out of the reservoir. A respective pressurizing device may for example include or be a pump, a syringe or a combination thereof.

In some embodiments the feeding module is removably connected to the processing compartment. The feeding module may for instance include connecting/disconnecting means to allow or facilitate connection and/or disconnection or removal of the feeding module to the processing compartment.

In some embodiments the apparatus of the invention includes a reservoir holder such as a pivoting reservoir holder. The pivoting reservoir holder may be designed to receive and to pivot the reservoir. Pivoting the reservoir may facilitate the flow of medium into and/or out of the reservoir (see also below). The apparatus may also include means for mechanically moving or agitating (in particular shaking) the reservoir and/or the processing compartment. An illustrative example of such means is an agitation device, which is designed to receive and to agitate the reservoir. The agitation device may thereby facilitate or cause agitating, mixing and/or filtering of matter that is present in the reservoir.

The method of processing a biological and/or chemical sample of the present invention includes providing an apparatus as described above. As already indicated above, providing the apparatus may include providing a device that includes a reservoir. The reservoir of a respective device is defined by a circumferential wall and a base. The reservoir is furthermore capable of receiving an immobilisation member (see above). Providing the apparatus may further include providing the immobilisation member, as well as disposing the immobilisation member into the reservoir. Thereby the processing compartment of the apparatus is formed.

The method of the invention further includes disposing the medium, which is immiscible with the liquid of the liquid droplet, into the apparatus. As an illustrative example the apparatus may include an inlet such as a valve through which the medium is allowed to enter. As a further illustrative example, the apparatus may include an upper opening as described above. Through this opening the medium may for instance be poured into the reservoir. An amount of medium is filled into the reservoir that is sufficient to achieve a complete coverage of the predefined immobilisation area(s) by the medium. In embodiments of the method where the immobilisation member is disposed into the reservoir, the medium may for example be disposed into the reservoir before, at the same time, or after the immobilisation member is disposed therein. As an illustrative example, in one embodiment a device with a reservoir is provided first, thereafter the medium is disposed into the reservoir of the device, and subsequently the inlet member is disposed into the reservoir. The latter embodiment may for instance be chosen in order to avoid the formation of undesired air bubbles when providing the apparatus and filling liquid into the processing compartment thereof.

Typically the amount of medium filled in the reservoir is sufficient to entirely cover the patterned surface of the immobilisation member. In some embodiments the amount of medium is furthermore sufficient to entirely cover a liquid droplet immobilised on the predefined immobilisation surface area of the respective patterned surface. In some embodiments the amount of medium is sufficient to cover the immobilisation member, but only sufficient to partly accommodate a droplet without entirely covering the same. Such embodiments may for instance be selected where it is desired to handle evaporating droplets using the method and/or apparatus of the invention (see Rastogi, V., & Velev, O. D., *Biomicrofluidics* [2007] 1, 014107-1-014107-17 for an example).

Where desired, a further medium may be added that is immiscible with the medium in the processing compartment, as long as it does not prevent or interfere with dispensing a desired liquid droplet therein. Another liquid of lower density may for example be added to the medium in the processing compartment, for instance to cover the surface of the medium in the processing compartment, e.g. in form of a layer. In such embodiments the respective further liquid is typically selected to be immiscible with the medium in the processing compartment and maybe of lower density than the medium in the processing compartment. This may for instance be desired in order to prevent evaporation of the medium in the processing compartment. As an illustrative example, the medium in the processing compartment may be a hydroperfluoro carbon compound or a perfluorocarbon compound, and the liquid may be a layer of water. In such embodiments the method of the present invention thus includes providing a liquid which is immiscible with the medium (which may e.g. already be disposed in the processing compartment), and which is of lower density than that medium, and disposing the liquid into the processing compartment of the apparatus. Disposing a respective liquid may be carried out at any point of time during the method of the invention. It may in some embodiments be advantageous to avoid contact between the liquid droplet and such a further medium. In such cases it may be desired to add this further medium only after the liquid droplet has been immobilised on the immobilisation member of the apparatus and the medium disposed into the reservoir of the apparatus.

The method of the invention further includes providing a liquid droplet (see above). The liquid droplet may be of any desired volume. It may for instance have a volume in the range of about 1 pl to about 1 ml, a volume in the range of about 0.1 nl to about 500 µl, or a volume in the range of about 100 nl to 100 µl. Handling of droplets of a volume above 1 ml in air may in some embodiments require further adaptions of the droplet environment. In this regards, the skilled artisan will be aware that when using a droplet of large volume (such as e.g. 2 ml), the respective droplet may split into smaller droplets when contacting a surface. Where such splitting is undesired when carrying out the method of the invention, suitable volumes for a droplet of a selected liquid can easily be determined experimentally.

Furthermore the method of the invention includes disposing the liquid droplet onto the predefined immobilisation area(s). Disposing the droplet onto the predefined immobilisation area may include disposing the droplet anywhere within or above the apparatus of the invention or a part thereof, including anywhere within or above the processing compartment, as well as the reservoir or the immobilisation member. In some embodiments the droplet is disposed into the reservoir or onto the immobilisation member before assembling a respective processing compartment by inserting the immobilisation member into the reservoir.

In some embodiments the liquid droplet is formed by disposing a liquid onto the immobilisation member, such that it is disposed on the surface that is patterned in such a way that it includes at least one predefined immobilisation area, thus contacting or covering the respective surface. As a result the liquid may form a droplet on the at least one predefined immobilisation area. A droplet may be formed on each predefined immobilisation area that is covered or contacted with the liquid. In some embodiments the medium that is immiscible with the liquid of the liquid droplet (see above) may be disposed onto the patterned surface, for example before, together with or after disposing liquid onto the immobilisation member as indicated above. Thereby the liquid may form a droplet on the at least one predefined immobilisation area.

In some embodiments a first liquid droplet is disposed onto the at least one predefined immobilisation area of the patterned surface. This first liquid droplet may in some embodiments be different from a second liquid droplet, which is at a subsequent stage used in the method of the present invention. Disposing this first liquid droplet may for example be carried out before disposing any medium into the apparatus, including the reservoir. The liquid of this first liquid droplet may for instance be an aqueous cell culture medium. In some embodiments disposing a first liquid droplet onto the at least one predefined immobilisation area also includes adding at least one, or a plurality of, microorganism(s) to the apparatus. The microorganism(s), for example cell(s), may for example be included in the liquid droplet. Furthermore, a respective microorganism is capable of adhering to the predefined immobilisation surface area.

Figure 13A:
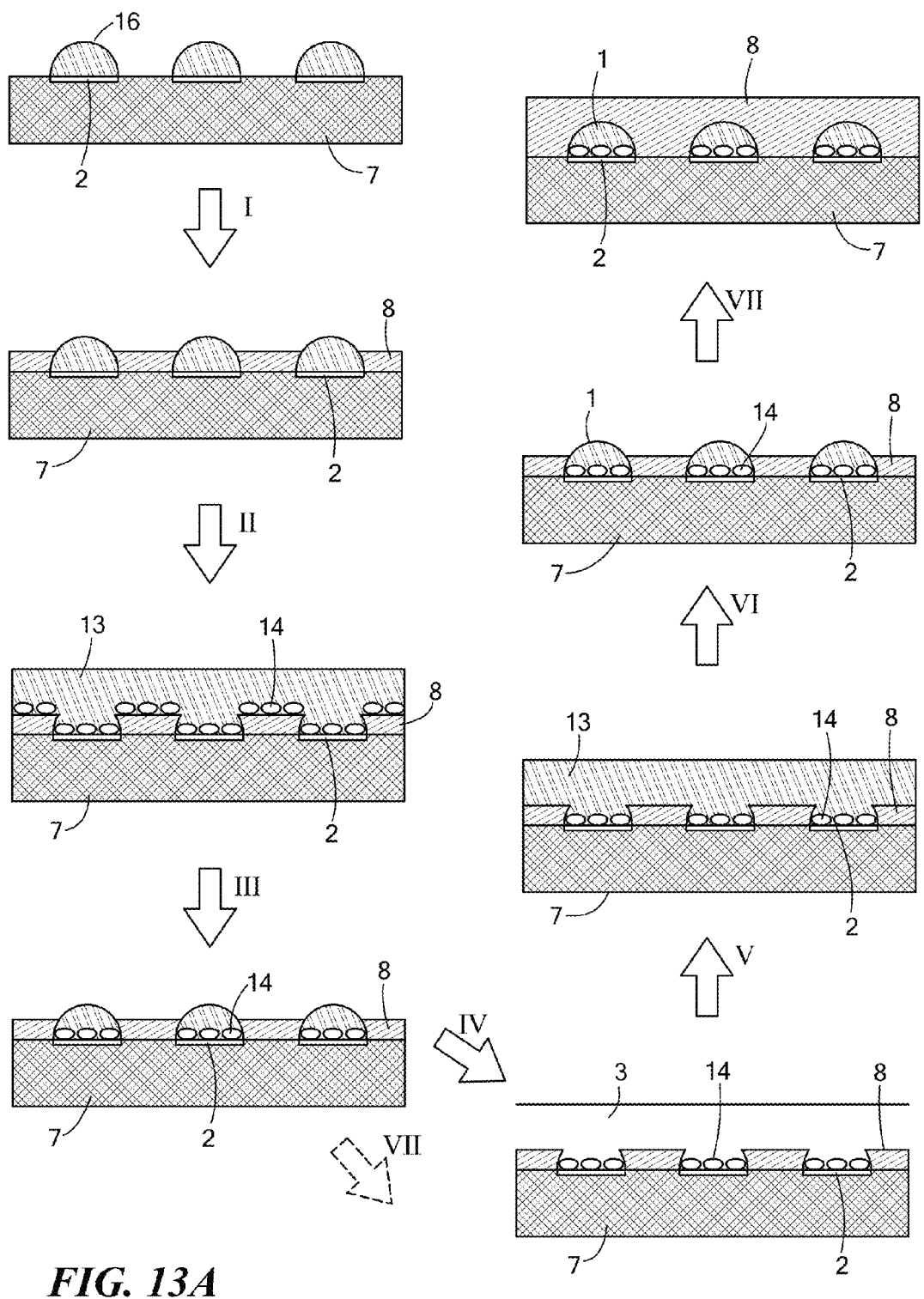
FIG. 13A depicts a bulk cell culture in microarray format according to an embodiment of providing a liquid droplet of the method of the present invention.

The medium that is immiscible with the liquid of the liquid droplet is furthermore, typically thereafter, disposed onto the residual surface (see e.g. FIG. 13A, step I). As explained above, this residual surface is the surface area that is of a lower surface energy than the liquid of the liquid droplet, and of at most about the same surface energy as the medium. In some embodiments only an amount sufficient to cover the residual surface is disposed. In other embodiments, a large amount of immiscible medium is added. In such embodiments medium is thereafter drained to leave a thin layer of immiscible medium on the surface. A further amount of the liquid of the liquid droplet is disposed into the reservoir (see e.g. FIG. 13A, step II). The amount of liquid used is sufficient to cover the immiscible medium. Thereby contact between the liquid and the residual surface, i.e. the surface that is of at most about the same surface energy as said medium, is prevented.

In some of these embodiments at least one or a plurality of microorganism(s) is added upon disposing a further amount of the liquid into the reservoir (see e.g. FIG. 13A, step II). The microorganism(s), for example cell(s), may for example be included in the further amount of liquid. Furthermore, the microorganisms are capable of adhering to the predefined immobilisation surface area. Such embodiments can therefore be used as a bulk cell culture in microarray format as depicted in FIG. 13. The microorganisms settle down at the interface between the immiscible medium and the liquid, as well as on the at least one predefined immobilisation area of the patterned surface. At this stage the microorganisms may be cultured, so that the liquid can remain in the reservoir for an extended period of time.

In these embodiments of the method where a first liquid droplet is disposed onto the predefined immobilisation area and a further amount of the liquid is added to cover the residual surface area, the liquid is further removed from the reservoir of the apparatus. This may for example be carried out after cultivation of the microorganisms is completed. Upon removing the liquid a droplet of the liquid remains on the at least one predefined immobilisation area of the patterned surface. Thereby a second liquid droplet is formed on the at least one predefined area. In some embodiments the liquid of the first liquid droplet and the liquid of the second liquid droplet are identical. In other embodiments the two liquids differ from each other.

Those skilled in the art will appreciate that the present invention can thus provide a plurality of tissue culture vessels on a micro scale or below, in which the individual cell culture vessels are separated by an immiscible medium. Previous experiments with patterned surfaces have shown that cells such as *Pseudomonas aeruginosa* preferably adhere to hydrophilic surface areas, albeit also adhering to hydrophobic surface areas (Satriano, C., et al., *Materials Science & Engineering C* (2006) 26, 942-946).

Figure 4A:
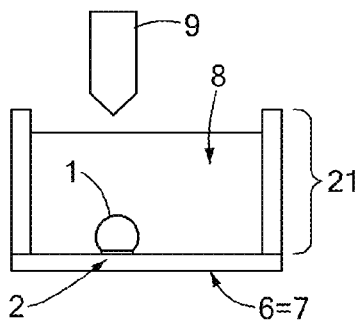
FIG. 4 schematically depicts embodiments of how a droplet can be positioned and immobilised by means of embodiments of the method and apparatus of the present invention (A-I).

Disposing the droplet onto the predefined, e.g. hydrophilic, immobilisation area may also include forming the droplet by dispensing. As an example, the droplet may be dispensed above the predefined immobilisation area, such as for instance centrally or sideways inserted anywhere into the medium in the processing compartment to dispense the droplet. Where the droplet is of lower density than the immiscible liquid, the nozzle may for instance be placed under the immobilisation member, so that the formed liquid droplet is driven upward under or onto the predefined immobilisation area within the surface thereof by buoyancy force. In some embodiments a dispensing tube, such as the nozzle of a dispenser, is positioned immediately above the predefined immobilisation area as depicted in FIG. 4C or below the predefined immobilisation area as depicted in FIG. 4D. As two further illustrative examples for a dispensing tube, the droplet may be dispensed by means of a pipette tip or a capillary tube. The respective dispenser may contain the liquid of the droplet and be designed or adapted to produce and break a drop at an outlet, such as the end of a tip, to form a droplet in a medium. To facilitate the breaking of a drop from the outlet of a dispenser, the surface of the dispenser can be coated with a hydrophobic, and/or oleophobic coating such as a perfluorocarbon film such as Teflon (cf. also above). In some embodiments, the dispenser of a liquid may be agitated briefly to break a drop from the end of the tip. Such methods of droplet release can be used individually or in combination.

As mentioned above, in other embodiments a liquid droplet can be dispensed at any desired distance from onto the predefined immobilisation area and subsequently be directed thereto. As an illustrative example, the liquid droplet may be dispensed above the medium that is included in the reservoir. The liquid droplet may then be allowed or forced to contact the medium and to enter it. Furthermore the liquid droplet may then be allowed or forced to pass through the medium to the hydrophilic surface area that is included within the patterned surface of the immobilisation member. Where required, the liquid droplet may be directed or forced into a certain direction, such as sideward or upward etc., so that it is able to reach the immobilisation member. The liquid droplet may then be allowed to contact the predefined immobilisation area.

In some embodiments a liquid droplet, or a plurality thereof, may be formed on a further patterned surface. Droplet formation may in these embodiments for instance be carried out via contact with the respective liquid, thereby producing monodisperse droplets (see Kusumaatmaja, H., & Yeomans, J. M., *Langmuir* [2007] 23, 956-959). The further patterned surface with droplets formed thereon may then be placed in a position next to the immobilisation member. Upon contact of the droplets with the patterned surface of the immobilisation member the droplets may be disposed thereon. In some embodiments one or more liquid droplets may be directly formed on the surface of the immobilisation member in a corresponding manner.

Directing the droplet, including allowing it to enter the medium that is immiscible with the liquid of the liquid droplet, can for instance be achieved by exerting a mechanical force such as a positive pressure. As an illustrative example, a droplet of a liquid can be dispensed above the processing compartment or above the medium included therein. Where desired, it may for instance be dispensed from a position that is perpendicularly beyond the position of the predefined immobilisation area, for example plumb, as viewed along the direction of the force of gravity. Dispensing the droplet by means of pressure may apply a force on the liquid droplet that provides a velocity that is firstly sufficient to allow the droplet to enter the medium, whereby it may also enter the processing compartment. In these embodiments, the kinetic energy of a respective droplet is higher than both the resistance of the medium and the deformation of the droplet at the contraction. Once the droplet has passed the surface of the medium in the processing compartment, it is furthermore exposed to the same force. The force is then, secondly, sufficient to accelerate the liquid droplet to a velocity that causes the liquid droplet to pass through this medium up to the patterned surface area on the immobilisation member. The liquid droplet is thereby allowed to contact the predefined immobilisation area.

Figure 3:
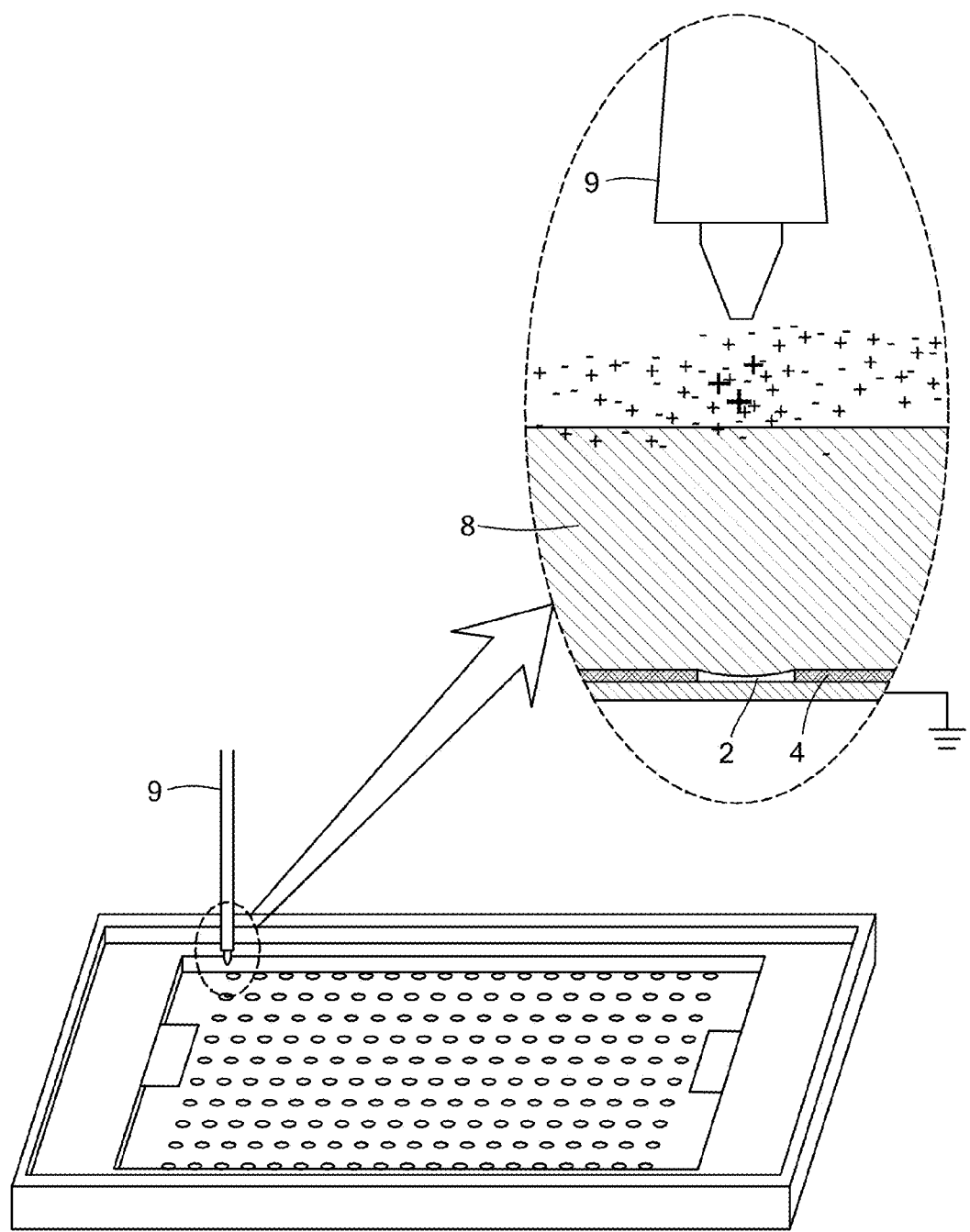
FIG. 3 shows schematically an array of samples in droplets when processed with an embodiment of the apparatus of the present invention (A), an example of dispensing an array of droplets (B), and an enlargement of a nozzle of two exemplary dispensers before or during dispensing a droplet (C, D).

In some embodiments, the method also includes charging the liquid droplet, for example by means of ionized air (see e.g. FIG. 3). In such embodiments the liquid droplet is typically charged before contacting the medium in the processing compartment. In some embodiments the droplet is charged before entering the reservoir. In one of these embodiments, the liquid is being charged in a nozzle before being dispensed. In another embodiment the liquid droplet is dispensed first— for instance from a nozzle of a dispenser, whereafter the formed liquid droplet is being charged, for example by means of ionized air. In embodiments were a plurality of droplets of different liquids is used, one or more of these liquids may be selectively charged, for example before being dispensed. A liquid may for instance be charged, whether before or after dispensing, by means of corona charging using a commercially available charger, such as Simco's V-Block electrostatic charger. It is understood that, for charging, only charged ions from one electrode, either positive or negative, get released from a charger. Many charging devices are commercially available and, if desired, they can easily be adapted to provide a dispenser with a modification of interest.

In some embodiment the method includes exposing the liquid droplet to an electric field, including an electrostatic field, such that the droplet is allowed or forced to enter the medium and to pass through it toward the immobilisation member. Typically, in this embodiment the liquid droplet has been charged at an earlier stage (supra). In another above the same. In some embodiments of the method of the invention the droplet is dropped onto and/or directed into the medium that has been disposed in the processing compartment of the apparatus. In other embodiments the droplet is formed together with the respective medium, which is immiscible with the liquid of the liquid droplet. In the course of all embodiments of the method of the invention the droplet is caused to be immersed in the medium. If the liquid of the droplet is of higher density than the immiscible medium, it thereafter sinks into the medium. Where it is of lower density, it floats on the surface of the medium or it ascends in the direction of the surface of the medium.

Where the droplet is dispensed, this may be carried out by any means. As an example, a dispenser may be provided. A dispenser may employ any suitable device or mechanism in order to provide and dispense a droplet of a desired size. Examples include, but are not limited to, piezoelectric pipettors, piezo-activated pipettes, syringe pump-based pipettors, peristaltic pumps, touch-off dispensing, inkjet dispensing (including syringe-solenoid dispensing), and pin-transfer (cf. Rose, D, *Drug Discovery Today* (1999), 4, 411-419 for a review). By means of the dispenser the droplet may in one embodiment be disposed onto the surface of the immiscible medium without contacting the same, above a hydrophilic surface area of an immobilisation member. In another embodiment, for instance where the density of the droplet liquid is lower than the medium in the processing compartment, the droplet may be dispensed anywhere onto the surface of the immiscible medium (without contacting the same) and subsequently be positioned above a hydrophilic surface area by means of a magnetic or an electric field (including an electrostatic field). In yet another embodiment the droplet may be dispensed directly onto the surface of a medium in a processing compartment by means of contact dispensing. Where desired, the dispensed quantities may be measured, e.g. by means of a camera as disclosed in US patent application 2003/0209560.

As indicated above, in some embodiments disposing the liquid droplet onto the at least one predefined immobilisation area includes dispensing the liquid droplet into the processing compartment. The droplet may be dispensed from any location within the processing compartment, including the side walls or a device inserted into the processing compartment. It may be dispensed directly onto the predefined immobilisation area or it may first be dispensed at any other location as defined above and thereafter be directed to the predefined area. In some embodiments the droplet is dispensed into the medium. In some embodiments the droplet is dispensed onto the surface of an immobilisation member, in the presence or absence of any medium. In some embodiments a nozzle of a dispenser may be embodiment the method includes exposing the droplet to a magnetic field. In yet another embodiment the method includes exposing the droplet to both a magnetic and an electric field such that the droplet is forced to be allowed or forced to enter the medium and to pass through it toward the immobilisation member. In another embodiment the droplet is allowed to enter the medium by means of gravity. Typically in this embodiment the droplet is heavier than the medium that is included in the processing compartment. In yet another embodiment allowing the liquid droplet to enter the medium and to pass through it toward the immobilisation member includes exposing the droplet to any combination of an electric field, an electrostatic field, a magnetic field, and gravity.

In some embodiments the droplet is allowed or forced to pass through the medium and to contact the immobilisation member by means of an electric/magnetic field. In some embodiments of the method, the electric/magnetic field is terminated, after the droplet is immobilised on the predefined immobilisation area of the immobilisation member. Where desired, a liquid droplet may be neutralized after charging. This may for instance be desired to enhance the stability of the interfacial interactions immobilising the liquid droplet on the predefined immobilisation area of the immobilisation member. Discharging can be performed by means of commercially available devices, such as Simco's V-Block electrostatic charger. For discharging, both positive and negative ion generators become active and generate ample charges of both signs for neutralization. It should be noted that for neutralization purposes, ample amounts of both positive and negative charges ought to be provided to a target object. Depending on the selected configuration of a charge generator and chip apparatus, neutralization can happen locally or throughout the entire chip apparatus.

In typical embodiments the process (see also below) is only performed once the liquid droplet has been immobilised on the predefined immobilisation area of the immobilisation member. In some embodiments the process may nevertheless be started or performed at an earlier point in time, for instance once the droplet has been allowed to enter the medium that is immiscible with the liquid of the liquid droplet.

In some embodiments of the method of the invention, exposing the droplet to an electric/magnetic field includes repelling the droplet. In some of these and in other embodiments exposing the droplet to an electric/magnetic field includes attracting the droplet. Attracting and/or repelling the droplet by means of an electric field may for instance be achieved by means of electrodes. In some embodiments a respective electrode is included in a device of the invention (supra), for example in form of an electro-chip (e.g. FIG. 4F).

In embodiments where a magnetic field is applied, the droplet may include magnetically attractable matter, such as particles. In such a case exposing the droplet to a magnetic field exerts a force on the magnetically attractable matter, such that the droplet as a whole is forced to enter the medium and to pass through it toward the immobilisation member. The droplet may be attracted or repelled by a magnetic field in a similar manner as a charged droplet in an electric field (including an electrostatic field). In some embodiments the magnetic field is applied before the droplet enters the medium. In other methods the droplet is allowed to reach the medium, in some embodiment including to enter it, by means of a force different from a magnetic field. In such embodiments the magnetic field may be used only in addition to such other force to assist directing the liquid droplet to the predefined immobilisation area on the patterned surface of the immobilisation member. In other embodiments allowing the droplet to enter the medium and to pass through it toward the immobilisation member, are achieved by means of a magnetic field. In some embodiments the magnetic field is terminated once the interfacial, e.g. hydrophilic-hydrophilic, interactions immobilise the liquid droplet on the predefined immobilisation area of the immobilisation member. The droplet remains immobilised on the predefined immobilisation area since the buoyancy force on the droplet is not strong enough to release the droplet. The magnetically attractable matter used in such embodiments may be magnetic particles that provide a surface with an affinity for certain matter allowing for instance to absorb/adsorb proteins, peptides, nucleic acids and other compounds (see below).

As described above, in some embodiments the immobilisation member of the apparatus of the invention provides a plurality of predefined immobilisation surface areas as defined above, for instance a plurality of hydrophilic surface areas. Accordingly a respective apparatus may be used in the method of the present invention. Such embodiments of the method of the invention may include disposing a plurality of liquid droplets onto the plurality of predefined, e.g. hydrophilic, immobilisation surface areas. A plurality of liquid droplet may for instance be dispensed below or above the plurality of predefined immobilisation surface areas, e.g. in a mechanical manner as described above. As mentioned above, the immobilisation member may be removable from the reservoir and be inserted therein only after the liquid droplets have been disposed on the immobilisation member. A single dispenser may for instance consecutively dispense liquid droplets at selected locations in a processing compartment, or a plurality of dispensers may be employed at a same time. As an illustrative example, one or more nozzles of one or more dispensers may be used to dispense a plurality of droplets directly onto a plurality of predefined immobilisation surface areas with a relatively high surface energy. Where desired, disposing liquid droplets may be carried out in parallel. Each droplet of a respective plurality of liquid droplets may include a biological and/or chemical sample, for instance a sample from different origin. A process may be performed on any number of the samples in said plurality of liquid droplets. In some embodiments a different process is performed on different samples; in some embodiments the same process is performed on different samples. In one of these embodiments all samples are processed concurrently in parallel, so that a process, including a plurality of processes, is performed in the plurality of liquid droplets in parallel.

In some embodiments, in particular where the predefined immobilisation surface area on the immobilisation member includes a molecule with a linking moiety, the method further includes immobilising target matter, such as a target molecule, on the plurality of immobilisation surface areas. This may for example be achieved via the linking moiety, whether by way of formation of a complex or by means of a covalent bond. Any matter may be the target matter and any molecule may likewise be selected as a target molecule. As an illustrative example, target matter may be an analyte that is included in a sample, for example a sample derived from human or non-human animals, plants, bacteria, viruses, spores, fungi, or protozoa, or from organic or inorganic material of synthetic or biological origin. A respective analyte may for instance be a protein, a nucleic acid molecule, a solvent molecule, a pesticide molecule, a saccharide molecule, an allergen, a hormone, a virus or a cell.

In some embodiments a detectable marker may be coupled to or included into (for an incorporation of a marker within a protein/peptide chain see e.g. Popp, M. W., et al., *Nature Chemical Biology* (2007) 3, 11, 707-708) a molecule with a linking moiety. This may for instance be carried out to monitor the deposition of the respective molecule with a linking moiety. The available linking moieties may be reacted to any degree. Using a low concentration or amount of a respective marker, a selected percentage of linking moieties may for example remain available for a reaction with a target molecule or for a conversion to another linking moiety (see above). A respective marker compound may also be included in a reagent used for the conversion of a linking moiety to another linking moiety. Such a marker may be an optically detectable label, a fluorophore, or a chromophore. Examples of suitable labels include, but are not limited to, an organic molecule, an enzyme, a radioactive, fluorescent, and/or chromogenic moiety, a luminescent moiety, a hapten, digoxigenin, biotin, a metal complex, a metal and colloidal gold. Accordingly a radioactive amino acid, fluorescein isothiocyanate, 5,6-carboxymethyl fluorescein, Texas red, nitrobenz-2-oxa-1,3-diazol-4-yl, coumarin, dansyl chloride, rhodamine, amino-methyl coumarin, Eosin, Erythrosin, BODIPY®, Cascade Blue®, Oregon Green®, pyrene, lissamine, xanthene, acridine, oxazines, phycoerythrin, Cy3, Cy3.5, Cy5, Cy5.5, and Cy7enzymes, alkaline phosphatase, soybean peroxidase, or horseradish peroxidase may serve as a few illustrative examples.

As indicated above, the liquid droplet may include a magnetically attractable particle. For convenience a magnetically attractable particle is herein referred to as a "magnetic particle" or "magnetic bead". A magnetic particle may contain diamagnetic, ferromagnetic, paramagnetic or superparamagnetic material. Superparamagnetic material responds to a magnetic field with an induced magnetic field without a resulting permanent magnetization. Magnetic particles based on iron oxide are for example commercially available as Dynabeads® from Dynal Biotech, as magnetic MicroBeads from Miltenyi Biotec, as magnetic porous glass beads from CPG Inc., as well as from various other sources, such as Roche Applied Science, BIOCLON, BioSource International Inc., micromod, AMBION, Merck, Bangs Laboratories, Polysciences, or Novagen Inc., to name only a few. Magnetic nanoparticles based on superparamagnetic Co and FeCo, as well as ferromagnetic Co nanocrystals have been described, for example by Hütten, A. et al. (*J. Biotech.* (2004), 112, 47-63).

The magnetic particle may be capable of binding target matter that is suspected or known to be included in the biological and/or chemical sample, for example via a ligand included in the magnetic particle. The magnetic particle may be designed to serve the function of attracting target matter through chemisorption, e.g. a covalent bond, or physisorption, e.g. electrostatic attraction. A magnetic particle used in such embodiments may provide a surface with an affinity for certain matter allowing for instance to absorb/desorb proteins, peptides, nucleic acids and other compounds. Examples include, but are not limited to, attractions by physical means, such as e.g. π-stacking, dipole-dipole, induced dipole-dipole, van-der-Waals, opposite charges, or H-bonding, e.g. antibody-antigen binding attractions, and affinity attractions formed between a ligand that has binding activity for the target matter and the target, such as for instance a ligand and a metal. As two further illustrative examples, physicochemical bonds, e.g. between gold and a thiol, or geometrical means, e.g. size exclusion, may be relied on. Different areas of the same or several magnetic particles may also be designed to attract or "capture" the target matter.

In embodiments where the magnetic particle includes a ligand that is capable of binding target matter that is suspected or known to be included in the biological and/or chemical sample, a respective ligand may solely or together with the residual particle be able to bind the target matter. Such a ligand may in some embodiments be capable of selectively binding such target matter such as, but is not limited to, an ion, a polyion, a metal, DNA, RNA, a protein (including a synthetic analogue thereof), bacterial cells, spores, viruses, low molecular weight organic molecules, or inorganic compounds. A respective ligand may be immobilised on the surface of the magnetically attractable particle.

A respective ligand may for instance be hydrocarbon-based (including polymeric) and include nitrogen-, phosphorus-, sulphur-, carben-, halogen- or pseudohalogen groups. It may be an alcohol, an organic acid, an inorganic acid, an amine, a phosphine, a thiol, a disulfide, an alkane, an amino acid, a peptide, an oligopeptide, a polypeptide, a protein, a nucleic acid, a lipid, a saccharide, an oligosaccharide, or a polysaccharide. As further examples, it may also be a cation, an anion, a polycation, a polyanion, a polycation, an electrolyte, a polyelectrolyte, a carbon nanotube, carbon nanofoam, a silica particle, a glass particle, or an alumosilicate. Generally, such a ligand has a higher affinity to the target matter than to other matter. Examples of a respective ligand include, but are not limited to, a crown ether, an antibody, a fragment thereof and a proteinaceous binding molecule with antibody-like functions (see above for examples). Such a ligand may include further elements such as a nucleic acid, in particular in embodiments where the ligand is or includes an antibody, an antibody fragment or a proteinaceous binding molecule with antibody-like functions. As an illustrative example, an antibody-DNA chimera may be used (see Burbulis, I., et al., *Nature Methods* (2007 DOI: 10.1038/NMETH1127). The use of such an antibody-DNA chimera may for example be desired for quantification purposes (ibid.).

Further examples of a suitable ligand include, but are not limited to, a molecular imprinted structure, an extracellular matrix, a lectin, protein A, protein G, a metal, a metal ion, nitrilo triacetic acid derivates (NTA), RGD-motifs, dextranes, polyethyleneimine (PEI), polyelectrolytes, redoxpolymers, glycoproteins, aptamers, enzymes, a dye, streptavidin, amylose, maltose, cellulose, chitin, glutathione, calmodulin, gelatine, polymyxin, heparin, NAD, NADP, lysine, arginine, benzamidine, poly U, or oligo-dT. Lectins such as Concavalin A are known to bind to polysaccharides and glycosylated proteins. An illustrative example of a dye is a triazine dye such as Cibacron blue F3G-A (CB) or Red HE-3B, which specifically bind NADH-dependent enzymes. Green A binds to CoA proteins, human serum albumin, and dehydrogenases. The dyes 7-aminoactinomycin D and 4',6-diamidino-2-phenylindole bind to DNA. Cations of metals such as Ni, Cd, Zn, Co, or Cu, are typically used to bind affinity tags such as an oligohistidine containing sequence, including the hexahistidine or the His-Asn-His-Arg-His-Lys-His-Gly-Gly-Gly-Cys tag (MAT tag), the hexapeptide His-Ser-Gln-Lys-Val-Phe (binding cadmium), and N-methacryloyl-(L)-cysteine methyl ester. In addition a magnetic particle may be coated with a modifying agent that further increases the affinity of the substrate for any or a certain form, class etc. of target matter.

In some embodiments the target matter is a molecule that is suspected or known to be present within other (undesired) matter, from which it needs to be extracted. Extraction of a molecule from an organism, a part of an organism, or an embryo may for instance include the usage of a compound that facilitates the transfer of a desired molecule from an organism or a part thereof into a liquid. An illustrative example of an extraction of a molecule from a part of an organism is an extraction of proteins (wholly or partly) integrated into the cell membrane. It is often desired to transfer such proteins into an aqueous solution for further processing. A compound that facilitates the transfer of such proteins into an aqueous solution is a detergent. Contacting a respective cell membrane with an aqueous solution, to which a detergent is added, will typically result in an extraction of membrane proteins.

Where magnetic particles are used, they may at the same time be acting as a carrier for target matter, or alternatively thereto, themselves act as a tag or amplifier in the context of sensor technologies. Examples include, but are not limited to, giant magnetoresistance (GMR) [Chiriac, H, et al., *Journal of Magnetism and Magnetic Materials* (2005) 293, 671-676], surface enhanced Raman spectroscopy (SERS), enhanced surface plasmon resonance (eSPR), and two-dimensional capillary electrophoresis. As an illustrative example, target matter may be bound to ligands immobilised on different magnetic particles in a liquid droplet according to the present invention. By means of further affinity ligands, whether bound on a stationary phase, in solution, or otherwise the target matter may be separated together with the magnetic particles bound thereto. Where the magnetic particles are exposed to a magnetic field, they develop a dipole field. This dipole field may be detected by a dipole sensor. By quantifying the amplitude of the sensor impedance the amount of target matter can be quantified.

Where a method according to the present invention is to be combined with another method such as an analytical or preparative method (see also below), it may be desired to provide a surface that allows, or is advantageous for, carrying out both such a further method and a method according to the present invention. The availability of various suitable liquids for the droplet used in the present invention typically allows for a flexible selection of a chemical surface treatment, including a coating. Therefore often the same surface can be used during both the method of the present invention and a subsequent method.

As an illustrative example, it may be desired to perform an electrophoretic separation or an isoelectric focussing, for instance by subjecting the magnetic particles, whether included in the liquid droplet used in the present invention or not, thereto. It may for instance be desired to provide a surface with minimal interactions for any matter present, which is detectable by the selected method. Where it is for instance desired to analyse the purity of an isolated protein by applying an electromagnetic field (such as an electrophoretic method), analysis results may be falsified by a surface that significantly interacts with proteins. Two illustrative example of a suitable surface coating with minimal protein interactions are the polar polymer poly-N-hydroxyethylacrylamide and poly (ethylene glycol)-terminated alkyltrichlorosilane. It is likewise known that the properties of a surface of a device used for isoelectric focusing affect the efficiency for obtaining narrow isolated zones during both the focusing and mobilization processes. Examples of surface treatments that may be used to achieve a high separation using a pH gradient in isoelectric focusing include, but are not limited to, a highly polar polymer coating such as polyacrylamide, polyvinylpyrrolidone, polyethylene glycol, poly(vinyl) alcohol, or a fluorocarbon coating.

In some embodiments where at least two immobilisation members with a patterned surface are provided, in which the surface is patterned in such a way that it includes at least one predefined immobilisation area, the liquid droplet may be transferred from one immobilisation member to another. The immobilisation surface area(s), which may for instance be hydrophilic, of one immobilisation member may for instance be of a higher surface energy and e.g. higher hydrophilicity, than the residual surface area(s) of the other immobilisation member that is/are of at most about the same surface energy as the medium. In such embodiments the liquid droplet may for instance be moved between two surfaces by means of a magnetic or an electromagnetic field. Upon doing so the liquid droplet may split in that a part thereof remains on the predefined surface area of the first immobilisation member while a further part is transferred to the predefined immobilisation surface area of the second immobilisation member.

As already explained above, in some embodiments the method of the invention includes arranging an inlet member or a cover on a top of the reservoir. After such an arrangement the apparatus includes an inlet member or a cover removably arranged on a top of the reservoir. The inlet member includes an upper inlet (supra) and may include a guide (supra). In some embodiments the method of the invention may include positioning a dispenser (e.g. a nozzle thereof) in the guide or driving a dispenser through the guide, thereby for example positioning the dispenser or a nozzle thereof into a desired position. As an illustrative example, the inlet member may be a pipetting guide. In such an embodiment the method may include positioning one or more pipette tips on or in the guiding elements, such as grooves, bores or rails (see also above), of the pipetting guide. A respective pipetting guide may also be used in an embodiment of a method of the invention in which an pipetting workstation, such as an automatic pipettor of a High-Throughput-Screening workstation is employed. A respective inlet member may also be of use while a process is performed on the droplet. The inlet member may for example have an inlet positioned on a top of a droplet. The inlet may be an opening of a size sufficient to allow radiation, e.g. light, to pass that for instance originates from the base of the processing compartment. The size may be adapted to be too small to allow light to pass that did not pass the liquid droplet on its way from the base of the processing compartment. Accordingly such an opening may be suited to allow only radiation to pass that already passed the liquid droplet. Such an arrangement may be suited to assist or improve detection, e.g. an optical measurement.

In some embodiments the reservoir defined by the circumferential wall and the base of the processing compartment can be sealed from the ambience, for example by means of the inlet member and a seal or by means of a cover and a seal (supra). In some embodiments the inlet member or the cover includes a respective seal. In other embodiments the processing compartment includes such a seal. In some embodiments both the processing compartment and the inlet member or the cover include a seal, which may for instance be identical, alike or different. The seal is typically designed to impermeably connect the inlet member to the processing compartment. In some embodiments arranging the inlet member or the cover on a top of the reservoir includes sealing the processing compartment from the ambience. In some embodiments a sealing process is carried out to seal the processing compartment from the ambience (supra).

The method of the invention further includes performing a process on the biological and/or chemical sample in the liquid droplet. Any process may be performed that can be performed in a liquid droplet. In some embodiments the process is performed on the biological and/or chemical sample while the immobilisation member is placed in the medium immiscible with the liquid droplet and the droplet is surrounded by the respective medium. In some embodiments the immobilisation member is removed from the reservoir before performing a process on the biological and/or chemical sample. In such embodiments the immobilisation member may be immersed into any container with the respective medium, such as a petri dish, where it is desired to prevent evaporation. Generally the same assays can be performed on the liquid droplets, regardless of whether they are immersed in a respective medium or not. As already indicated above, a respective process may include rinsing or mixing the liquid droplet, filtering the liquid droplet through another liquid droplet, adding liquid to the liquid droplet or removing liquid from the liquid droplet.

Filtering the liquid droplet through another liquid droplet may for instance be performed by means of moving a smaller droplet containing functionalised superparamagnetic particles with immobilised target matter through a bigger liquid droplet. Typically this process is performed on the predefined surface area of the immobilisation member. In this way undesired components such as for example by-products, impurities, substrates, reagents, solvents or solvent components, salts, enzymes, waste, or buffers, can be diluted in the bigger droplet. Upon further movement of the magnetic particles out of the bigger droplet, essentially only the superparamagnetic particles including the immobilised target matter are being removed from the bigger droplet, while most of the undesired matter is being left behind. In this way it is possible to substantially remove matter from the liquid droplet that is not immobilised by the magnetic beads. The underlying purification effect resembles the mechanism known from affinity chromatography, where target matter is held back by functionalized column material forming the stationary phase, and rinsed/washed several times with a washing solution, forming the mobile phase. In contrast to affinity chromatography, in the method of the present invention the washing solution is the stationary phase, while the functionalised material is the mobile phase. It should furthermore be noted that no dead volume occurs using the method of the present invention. Furthermore, in contrast to affinity chromatography, filtering using the method of the present invention allows for the elution of target matter in nanoliter volumes. This advantage is crucial in applications such as biosensing, when for example a high concentration of target matter is present in tiny volumes, or where fast kinetics are to be analysed.

Performing a process on the biological and/or chemical sample in the liquid droplet may also include exposing a liquid droplet that is only partially covered with medium to air of the ambience for a predefined period of time. Thereby partial evaporation of the liquid droplet may be allowed to occur. As an illustrative example, an agglutination of an antibody, immobilized on a metal particle and an analyte molecule may be allowed to occur, for instance in the presence of latex particles. Volume reduction of the liquid droplet by evaporation may then cause a detectable cluster formation as described by Rastogi & Velev (2007, supra).

A respective process may furthermore for instance include an exposure to an altered temperature, an (altered) magnetic field, an (altered) electrical field (including an electrostatic field), an (altered) electromagnetic field, an altered pressure, an (altered) wavelength, an (altered) frequency, an (altered) amplitude, an (altered) chemical concentration, and an (altered) chemical composition (including an altered medium in the processing compartment).

Examples of processes that may be performed include, but are not limited to, a physical detection of target matter suspected or known to be included in the sample, a chemical reaction, a cell lysis, an extraction of a molecule from an organism or a part of an organism, a release of a molecule from an organism, and any combination thereof. Examples of a physical detection include, but are not limited to, a spectroscopic, a photochemical, a photometric, a fluorometric, a radiological, an acoustical, an electrochemical, a colourimetrical, a diffractional, an interferometrical, an elipsometrical, and a thermodynamic detection and include for instance the use of photoactive, fluorescent, radioactive, enzymatic or electrochemically active labels. Two illustrative examples of a spectroscopic method are Raman microscopy and coherent anti-Stokes Raman scattering (CARS) microscopy. The latter technique is for example suitable for selective imaging of specific molecules of interest. Examples of a chemical reaction include, but are not limited to, a chemical synthesis, a chemical degradation, an enzymatic synthesis, an enzymatic degradation, a chemical modification, an enzymatic modification, an interaction with a binding molecule, and any combination thereof. Examples of an enzymatic synthesis include, but are not limited to a protein synthesis, a nucleic acid synthesis, a peptide synthesis, a synthesis of a pharmaceutical compound, and any combination thereof. The method of the invention is for example compatible with any biochemical transformation or assay format, e.g. the yeast-two-hybrid system, small interfering RNA (siRNA), transfection, ligation, etc.

As mentioned above, performing a process may include an exposure to energy, for instance for a process to be initiated or catalyzed. Examples of energy that may be applied, include, but are not limited to, infrared radiation, microwave radiation, or photolytic energy. As an illustrative example, the surface together with a liquid droplet may be placed biochip on a thin film cooler/heater. Accordingly, chemical synthesis driven by elevated temperatures or requiring reduced temperatures may for instance be performed by adjusting the temperature of the environment of the droplet respectively. As another example, temperature-controlled biochemical reactions between about 4° C. and about 100° C. can be performed. Thus, temperature-sensitive biological samples may for instance be stored. Further examples include, but are not limited to, cell isolation, cell incubation, cell lysis, reverse transcription, polymerase chain reaction, and pyrosequencing. Pyrosequencing is a real-time nucleic acid sequencing technique, which is based on the detection of released pyrophosphate during the nucleic acid polymerization reaction (for an overview cf. e.g. Ronaghi, M, *Genome Research* (2001), 11, 3-11). Furthermore, the implementation of diverse optical detection systems, e.g. photodiodes (PD), photomultipliers (PMT), photon counting modules (PCM), spectrometers, and charge-coupled devices (CCDs) allows monitoring these biochemical reactions in parallel and real-time.

As an illustrative example, a pathogen, a bacterium, a virus, or a DNA sequence may be detected using the present invention for identifying a disease state. Diseases which can be detected include, but are not limited to, communicable diseases such as Severe Acute Respiratory Syndrome (SARS), Hepatitis A, B and C, HIV/AIDS, Dengue, swine fever, mouth-and-foot-disease, avian flu, anthrax, *salmonella*, malaria, polio, tuberculosis and influenza; congenital conditions that can be detected pre-natally (e.g. via the detection of chromosomal abnormalities) such as sickle cell anaemia, heart malformations such as atrial septal defect, supravalvular aortic stenosis, cardiomyopathy, Down's syndrome, clubfoot, polydactyl), syndactyl), atropic fingers, lobster claw hands and feet, etc. The present method is also suitable for the detection and screening for cancer, for identifying the pedigree of an animal, e.g. by means of a DNA-tag, or the detection and analysis of substances in blood, e.g. doping.

In other embodiments the method of the present invention may be employed for the detection, reaction (including a binding reaction to a biological cell or a part thereof), synthesis, or any combination thereof, of one or more pharmaceutical compounds, such as drugs. A synthesis of a compound, such as a pharmaceutical compound, may for example be performed as a solid-phase reaction on derivatised beads. Pharmaceutical compounds may for example be used in form of a library. Examples of such libraries are collections of various small organic molecules, chemically synthesized as model compounds, or nucleic acid molecules containing a large number of sequence variants. As an example, each compound of such a library may be disposed into one droplet. Such droplets may be provided in an automated way by commercially available machines, which are well known to those skilled in the art. The method of the invention may for instance be used for drug screening or for determining the presence of a drug in a urine or blood sample.

As a further example, a cell culture media may be suspected to be contaminated (supra). In this case it may be desired to identify the type of contaminant and to use the device of the invention for this purpose. The magnetically attractable matter may in such embodiments for instance be magnetically attractable particles carrying a ligand with an affinity to the contaminant or with an affinity to other matter that has an affinity to the contaminant.

Figure 6:
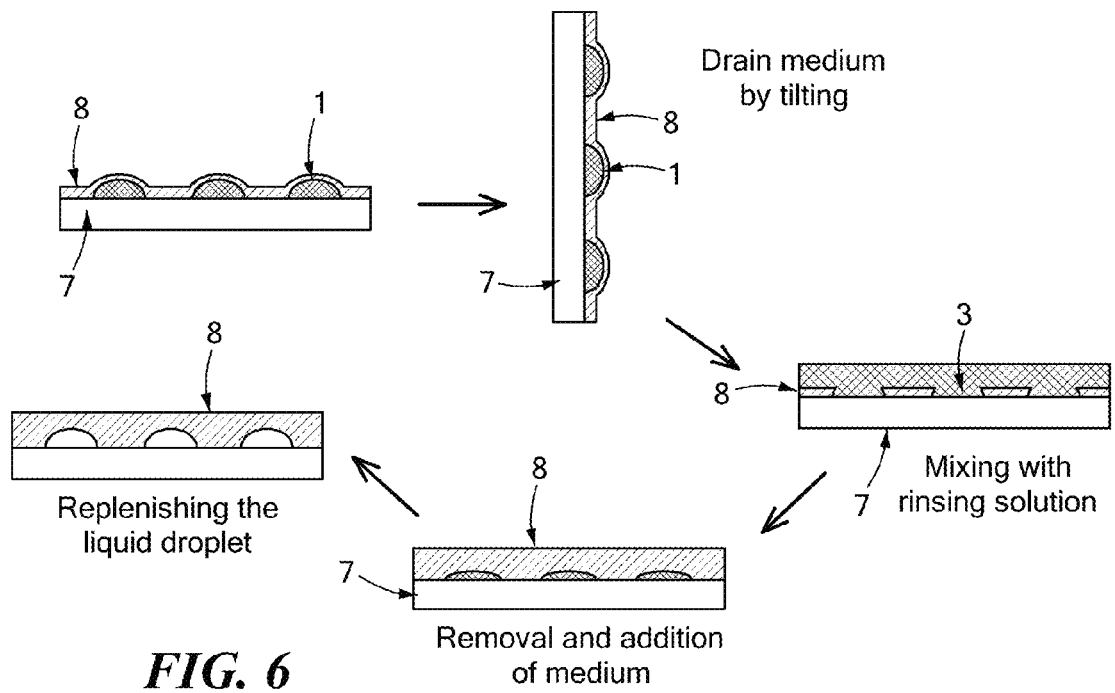
FIG. 6 depicts a general scheme of rinsing and adding liquid.

In embodiments where it is desired to remove matter, such as by-products or undesired matter of the sample, the process may include washing or rinsing. In this way any such undesired matter is washed away, whereas target matter remains immobilised on the surface of the immobilisation member. As an illustrative example, a nucleic acid may be extracted from a cell and be bound by a ligand attached to magnetic particles, while cell debris and reagents are to be discarded. FIG. 6 illustrates an example of rinsing/washing. In some embodiments where washing/rinsing is performed the medium, which is immiscible with the liquid of the liquid droplet (e.g. a hydrophobic medium, see above), is removed from the reservoir before rinsing the liquid droplet, and/or exchanged for a thin fluid medium. A respective thin fluid medium is immiscible with the liquid of the liquid droplet. Furthermore, the thin fluid medium is of a lower surface energy than the liquid of the liquid droplet. As an illustrative example, the thin fluid medium may be of higher hydrophobicity than the liquid of the liquid droplet. In some embodiments the medium that is immiscible with the liquid of the liquid droplet and the thin fluid medium are miscible. The thin fluid medium may be of a lower viscosity than the medium that has been disposed into the apparatus. This may be desired to facilitate the rinsing process. As an illustrative example, the viscosity of the thin fluid medium may be below about 40 centistoke, such as below about 20 centistoke. In some embodiments the boiling point of the thin fluid medium is selected in the range between about 25° C. and about 600° C., such as between about 40° C. and about 400° C.

In some embodiments washing or rinsing of the respective surface or surface area of the immobilisation member includes tilting the immobilisation member. The immobilisation member may also be tilted before rinsing/washing the liquid droplet. Thereby the medium, which is immiscible with the liquid of the liquid droplet, or the thin fluid medium is allowed to at least essentially drain from the immobilisation member. Furthermore, thereby the liquid droplet remains immobilised on the hydrophilic surface area of the immobilisation member. In some embodiments a layer, such as a film, of medium that is immiscible with the liquid of the liquid droplet, e.g. hydrophobic medium, or thin fluid medium, is allowed to remain on the immobilisation member, as depicted in FIG. 6. Thereby the layer of medium is allowed to cover the surface area of the immobilisation member that is of at most about the same surface energy as the medium.

Figure 4B:
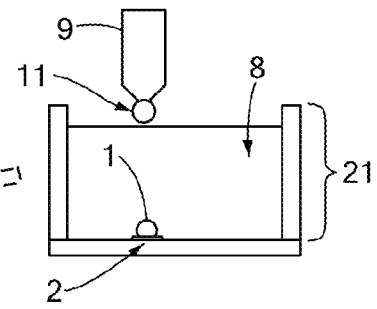
Figure 4C:
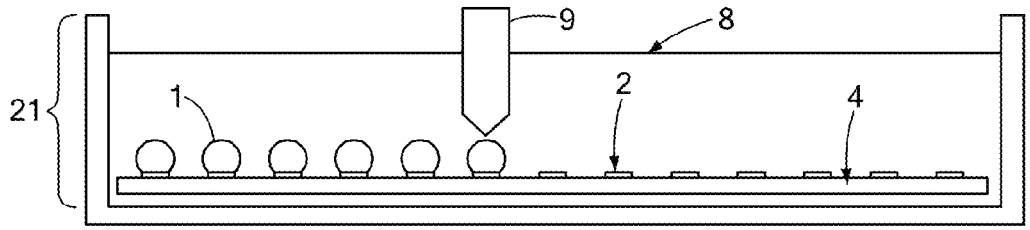
Figure 4D:
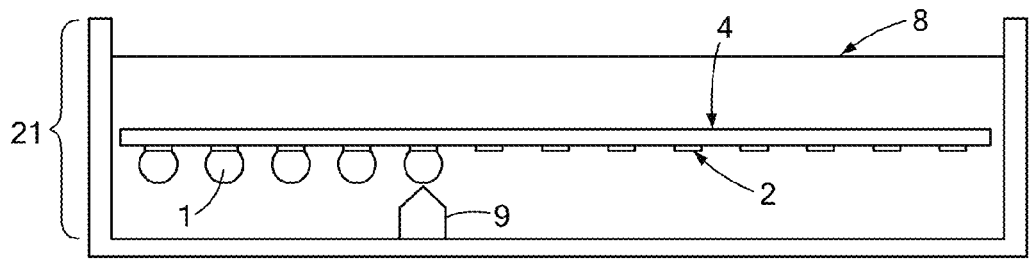

Instead of a bulk phase a further liquid droplet may be employed for rinsing/washing as indicated in FIG. 4B. This further liquid droplet may include any desired liquid. It may be desired to use a liquid that is miscible with the liquid of the liquid droplet. Where the washing/rinsing is performed in the presence of medium, e.g. a hydrophobic medium, it may furthermore be advantageous to use a liquid that is immiscible with the respective medium. Merging the liquid droplet, which is already immobilised on the hydrophilic immobilisation surface area, with a further liquid droplet may also be used to add liquid to the liquid droplet.

In some embodiments such a further liquid droplet may be immobilised on the surface of a further device, which is brought in close vicinity to the immobilisation member. The surface of such a further device may include guidance cues in the form of geometrical elements or a wettability pattern, which may serve in fixing any droplets immobilised on the respective surface, or in providing predefined escape routes for merged droplets to move.

The liquid droplet may also be mixed using the method of the present invention. As an example the immobilisation member may be mechanically shaken. As a further example, in embodiments where the liquid droplet includes magnetic particles, to perform or assist mixing a weak magnetic force may be applied that is sufficient to for instance lift these magnetic particles within the droplet. As yet a further example, mixing may be achieved by means of ultrasound. In yet other embodiments microfluidic devices may be used for washing or mixing, or the apparatus may be equipped with such microfluidic devices. Nevertheless it is understood that the method of the present invention does not require the use of any microfluidic device or mechanism.

In embodiments where the apparatus includes a feeding module (supra), this feeding module may be used to allow the flow of fluid into and/or out of the reservoir in the method of the invention. This may be carried out via a channel, including a port, which may be arranged in the processing compartment. As an example, the feeding module may be used to remove the medium that is immiscible with the liquid of the liquid droplet. It may also be used to add a medium that is immiscible with the liquid of the liquid droplet to the reservoir. In some embodiments a liquid that is miscible with the liquid of the liquid droplet is allowed to flow into the reservoir via the feeding module. Such a liquid that is miscible with the liquid of the liquid may also be allowed to flow out of the reservoir via the feeding module. Thereby the liquid droplet immobilised on the immobilisation member may for example be rinsed or liquid be added thereto. In some embodiments of the method the liquid that is miscible with the liquid of the liquid droplet is allowed to continuously flow into the reservoir via the feeding module. The liquid may for instance be circulated continuously via the feeding module or it may partly or completely be continuously be replaced by fresh liquid.

The possibility to perform transfers of matter such as washing and rinsing allows complex processes to be performed. Since desired target matter may be bound to ligands immobilised on the hydrophilic surface area or on magnetic particles, the possibility to add, remove or exchange liquid, enables the isolation of any matter, e.g. peptides, proteins, DNA, RNA, small organic molecules, metal ions, etc. (supra) at any desired stage or step, and complex biochemical transformations can be carried out in sequence. Furthermore, the volume of the liquid droplet can be changed where required.

Where desired, the concentration of target matter in a sample may be increased by volume reduction according to techniques well known in the art such as gel-filtration, ultrafiltration or dialysis. A low volume as used in the method of the present invention, in particular in combination with a high concentration of target matter, makes biosensing of biomolecules in low absolute numbers possible.

As two further illustrative, but not limiting examples, the method of the present invention may be used to carry out a polymerase chain reaction or immunoassays such as an enzyme-linked immunosorbent (ELISA) assay (for example a sandwich-type ELISA or a competitive ELISA). Other immunoassays include, but are not limited to, particle-based multiplexed immunoassays. The uses and capabilities of these assays are well known to those skilled in the art.

Any part of the method of the present invention may be performed in a manual or in an automated way. Automated distribution of compounds, liquid and reagents, automated incubators and high-performance fluorescence readers, including plate readers, are already well established in the art. Typically, such equipment can directly be used with an apparatus of the present invention. Where required, adaptations of either such equipment or of the apparatus of the invention to a particular application are easily performed by a person skilled in the art.

Figure 11A:
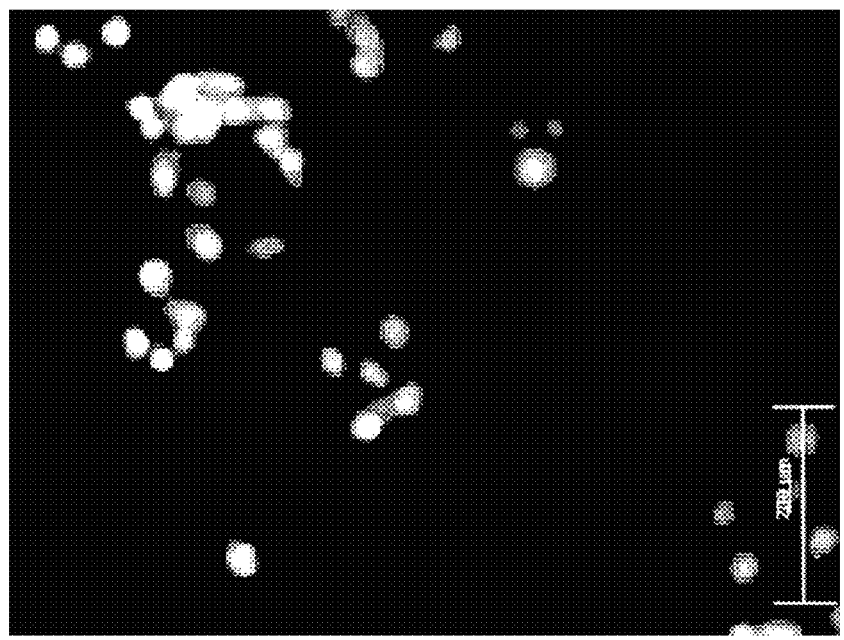
FIG. 11A depicts HepG2-GFP cells expressing the green fluorescent protein.

Real time detection may provide an amplification plot depicting the fluorescence signal versus reaction time expressed as cycle numbers. An increase in fluorescence above the baseline indicates the detection of accumulating amplification product. Where a fixed fluorescence threshold is set above the baseline, the fluorescence signal thus passes this threshold at a certain time point. As time is expressed in terms of cycle numbers, a so called cycle threshold number (or value) or Ct value is obtained. The smaller this number, the further to the left is a respective fluorescence curve located in the amplification plot and the faster does amplification occur. The higher this number, the slower an amplification occurs and the less it becomes distinguishable from non-specific background reactions. An illustration of obtained fluorescence signals using the method of the present invention and is depicted in FIG. 11 (FIG. 11A and FIG. 11B).

The method of the invention may be combined with such analytical and preparative methods, as for instance surface plasmon resonance, resonant mirror, reflectometric interference, giant magneto resistance, mass spectroscopy, ellipsometry, isoelectric focusing, chromatography methods, electrochromatographic, electrokinetic chromatography and electrophoretic methods. Examples of electrophoretic methods are for instance Free Flow Electrophoresis (FFE), pulsed field gel electrophoresis, polyacrylamide gel electrophoresis (PAGE), Capillary Zone or Capillary Gel Electrophoresis. Surface immobilization of magnetic particles by charged proteins is for example known to shift their electrophoretic mobility up to several-fold. The combination with such methods may include a common step or a common device. As an example, a separation of proteins may be performed on a micro chip, for instance by isoelectric focussing. Subsequently a sample of the separation medium, e.g. a solution of ampholytes in water, known or suspected to contain matter, such as a protein, of interest may be used as e.g. the inner phase of a liquid droplet of the present invention. In case of the separation medium being a gel, the matter of interest may need to be extracted. The variety of suitable liquids for the fluid droplet used in the present invention usually allows the selection of a surface material that is well suited for usage as a surface for isoelectric focussing. As a consequence, a common surface may be shared for both methods where desired. Examples of a chromatography method include for instance gel filtration, size exclusion chromatography, ion exchange chromatography, affinity chromatography, hydrophobic interaction chromatography or hydrophobic charge induction chromatography. As an illustrative example, a respective analytical or preparative method may be performed before or after processing a sample using the method of the present invention.

In order that the invention may be readily understood and put into practical effect, particular embodiments will now be described by way of the following non-limiting examples.

EXEMPLARY EMBODIMENTS OF THE INVENTION

Exemplary embodiments of an apparatus and a method of the invention are shown in the appended figures.

FIG. 1 depicts embodiments of a droplet contacting an immobilisation member of an apparatus of the present invention. If a droplet (1) of a hydrophilic liquid is immersed into a medium and contacts the residual, i.e. not predefined, hydrophobic surface (4) of the immobilisation member, it will typically float away from the surface (FIG. 1A). If the droplet however contacts the predefined hydrophilic immobilisation area (2) included in the patterned surface (4), it will be immobilised thereon (FIG. 1B). Multiple droplets may be immobilised on a plurality of hydrophilic immobilisation areas within a patterned surface (with hydrophobic areas) of an immobilisation member (4). This may be carried out in a hydrophobic medium (8) by means of a pipette as a dispenser (9) (FIG. 1C).

FIG. 2A depicts, in cross-sectional view, an embodiment of a device that can be assembled to an apparatus according to the present invention for processing a sample in a liquid droplet. The device (20) includes a reservoir, defined by a transparent glass slip as a transparent base (6) and a circumferential wall (25). The device is adapted to receive a chip that may provide a plurality of hydrophilic areas as an immobilisation member. For this purpose the circumferential wall (25) extends into the interior of the reservoir, thereby forming a step by which an immobilisation member can be supported. FIG. 2B depicts the same device in top view.

Figure 2C:
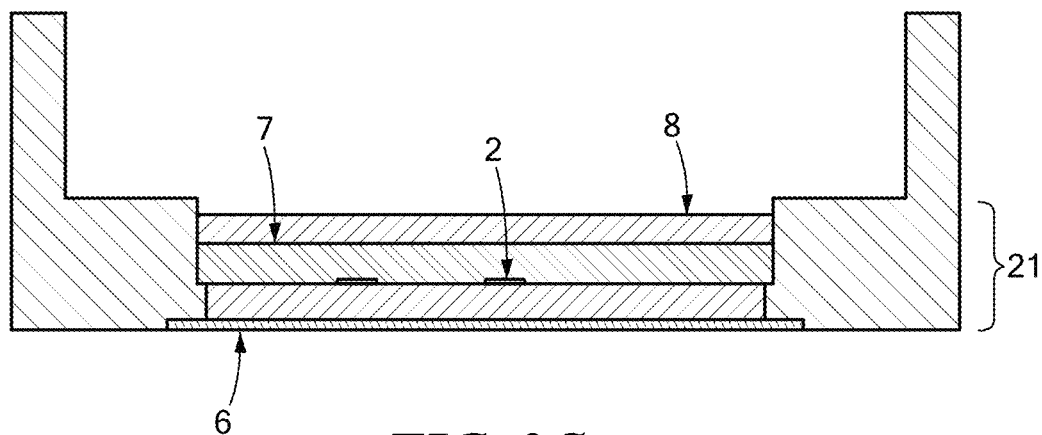
Figure 2D:
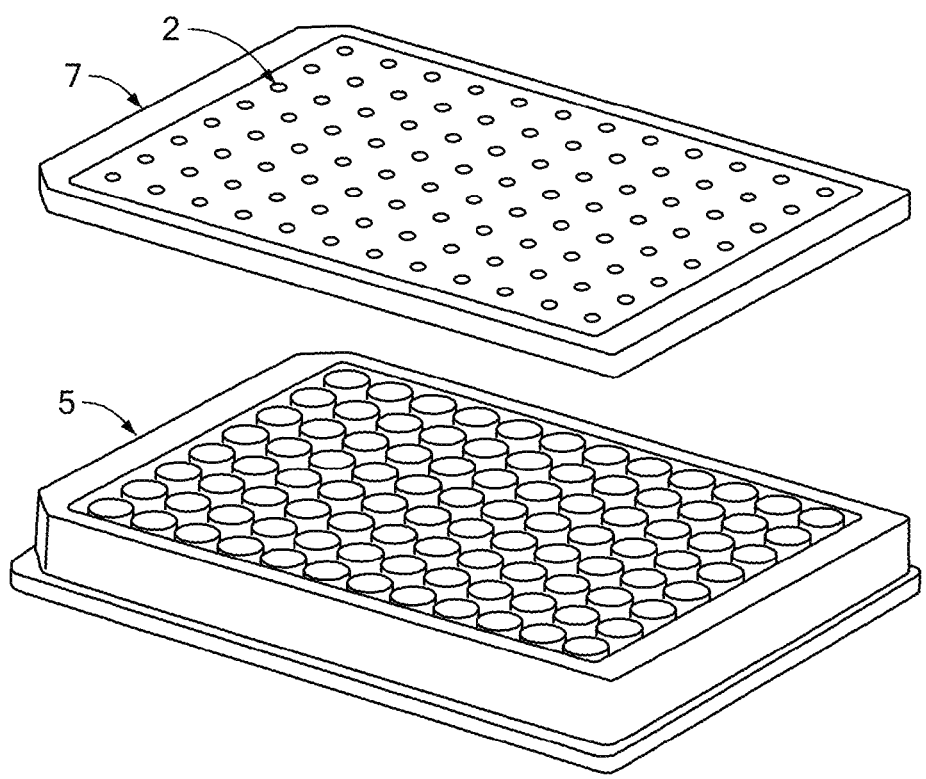

FIG. 2C depicts the assembled apparatus with an inserted chip (7), and accordingly a processing compartment, and hydrophobic medium (8). FIG. 2D illustrates that an immobilisation member (7) may be chosen that matches the dimensions of a conventional 96-well plate (5). It should however be noted that the dimensions of a hydrophilic immobilisation area (2) of the immobilisation member of an apparatus of the invention may differ from those of a well of a multi-well plate. Nevertheless the arrangement of hydrophilic immobilisation areas of an immobilisation member used in the apparatus of the invention may correspond to the arrangement of wells of a 96-well plate. It is furthermore understood that an immobilisation member as it in some embodiments is part of the apparatus of the invention does not need to possess topographic surface differences, such as wells with a bottom, as a conventional multi-well plate, but that it may provide a flat surface.

Figure 2E:
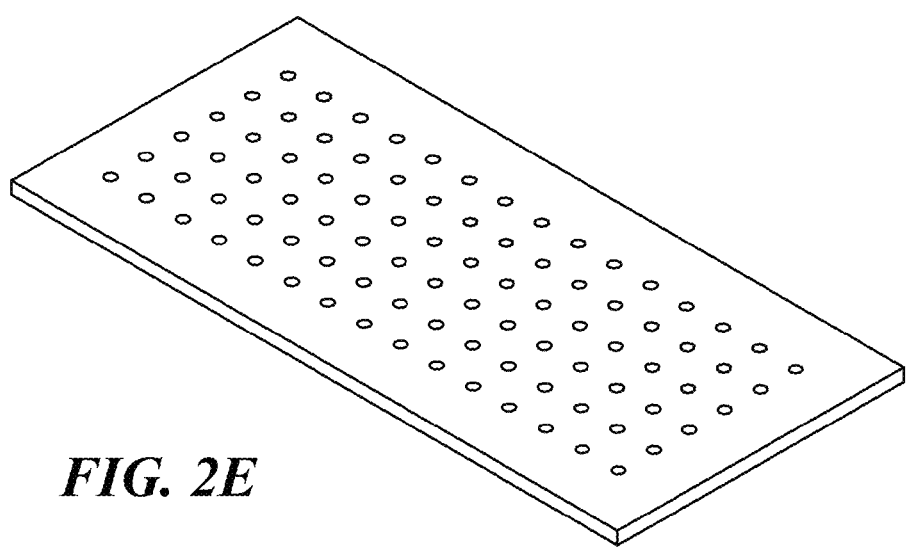
Figure 2F:
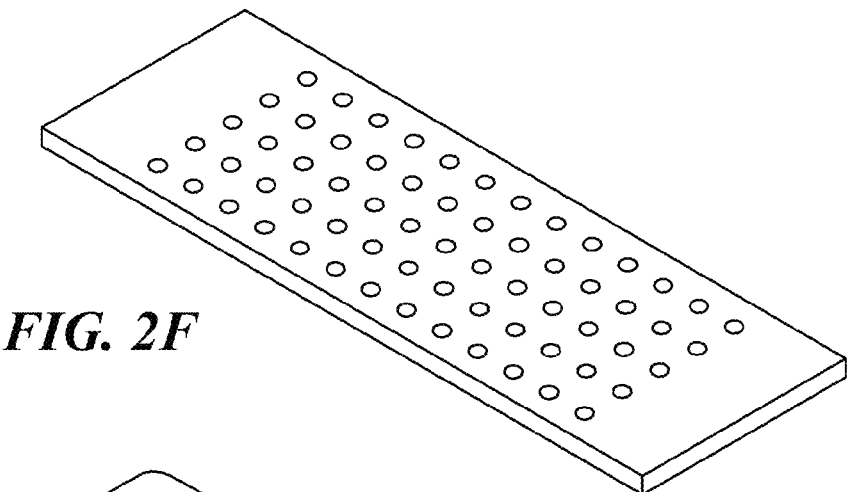
Figure 2G:
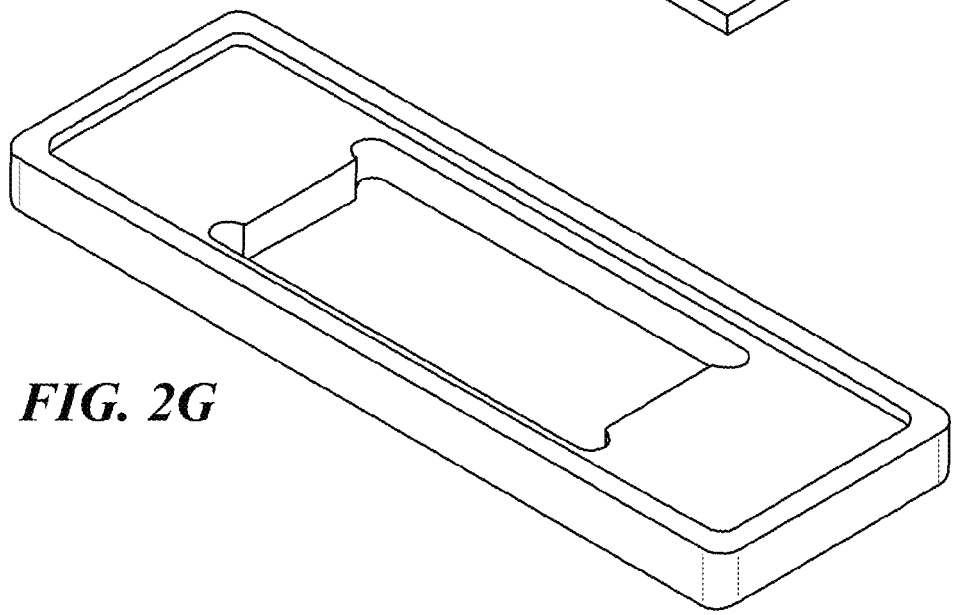
Figure 2H:
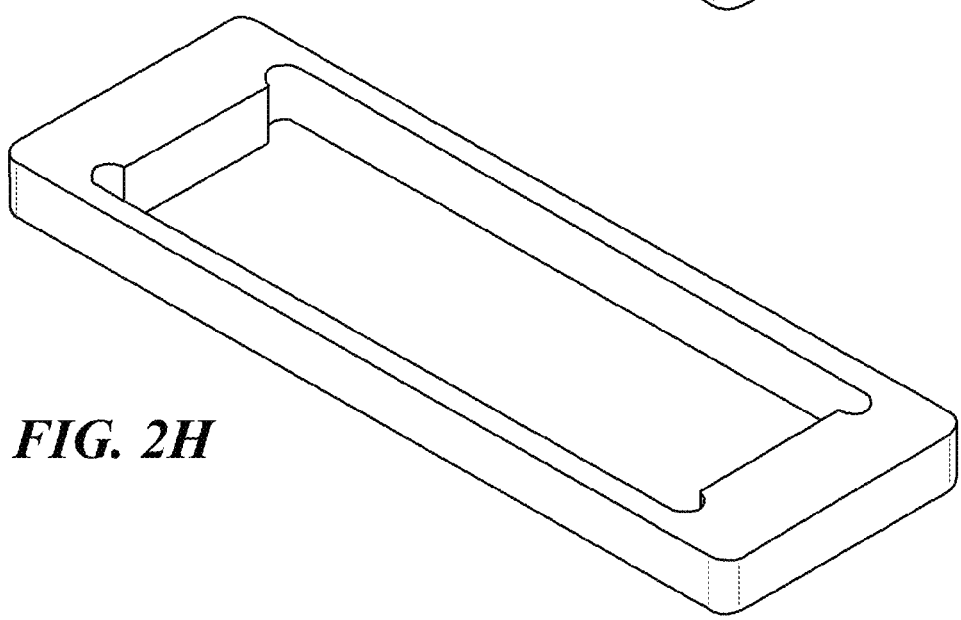

FIG. 2E and FIG. 2F show further embodiments of a respective chip that may be used to form the processing compartment of the apparatus of the invention. All hydrophilic (immobilisation) areas of the depicted chips are of circular shape of identical dimensions and hydrophilicity. The chip of FIG. 2F includes 15×6 hydrophilic areas with a diameter of 500 μm. The chip furthermore has dimensions of 37.8 mm×17.8 mm. The chip of FIG. 2E includes 13×5 hydrophilic areas with a diameter of 2 mm. The chip has dimensions of 75 mm×25 mm. FIG. 2G and FIG. 2H show a chip holder that may be used to fix the immobilisation member in the apparatus of the invention. The chip holder of FIG. 2G has external dimensions of 75 mm×25 mm×5 mm, and a pocket size of 38 mm×18 mm. The chip holder of FIG. 2H also has external dimensions of 75 mm×25 mm×5 mm. It has a pocket size of 60 mm×21 mm.

FIG. 3 illustrates means of disposing a liquid droplet using electric forces. A dispenser (9) may be placed on a top of a hydrophobic medium included in the processing compartment of an apparatus of the invention. The right third of the figure shows an enlargement of a nozzle of an exemplary dispenser (9). The nozzle is positioned above a hydrophilic immobilisation area (2) within the hydrophobic surface of an immobilisation member (4), which is immersed in a hydrophobic medium (8). In the present example, the hydrophilic area (2) is slightly concave to form a recess. Ionized air (symbolized by charges "+" and "−") may be used to charge droplets, for example once they are disposed from the nozzle. A droplet is then charged before entering hydrophobic medium (8) included in the processing compartment of an apparatus of the invention. As a further example, a liquid in a nozzle may be charged before being released therefrom, e.g. through a nozzle. Upon dispensing, a droplet from a dispenser retains charges even after entering the hydrophobic medium.

FIG. 4A depicts a liquid droplet (1) disposed onto a predefined hydrophilic immobilisation area (2) that is included in the patterned surface of the base (6) of the processing compartment of an apparatus according to the present invention. In the depicted example the immobilisation member (7) is an integral part of the base of the reservoir that is included in the apparatus (indicated by the label "6=7"). The liquid droplet has been dispensed from a dispenser (9), located on a top of the immiscible medium (8), and is immobilised on the base of the reservoir.

FIG. 4B illustrates that a liquid droplet immobilised on the hydrophilic immobilisation area (2) of an immobilisation member as depicted in FIG. 4A may also be obtained by merging parent droplets (indicated by the arrow to FIG. 4A). An additional liquid droplet (11) may be disposed onto a hydrophilic immobilisation area (2), on which a liquid droplet (1) is already immobilised. The liquid of liquid droplet (11) is of similar hydrophilicity as the liquid of liquid droplet (1). Upon contacting liquid droplet (1), liquid droplet (11) merges with liquid droplet (1).

FIGS. 4C and 4D depict exemplary schemes of dispensing a liquid droplet onto the hydrophilic area (2), located within a remaining hydrophobic area (4) of the patterned surface by means of a dispenser (9) that is immersed into the immiscible medium (8). In the example depicted in FIG. 4C the liquid droplet is immobilised on top of the immobilisation member, while in the example depicted in FIG. 4D it is immobilised at the bottom of the immobilisation member.

Figure 4E:
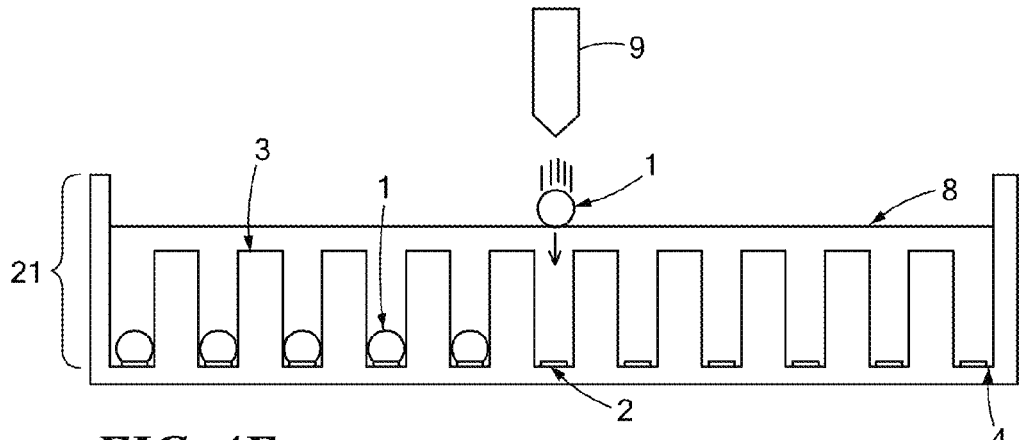

FIG. 4E depicts a further exemplary scheme of disposing a liquid droplet (1) onto the hydrophilic immobilisation area (2) by means of pressure.

Figure 4F:
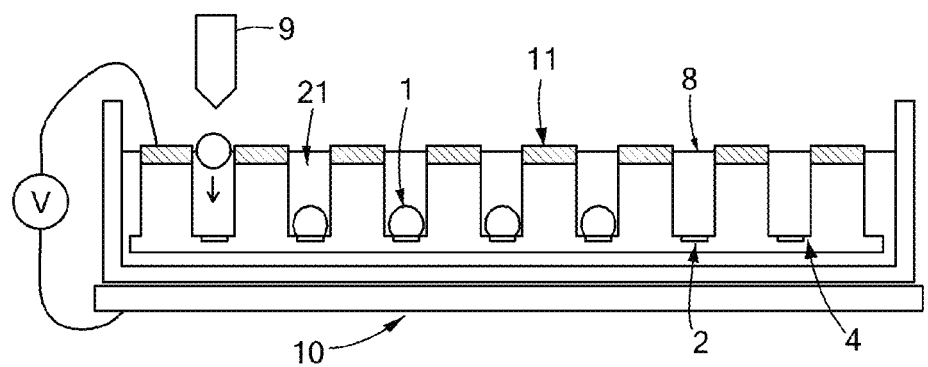

FIG. 4F depicts an exemplary scheme of disposing a liquid droplet (1) onto a predefined hydrophilic immobilisation area (2) of the patterned surface of the immobilisation member, which also includes a residual hydrophobic area, by means of an electric field. The electric field is generated by means of an electrochip (11) and a planar electrode (10). Instead of the electrodes a magnet may be used, where it is desired to apply a magnetic field.

Figure 4G:
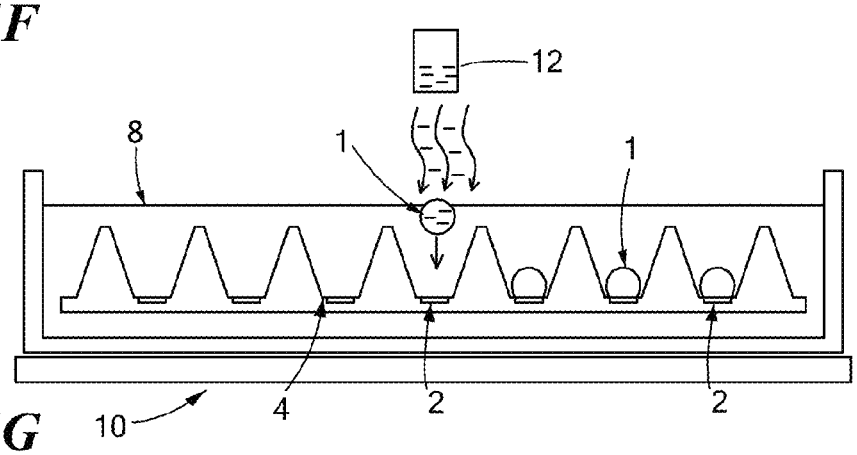

FIG. 4G depicts a further exemplary scheme of disposing a liquid droplet (1) onto the predefined hydrophilic immobilisation area (2) by means of an electric field. The electric field is generated by means of an external electrode (12) and a planar electrode (10).

Figure 4H:
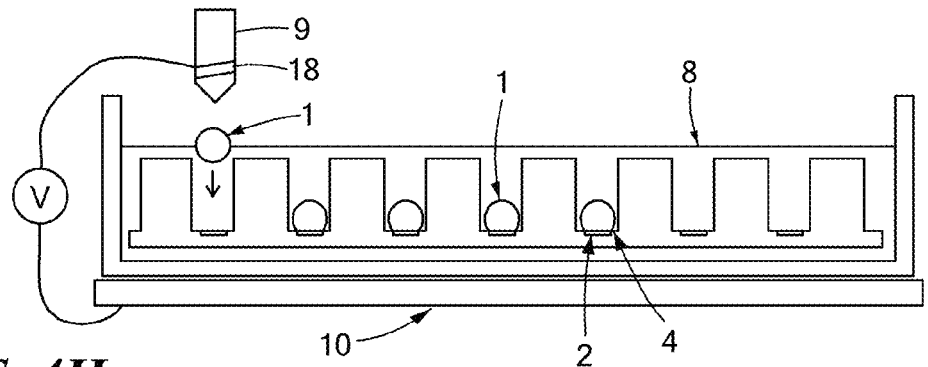

FIG. 4H depicts yet a further exemplary scheme of disposing a liquid droplet (1) onto the predefined hydrophilic immobilisation area (2) by means of an electric field. The electric field is generated by means of wire wrapping (18) the tip of a dispenser and a planar electrode (10).

Figure 4I:
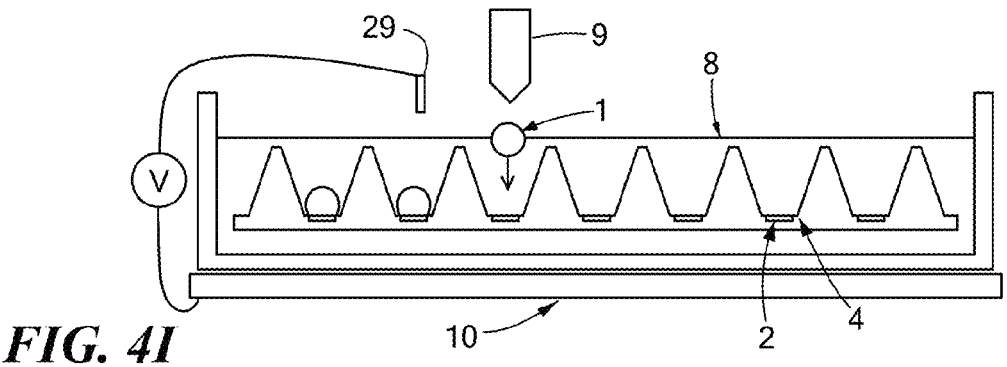

FIG. 4I depicts yet a further exemplary scheme of disposing a liquid droplet (1) onto the predefined hydrophilic immobilisation area (2) by means of an electric field. The electric field is generated by means of a pointy electrode (29), which is adapted to be movable. Upon moving and positioning the pointy electrode (29) above a droplet floating above a predefined hydrophilic immobilisation area (2), the electrode is activated so as to provide an electric field. This forces the droplet to enter the immiscible medium (8), to immerse therein and to pass through the immiscible medium until contacting the hydrophilic area (2). Once the liquid droplet contacts the hydrophilic area (2), it is immobilised thereon.

Figure 5:
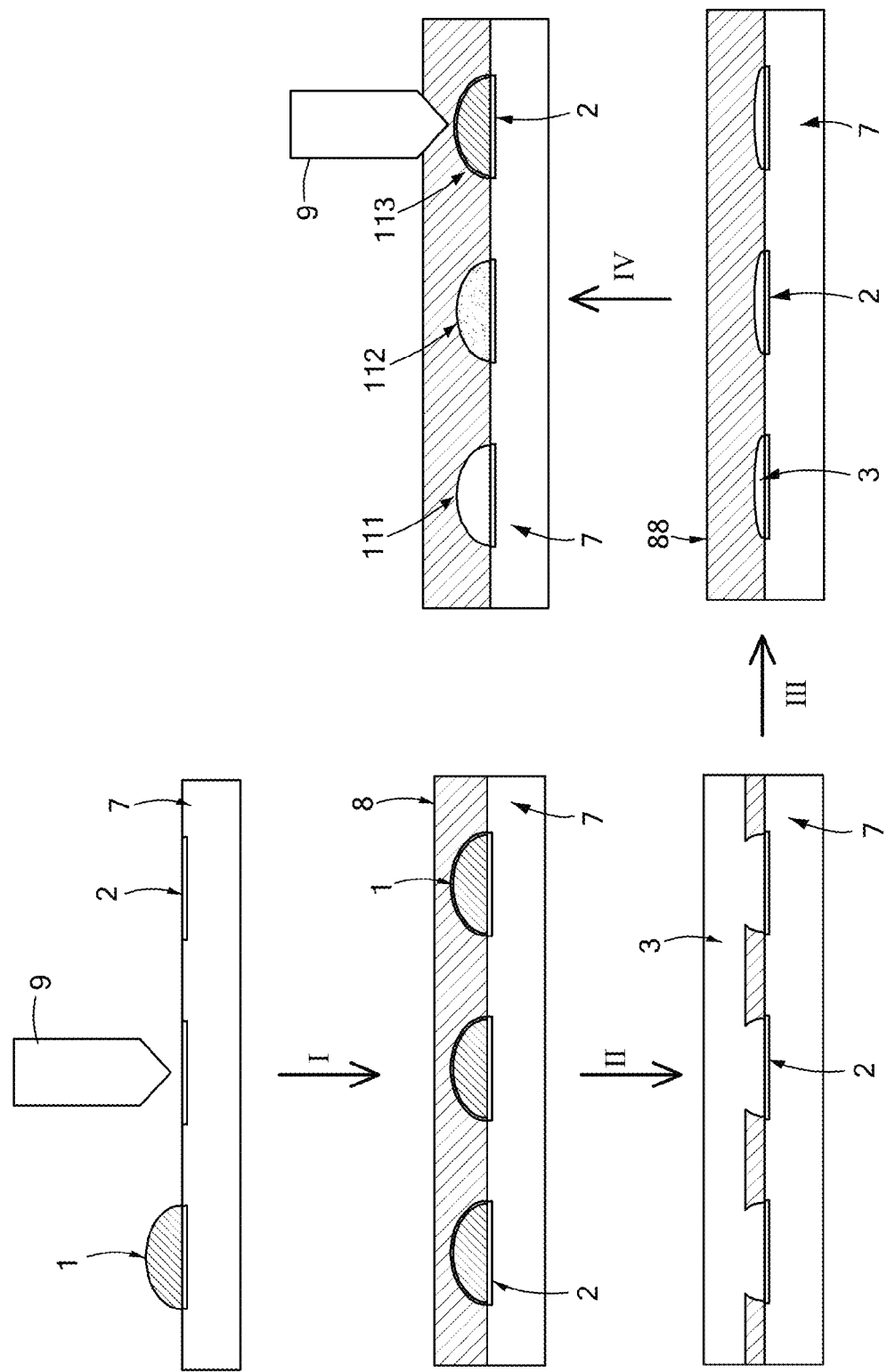
FIG. 5 depicts a further example of immobilizing and rinsing a droplet as well as adding liquid thereto, using the method and apparatus of the present invention.

FIG. 5 depicts an exemplary sequence of immobilizing a droplet, incubation, and rinsing of reagents and samples using the method of the invention. (I): A reagent or sample solution is dispensed onto predefined hydrophilic immobilisation area (2) of an immobilisation member (7) by means of a dispenser (9), in the absence (or presence) of an immiscible medium (8). In the absence of an immiscible medium, the medium is added later, once dispensing liquid droplets with the reagent or sample is completed. The one or more liquid droplets are incubated for a preselected period of time, during which the droplets remain immersed in the immiscible liquid to minimize evaporation. (II): Following the draining of an immiscible liquid, a slide is immersed and shaken in an aqueous rinsing solution (3), whereby the droplets are merged with the rinsing solution (3), while a thin layer of the liquid left from draining prevents the rinsing solution from wetting the hydrophobic surface. (III): Upon removal of the rinsing solution (3), a uniform thin layer of the rinsing solution is left on the predefined hydrophilic immobilisation areas. Subsequently, an immiscible liquid (88) is added to the top of the slide to prevent evaporation of the liquid left at each hydrophilic spot. (IV): A droplet of a fresh solution (111, 112, 113) is dispensed onto the hydrophilic immobilisation areas by means of the dispenser (9).

FIG. 6 depicts a general scheme of rinsing target matter. By means of a rinsing solution. A thin film of rinsing solution remains on each hydrophilic immobilisation area, when a hydrophobic medium accommodates the immobilisation member. The hydrophobic medium is removed by releasing the same from the apparatus or by removing the immobilisation member (7)—including the target matter immobilised thereon—from the reservoir of the apparatus of the invention. To ensure complete removal of the hydrophobic medium the immobilisation member (7) is tilted. Thereby the hydrophobic medium (8) is drained. A layer of hydrophobic medium (8) may be allowed to remain on the immobilisation member, thereby covering the hydrophobic surface thereof. Droplets left on the surface may likewise be covered by a thin layer of hydrophobic medium. Thereafter the immobilisation member is immersed in or exposed to a rinsing solution (3), such that in the present example the contents of all liquid droplets are rinsed. Upon removal from the rinsing solution (3) a layer of rinsing solution may be allowed to remain on the immobilisation member thereby covering the hydrophilic area(s) on its surface as a thin film. The immobilisation member may now be immersed in a hydrophobic medium again. Finally, liquid droplets are replenished on each hydrophilic area by depositing a hydrophilic liquid, e.g. sample, on the hydrophilic immobilisation surface areas of the immobilisation member.

Figure 7:
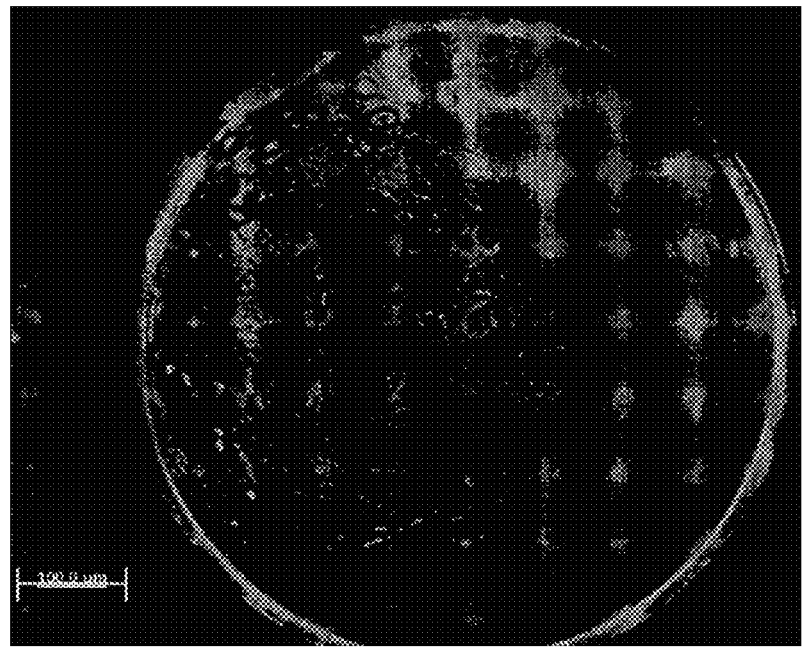
FIG. 7 depicts a photo of NIH3T3 cells grown for 2 days in culture in a droplet immobilised in an apparatus according to an embodiment of the invention.

FIG. 7 depicts a photo of NIH3T3 cells grown for 2 days in culture in a droplet entrapped on an immobilisation member in an apparatus of the invention. The length of the indicated bar (bottom left) corresponds to 100 µm.

Figure 8:
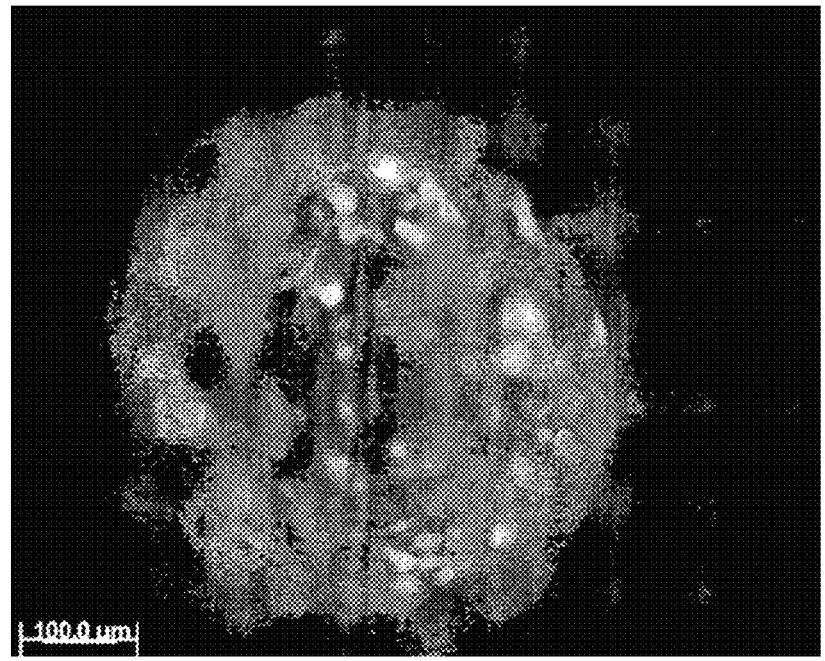
FIG. 8 depicts a photo of NIH3T3 cells as in FIG. 7, the cells being stained with a viability stain.

FIG. 8 depicts a photo of NIH3T3 cells as in FIG. 7, the cells being stained with a viability stain. The signals of the fluorescent viability stain show that the cells are alive and that the apparatus is therefore suitable for handling living cells. The length of the indicated bar (bottom left) corresponds to 100 µm.

Figure 9:
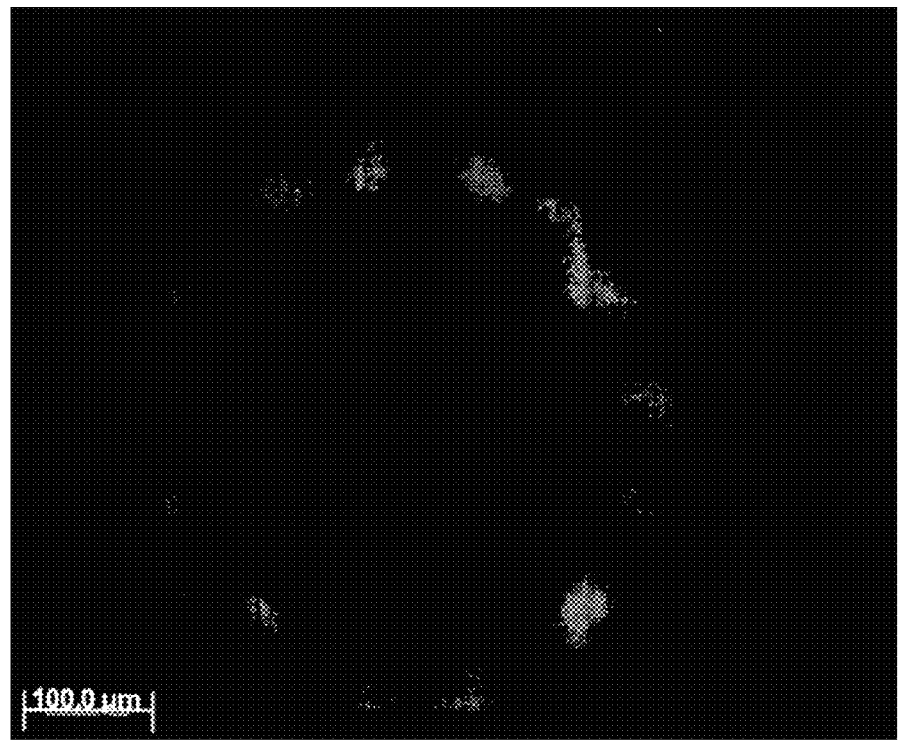
FIG. 9 depicts a photo of NIH3T3 cells as in FIG. 7, the cells being stained with a stain detecting dead cells.

FIG. 9 depicts a photo of NIH3T3 cells as in FIG. 7, the cells being stained with a stain detecting dead cells. The length of the indicated bar (bottom left) corresponds to 100 µm.

FIG. 11A depicts HepG2-GFP cells expressing the green fluorescent protein. The length of the indicated bar (bottom right) corresponds to 200 µm. FIG. 11B depicts an immunofluorescence staining of HepG2-GFP cells using a Ki67 primary antibody, followed by an Alexa-633 conjugated secondary antibody. The length of the indicated bar (bottom right) corresponds to 200 µm.

FIG. 12 depicts fluorescent images of a glass slide patterned with 500-mm features: (1) dispensing of 50 nl of rhodamine dye, (2) washing with PBS buffer, and (3) dispensing of 50 nl of fluorescein dye. The length of the indicated bar (bottom right) corresponds to 500 µm.

Figure 13B:
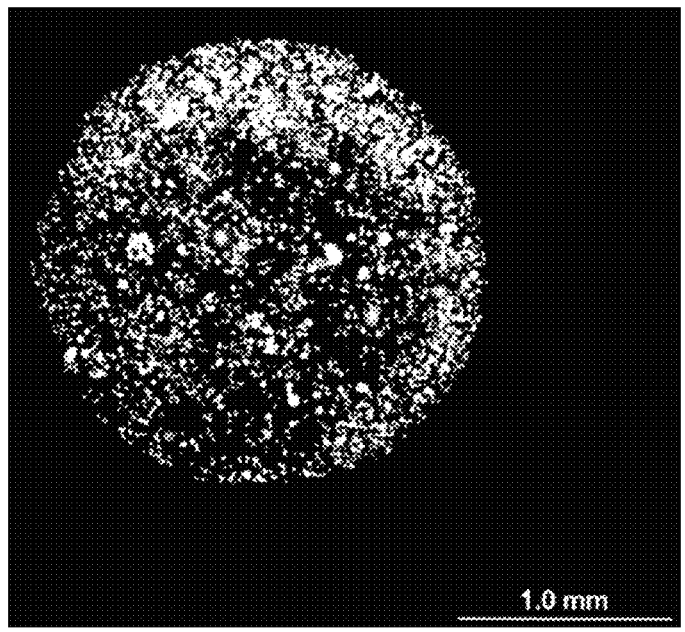
FIG. 13B depicts cells cultured on a patterned immobilisation member according to this embodiment.
Figure 13C:
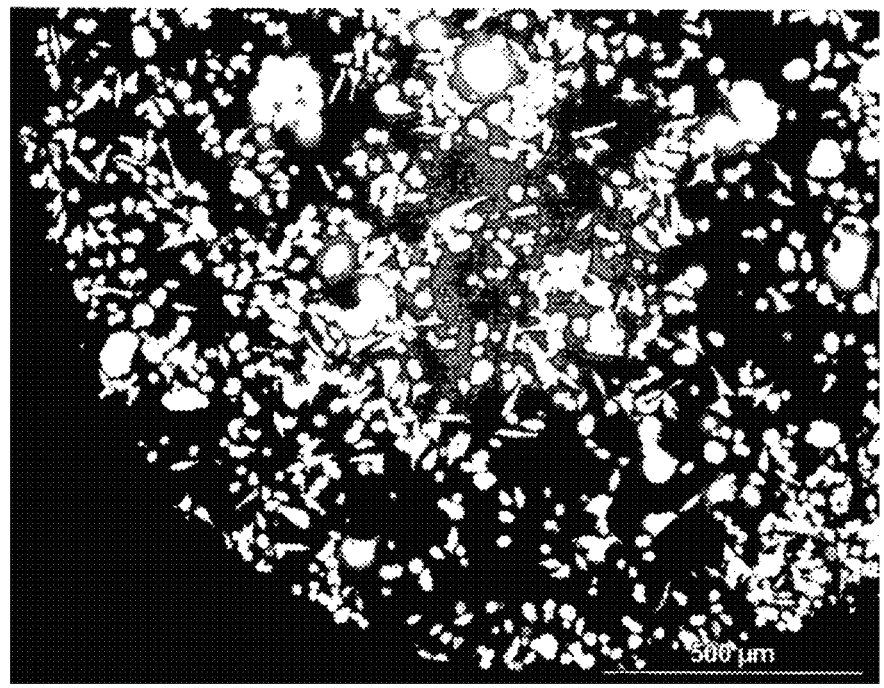
FIG. 13C is an enlargement of a section of FIG. 13B.

FIG. 13A depicts a bulk cell culture in microarray format. The scheme only shows the immobilisation member (7) for simplification purposes. In this embodiment disposing the liquid droplet of cell culture media includes the formation of a first liquid droplet (16) of cell culture media on a hydrophilic immobilisation surface area (2). A hydrophobic medium (8) is disposed onto the remaining, i.e. residual, hydrophobic area of the patterned surface (I). Alternatively, a large amount of PFCL can be added to the chip and drained to leave a thin layer of PFCL on the surface. Thereafter more liquid (13) of the liquid droplet is added to cover the hydrophobic medium (8). This liquid further contains cells (II). Cells settle down at the interface between PFCL and media and on the hydrophilic area of the solid surface. For culturing, the liquid can remain in the reservoir, so that forming a liquid droplet can in this embodiment take an extended period of time. The liquid may also be replaced with fresh liquid as needed, for example, by simple draining and addition with a pipette. Thereafter the liquid can be drained, for example, by tilting or aspiration with a pipette (III). The presence of a thin layer of hydrophobic medium on the remaining, i.e. residual, hydrophobic surface area may be desired in order to prevent the wetting of the hydrophobic surface by a solution such the liquid of the liquid droplet. A rinsing solution (3) may then be filled into the reservoir (IV), released again and replaced by fresh first liquid (13) (V). Where required, cell culture may be continued at this stage. Thereafter, e.g. once the culture of cells is completed, the liquid can again be drained, for example, by tilting or aspiration with a pipette (VI). Thereby a second liquid droplet (1) is formed. The hydrophobic medium (8) may then be replenished, thereby covering the entire liquid droplet (1) (VII). Using this method only cells attached to a solid surface remain upon disposing the liquid droplet. FIG. 13B depicts HepG2 cells expressing the green fluorescent protein (HepG2-GFP), cultured on a glass slide patterned with polytetrafluoroethylene (Teflon). The cells were in Dulbecco's Modified Eagle's Medium (DMEM), containing 1000 mg/L glucose, 10% FBS, 1% penicillin/streptomycin, 0.4 mg/mL of the aminoglycoside antibiotic G418, and 1 mM of the dipeptide L-alanyl-L-glutamine (Glutamax™). The cells were incubated for 4 days. The length of the indicated bar (bottom right) corresponds to 1 mm. FIG. 13C is an enlargement of a section of FIG. 13B. The length of the indicated bar (bottom right) corresponds to 500 µm.

Figure 14A:
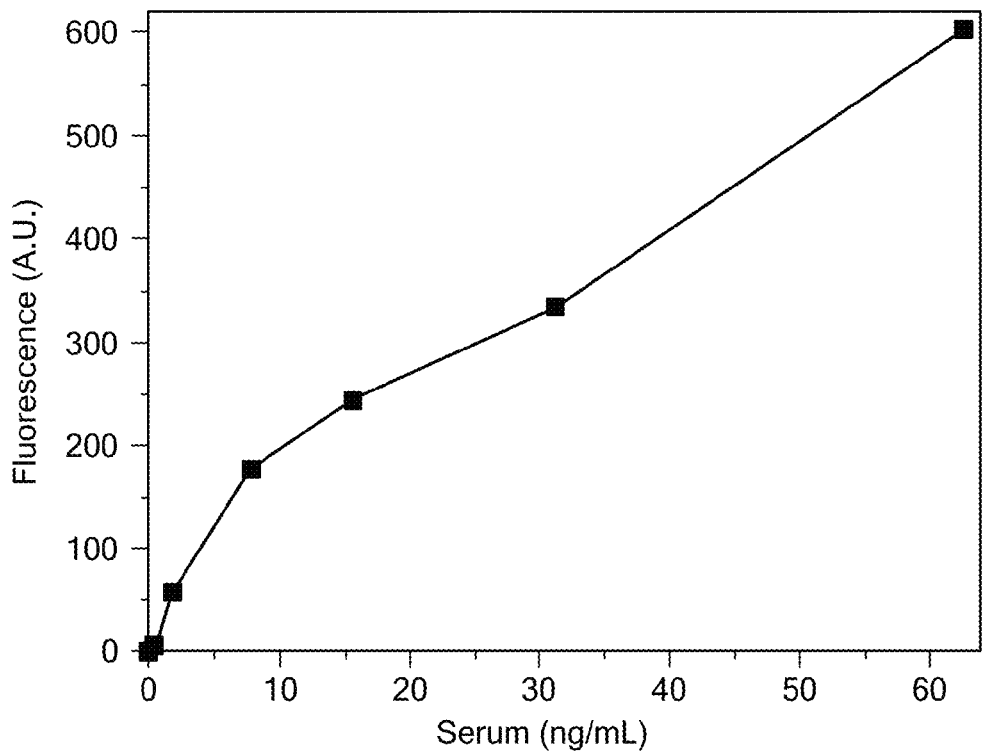
FIG. 14A shows a rat IgG ELISA run in a 96-well Greiner black multiwell plate at 100 ml. The fluorescence intensity was measured 15 min after the addition of the enzymatic substrate fluorescein diphosphate (FDP).

FIG. 14A shows an enzyme-linked immunosorbent assay (ELISA) using rat IgG. The ELISA is run in a 96-well Greiner black multiwell plate at 100 ml. The fluorescence intensity was measured 15 min after the addition of the enzymatic substrate fluorescein diphosphate (FDP).

Figure 14B:
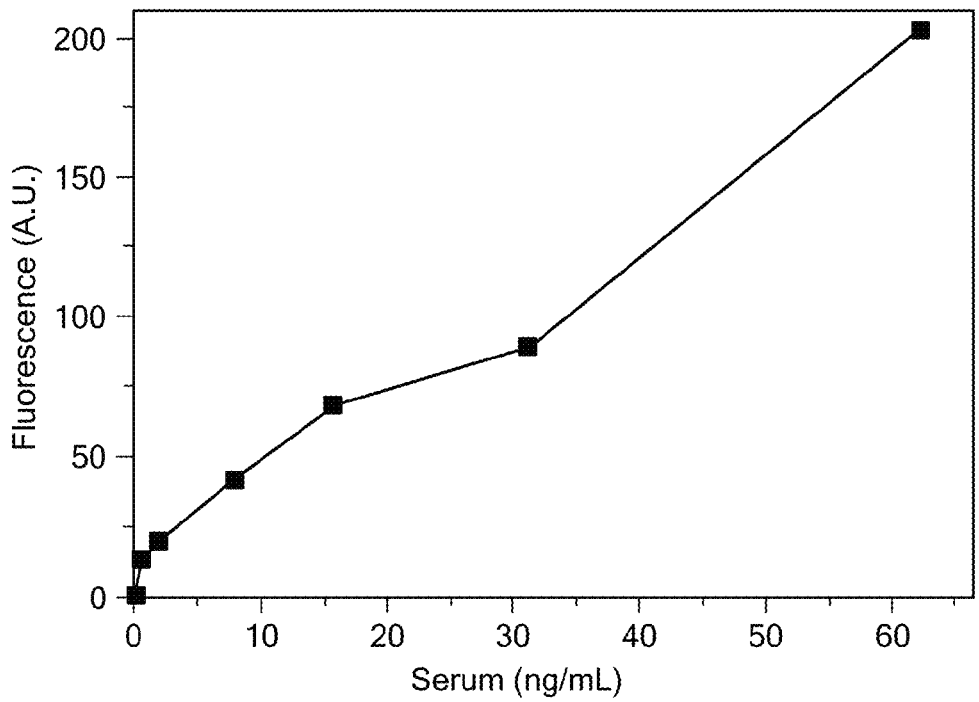
FIG. 14B shows a rat IgG ELISA run on a patterned immobilisation member at a volume of 3 µl. The fluorescence intensity was measured 11 min after the addition of FDP substrate.

FIG. 14B shows a rat IgG ELISA run on a patterned immobilisation member at a volume of 2 ml. The fluorescence intensity was measured 11 min after the addition of FDP substrate.

Figure 15:
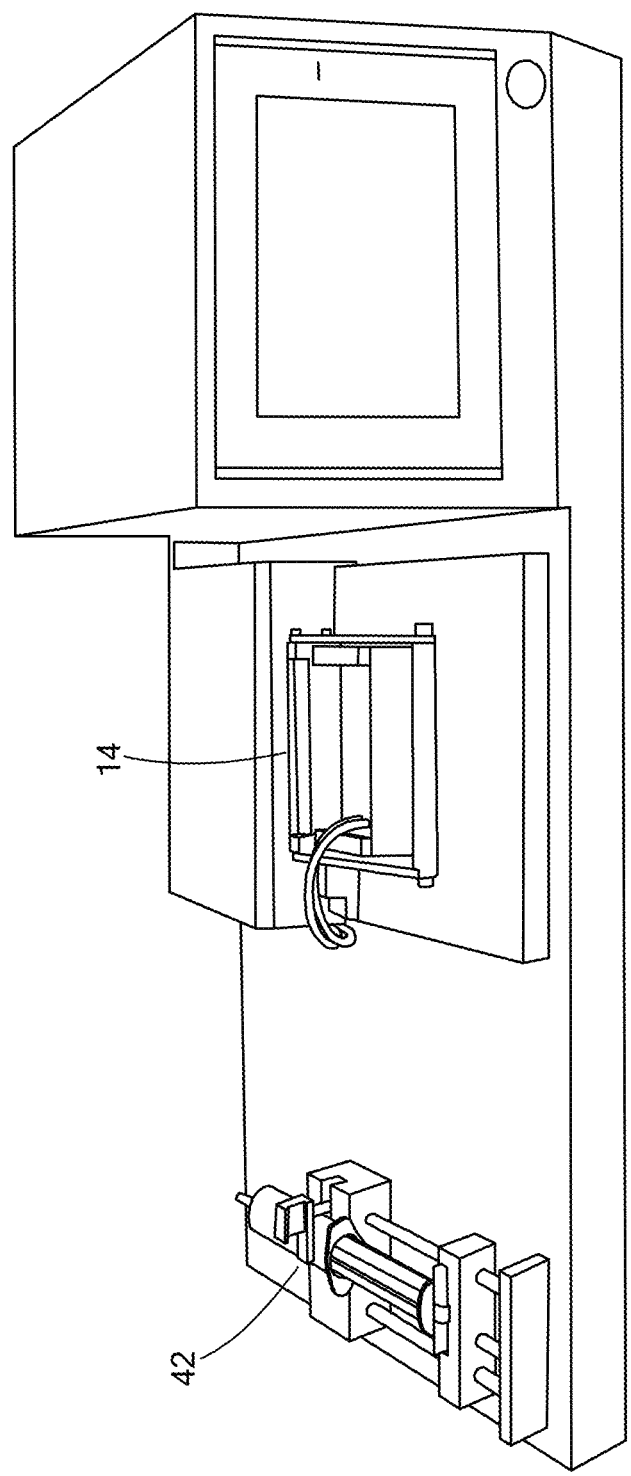
FIG. 15 depicts a batch-shaking Automated Rinsing Station that can be used in the method of the invention.

FIG. 15 depicts a batch-shaking Automated Rinsing Station. This rinsing station is capable of performing a series of steps required for a batch-shaking rinsing method: tilting, addition and draining of a medium such as a liquid, and shaking. The rinsing station consists of three main components: a controller, a sample stage with a pivoting reservoir holder, and a pressurizing device in the form of a syringe pump. The computer controller directs each motion and the sequence of motions. The computer can be replaced with a microprocessor with a simple combination of buttons, switches, and/or displays. In the depicted example the pivoting reservoir holder (41) has a motor with an axis to tilt the assembled processing compartment that includes a reservoir (in the form of a slide holder) and chamber cover (slide cover) to a desired angle. Below the sample stage, there is provided an agitation device in the form of another motor to shake the sample stage, with any reservoir/processing compartment received by the reservoir holder, at a desirable speed and rate, for example by linear motion. The reservoir holder can be replaced readily to receive another processing compartment with for example a different size of an immobilisation member (or sample slide). For example, for immobilisation members that are slides of 75 mm×25 mm and 75 mm×43 mm, a different sample stage may be used interchangeably. The syringe pump (42) is used to add medium such as liquid to the assembled chamber as necessary.

An exemplary sequence of action is as follows:

(1) A processing compartment (slide chamber) is placed in the reservoir holder and assembled with a chamber cover through water-tight sealing manually.

(2) The assembly is tilted at 120° for 10-20 seconds with a draining valve open. This step drains an immiscible fluid in the assembly.

(3) The assembly is tilted at 90° followed by addition of a fresh rinsing solution.

(4) The assembly is positioned horizontally on the sample stage and shaken for 30-60 seconds.

(5) The assembly is tilted at 120° for 20-40 seconds with draining valve open. This step drains a solution in the assembly.

(6) The assembly is positioned horizontally on the reservoir holder. The exact sequence of actions may vary depending on the nature and requirement of an assay run on a slide.

Figure 16A:
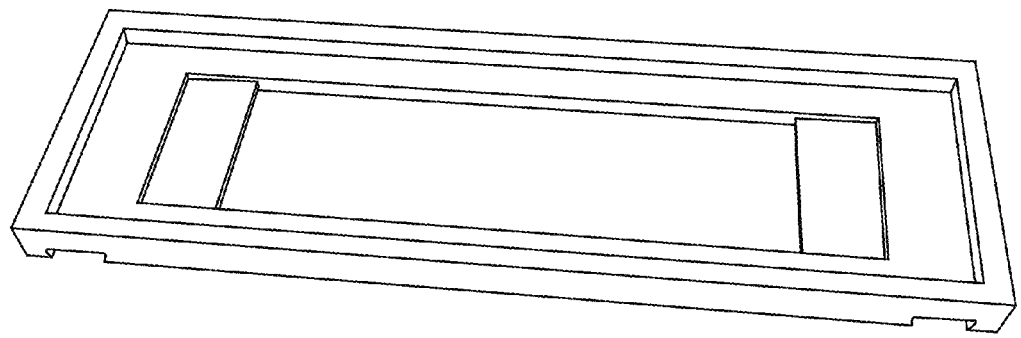
FIG. 16 shows further embodiments of an apparatus (A, B, C) of the invention where removable a chip is used (depicted in FIG. 16C) that includes a plurality of predefined immobilisation areas within a patterned surface.
Figure 16B:
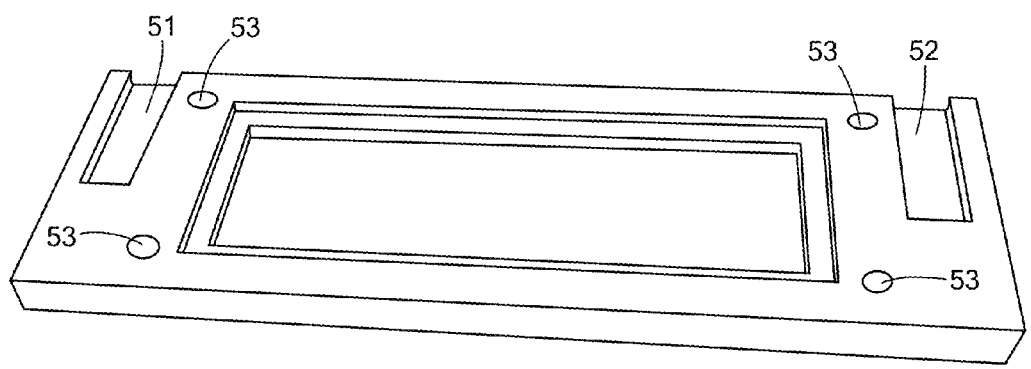
Figure 16C:
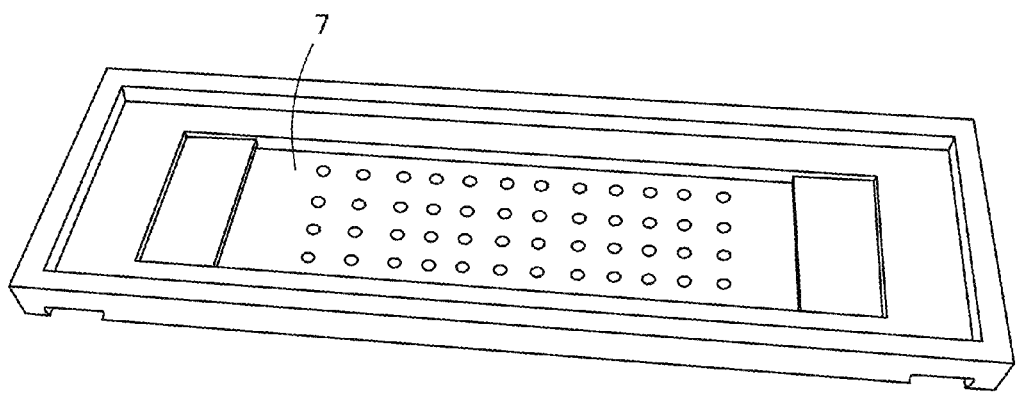

FIG. 16 shows a further apparatus of the invention where a removable chip is used (depicted in FIG. 16C) that includes a plurality of predefined immobilisation areas within a patterned surface. FIG. 16A shows the apparatus from the front (i.e. seen from above), whereas FIG. 16B shows the apparatus from the back (i.e. upside down). FIG. 16C depicts the apparatus from the front with an immobilisation member in the form of a removable chip (7) inserted.

The patterned slide may be glued to the bottom of the chamber of the apparatus. The depicted chamber has two layers of a through-hole pocket, an inner layer and an outer layer, at the center of the chamber. Upon assembling the apparatus a patterned slide is attached to the bottom of the pocket to create a reservoir. The inner reservoir is used to hold an immiscible liquid such as PFCL for incubation. The outer reservoir is used to prevent any leakage of the immiscible liquid. The depicted apparatus defines a slide chamber designed for a slide of ~75 mm×25 mm. As can be seen in FIG. 16B, the slide chamber has rectangular indentions (51, 52) designed to fix the slide chamber in an accommodating instrument. In addition, the chamber has four circular indentions (53) designed to facilitate the stacking of chambers on top of each other, in the presence of a chamber lid.

Figure 17:
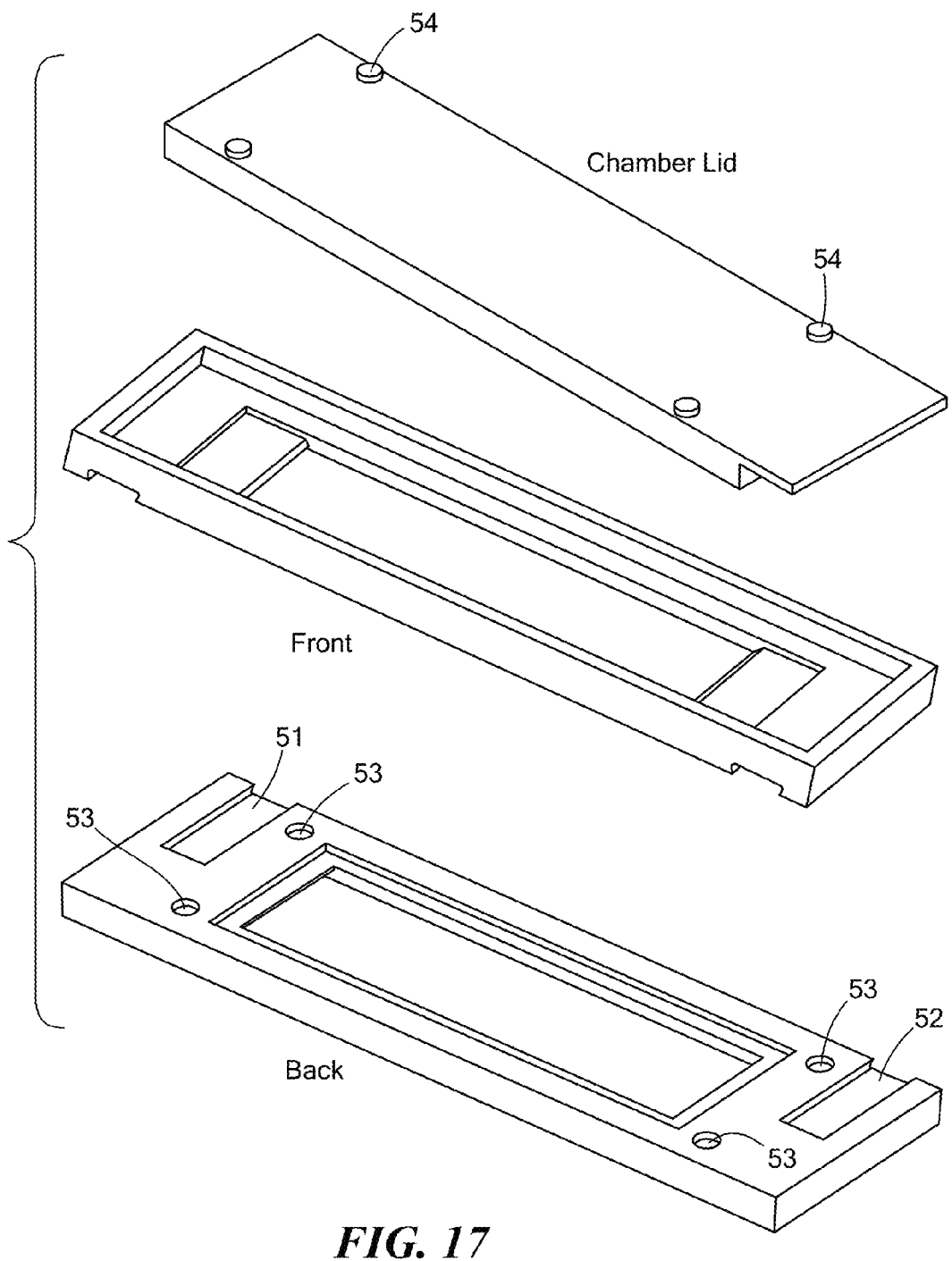
FIG. 17 shows an apparatus resembling the apparatus depicted in FIG. 16, wherein a chamber lid is used for assembly instead of the slide shown in FIG. 16.

FIG. 17 shows an apparatus resembling the apparatus depicted in FIG. 16, wherein a chamber lid is used for assembly instead of the slide shown in FIG. 16. The chamber lid has protrusions (54) that match the circular indentions (53) of the chamber of the apparatus.

Figure 18A:
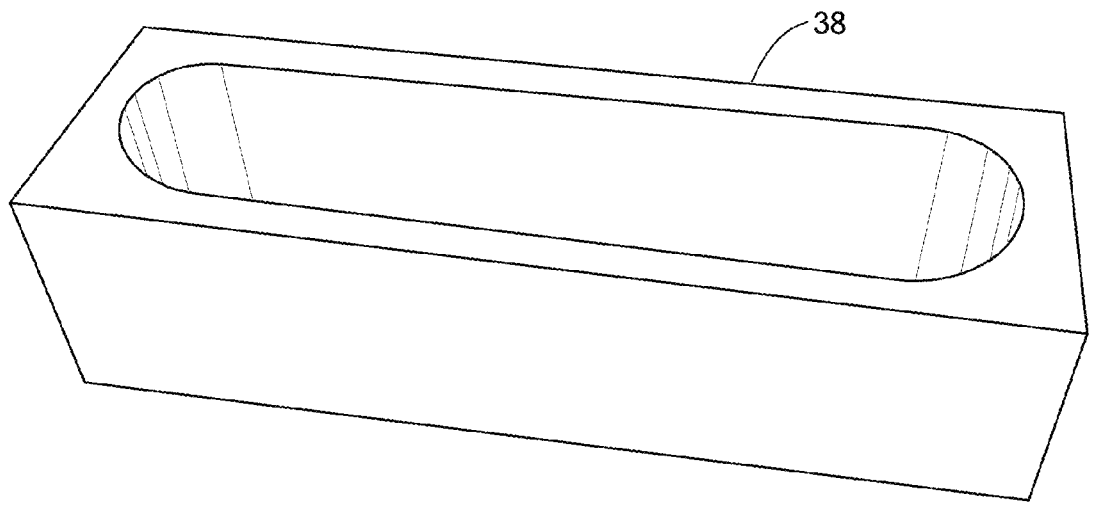
FIG. 18 depicts a chamber cover that can be assembled to an apparatus of the invention. As seen in top view (FIG. 18A) the shown chamber cover defines a reservoir, which can be assembled in a water-tight manner by means of an O-ring (33), as seen in a perspective from the bottom (FIG. 18B).
Figure 18B:
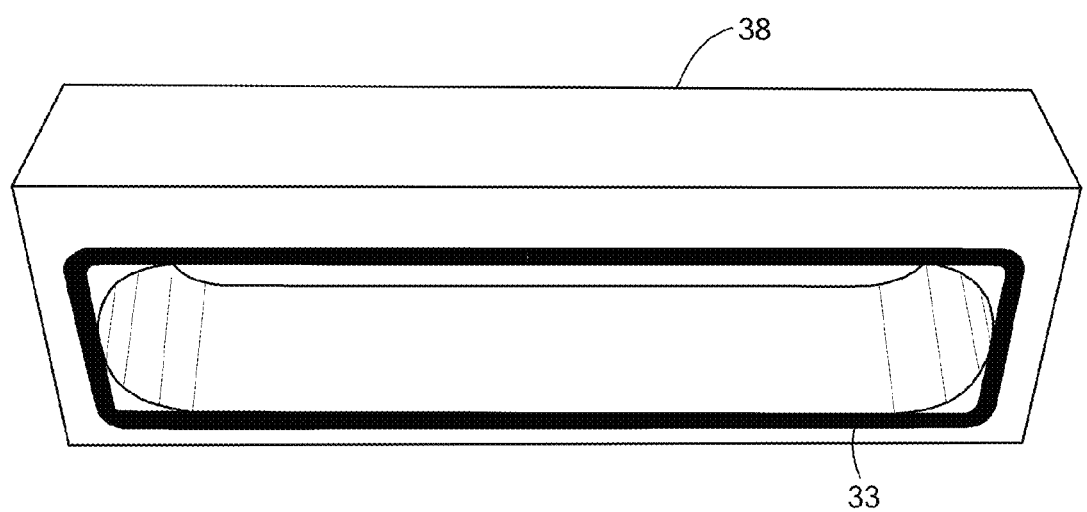
Figure 19A:
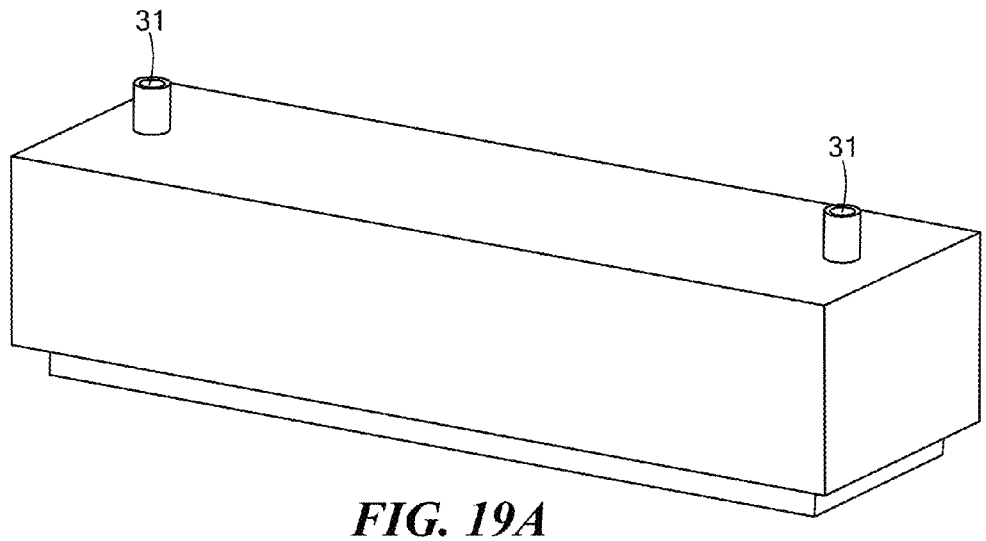
FIG. 19 depicts an inlet member, which has two openings (31) on a top thereof (FIG. 19A) and a groove (32) at the bottom for receiving an O-ring (FIG. 19B).
Figure 19B:
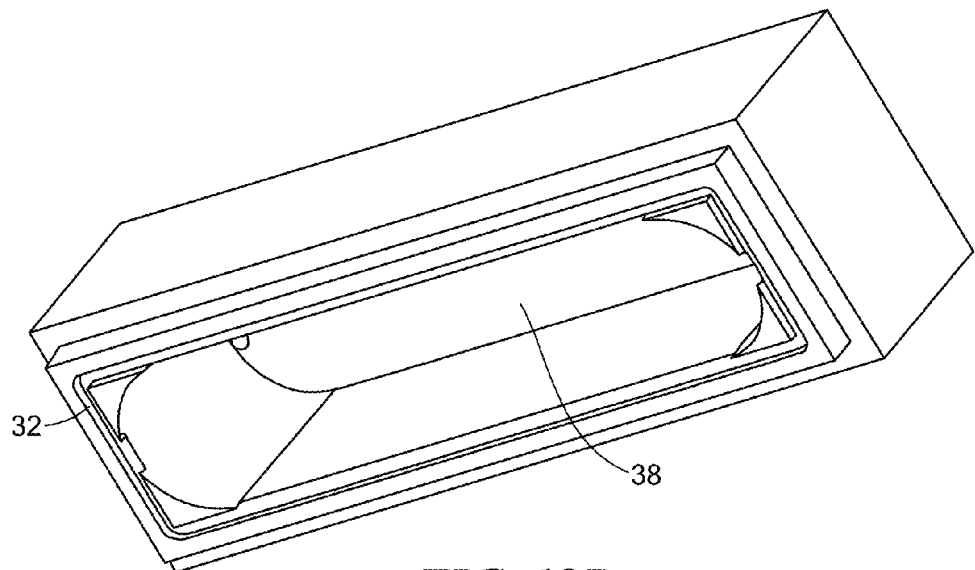

FIG. 18 depicts an example of a chamber cover designed for a slide of ~75 mm×25 mm. FIG. 18A shows a first chamber cover from the top, while FIG. 18B depicts the same chamber cover, seen from the bottom. The chamber cover has an opening (38). Upon placing the chamber cover onto the reservoir this opening may form a continuous space with the reservoir. For water-tight sealing, the cover has a glued O-ring (33), which contacts the slide holder upon assembly. FIG. 19 depicts an example of an inlet member, likewise designed for a slide of 75 mm×25 mm. FIG. 19A shows the inlet member from an elevated perspective, in which the top and two sides are visible. Two openings (31) for the transfer of a rinsing solution are arranged at the top of the inlet member, one at each side along the long axis. FIG. 19B shows the same inlet member from a perspective in which the bottom is visible. An opening (38) is visible, which can form a continuous space with the reservoir. Into a notch (32) an O-ring can be placed.

Figure 20A:
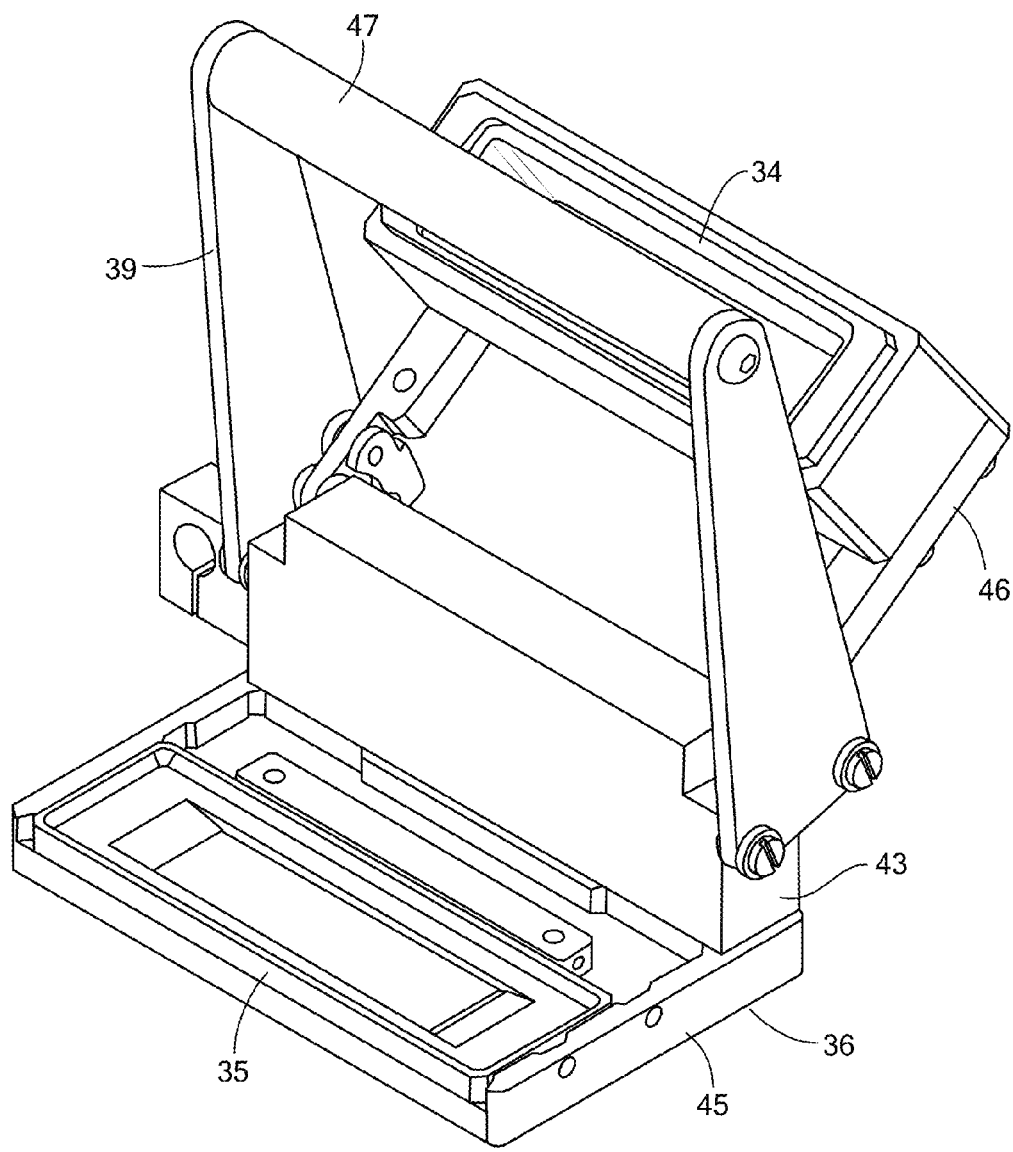
FIG. 20 illustrates a technique and a device (36) of/for attaching an inlet member (34) to the reservoir of an apparatus of the invention (35) before (A) and after assembly (B).
Figure 20B:
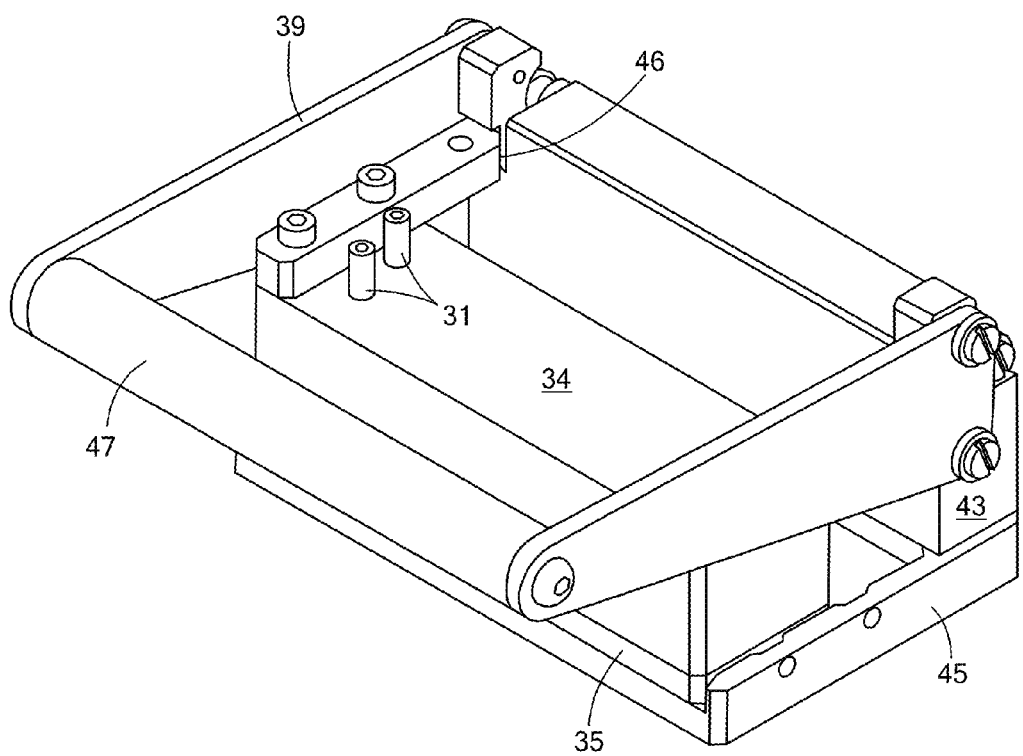

The inlet member as well as a chamber cover may have additional features in order to be attached to a device for attaching an inlet member and/or a cover, that enables free up-and-down movements for reversible water-tight sealing and unsealing. FIG. 20 depicts a device (36) for attaching an inlet member (34) (which includes two inlets (31) in the depicted example) and/or a cover to the reservoir (35) of an apparatus of the invention. Both the inlet member and the reservoir may have elements and/or devices that allow attaching, fixing and/or removing from the respective device (36). The device (36) has a first holder (45), which is designed to receive the reservoir (43), and a second holder (46), which is designed to receive the inlet member (34) or a cover. The device further has a pivotal point (43) for positioning the inlet member (34) onto the reservoir (35). Using a lever (39) with a handle (47) the second holder (46) can be pivoted onto the first holder (45), thereby pivotally mounting the inlet member (34) onto the reservoir (35).

Figure 21:
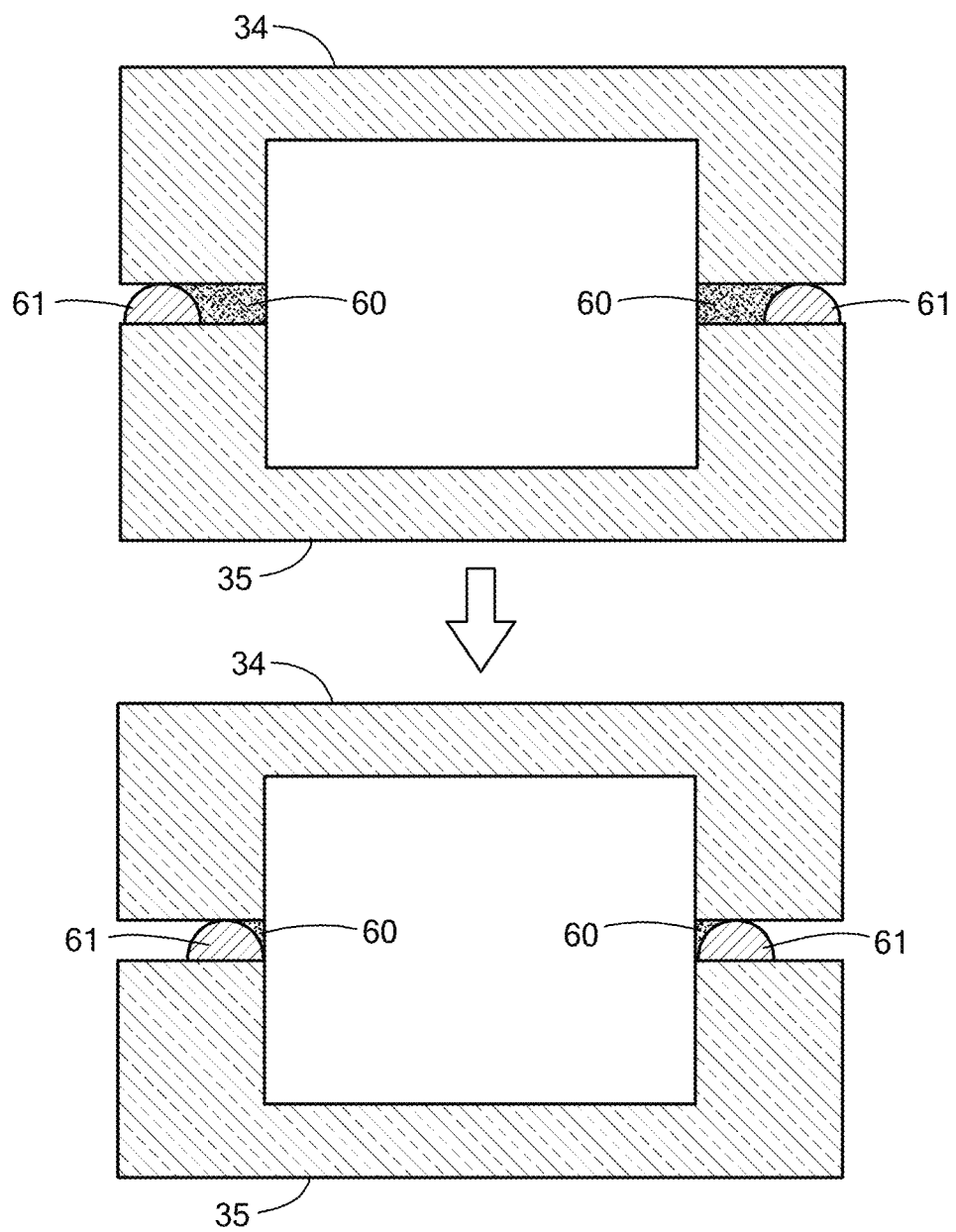
FIG. 21 depicts a means of assembling the reservoir of an apparatus of the invention (35) and inlet member (34), and sealing by elastomeric contact. The figure also illustrates how the arrangement of an O-ring (61) during assembly of affects the volume of dead space (60).

The mechanism employed for the reversible locking/unlocking of a slide chamber is a feature of the design of slide chamber and inlet member, and in other embodiments slide chamber and cover, which may in some embodiments be of high practical relevance. The minimum requirement typically includes that the contact ought to be water-tight when the slide chamber is locked with the inlet member in order to avoid any leakage of rinsing solution. Furthermore it will usually be desired to provide be simple and straightforward means to lock and unlock in order to facilitate easy and convenient operation. Typically the inlet member (or cover, respectively) will be designed in a way that it does not block or interfere with the addition of reagents and samples onto the slide by manual or automatic dispensing when the system is unlocked. It may also be desired to design the apparatus in a way that the slide chamber can leave minimal residual liquid on the surface upon draining of an immiscible liquid and/or rinsing solution. Furthermore it may be desired to provide a contact area between the chamber and the inlet member that has a minimal dead space upon assembly. This may be desirable to minimize the amount of static liquid trapped at the dead space, which may potentially increase the chance of carry-over contamination from a previous rinsing step. FIG. 21 depicts an example in which the chamber (35) and the inlet member (34) are in contact with each other via an O-ring (61). A dead space (60) with static liquid is limited by the location and size of the O-ring (61).

Several locking/unlocking mechanisms for the slide chamber and inlet member are illustrated in the following. The same mechanisms generally apply to locking/unlocking of a slide chamber and a cover.

Sealing by Mechanical Force Via Elastomeric Contact

Figure 22A:
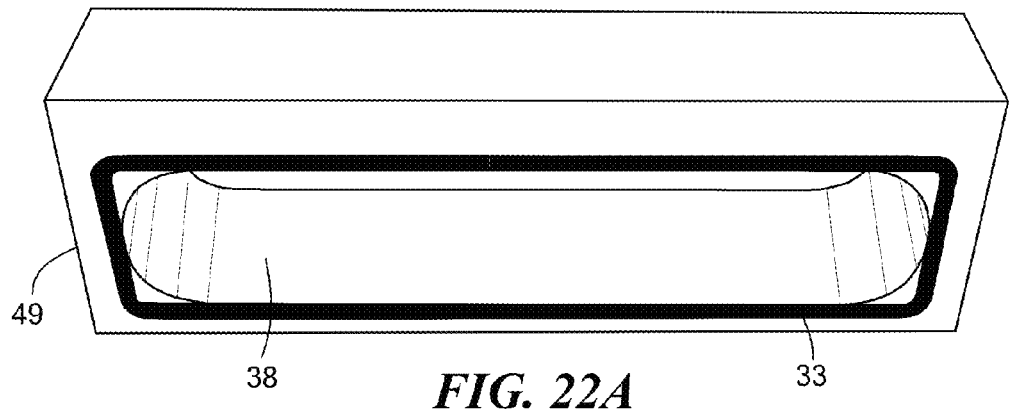
FIG. 22 depicts a process of assembling a chamber cover (A) and a processing compartment of an apparatus of the invention (B) to form an assembled apparatus with a chamber cover (C) that includes a closed space, which may be a sealed compartment.
Figure 22B:
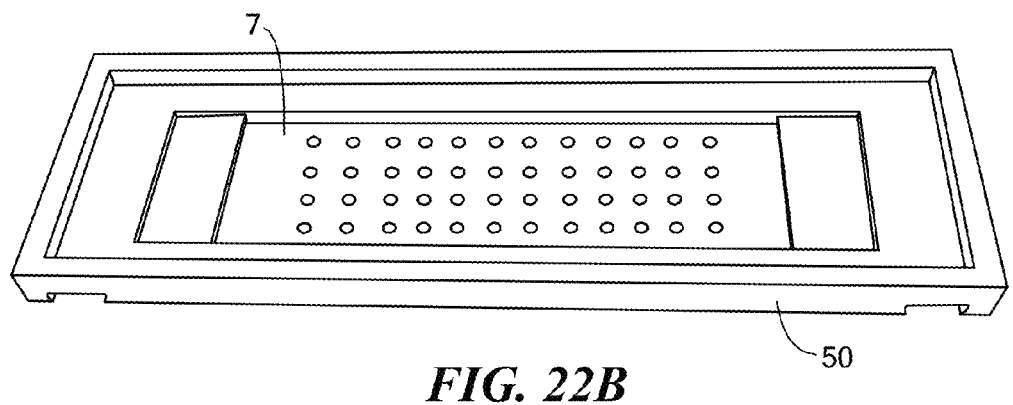
Figure 22C:
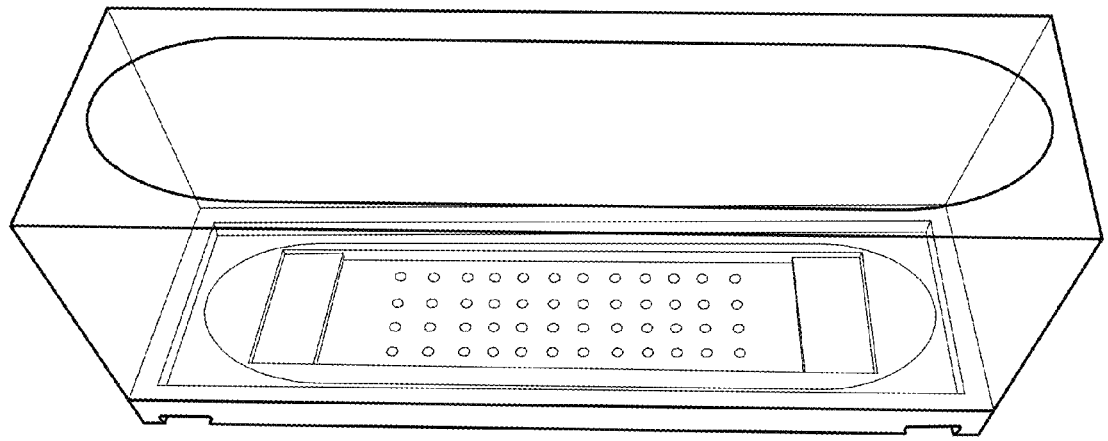

In this embodiment the force required for water-tight sealing is applied mechanically, while the contact between the slide chamber and inlet member is made via an elastomeric component, such as an O-ring. This method includes a mechanical toggle design as employed in FIG. 20. The O-ring can exist either on the slide chamber or on the inlet member. FIG. 22C shows the assembled slide chamber and a cover, which are sealed by an O-ring in the same way. FIG. 22A depicts the chamber cover (49) with an O-ring (33) and an opening (38) of a cavity before assembly. FIG. 22B depicts a respective processing compartment (50) that includes an immobilisation member (7), onto which the chamber cover is assembled.

Sealing by Electromagnetic Force Via Elastomeric Contact

In this embodiment the force required for water-tight sealing is applied by electromagnetic attraction. For example, the slide chamber is either embedded or attached with a metallic strip, while the inlet member comes with an electric magnet as shown in FIG. 23. Upon activation and deactivation of the electric magnet in the cover, the slide chamber and inlet member are water-tight sealed and released, respectively. The positions of the electric magnet and metallic strip can be switched, i.e. the magnet can be located in the slide chamber and the strip can be embedded in the cover. Likewise, the O-ring can be placed on the slide chamber or inlet member.

Sealing by Pressure Difference

In this embodiment the force required for water-tight sealing is applied by pressure difference. For example, the slide chamber has an open channel embedded in the area contacting an inlet member (see FIG. 24). A part of the open channel is in fluid contact with a vacuum channel. Upon establishing contact between the slide chamber and inlet member, a vacuum is applied through the vacuum channel. This results in a negative pressure along the open channel, generating a strong sealing between the chamber and inlet member. The positions of the open channel and O-ring can be switched, i.e. the channel can be embedded in the inlet member and the O-ring can be placed in the slide chamber.

In some embodiments the inlet member is a pipetting guide, a component that assists manual pipetting onto an array of wells on the slide surface. It is placed on top of a slide holder for dispensing by a multi-channel pipette or a single-channel pipette. The guide has a plurality of tilted through-holes, where a plurality of 8 or 12 pipette tips can pass through and rest during dispensing for a convenient and reliable pipetting operation. In the depicted embodiments the pipetting guide is not equipped with an O-ring. Where desired a sealing mechanism such as a respective O-ring may nevertheless be used.

Pipetting Guide

Figure 25A:
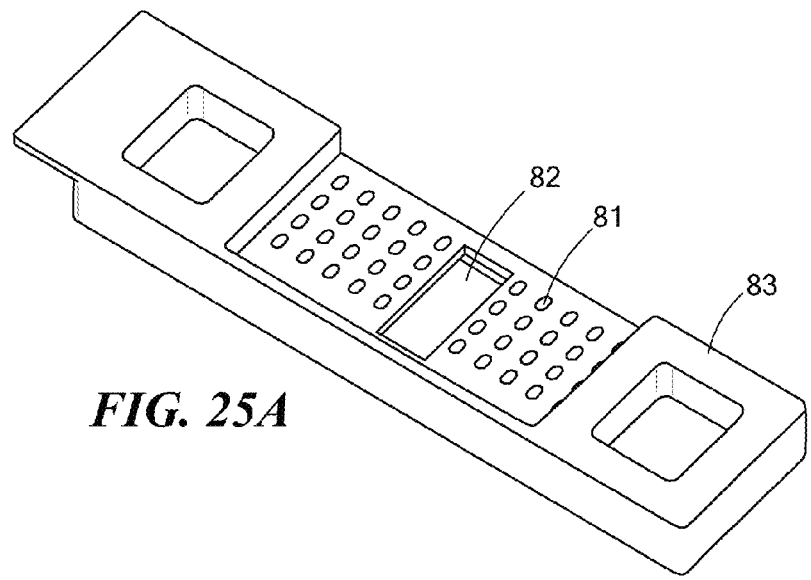
FIG. 25 depicts two embodiments of an inlet member in the form of a pipetting guide (A, B) and an example of a pipetting guide positioned on top of a processing compartment (C).
Figure 25B:
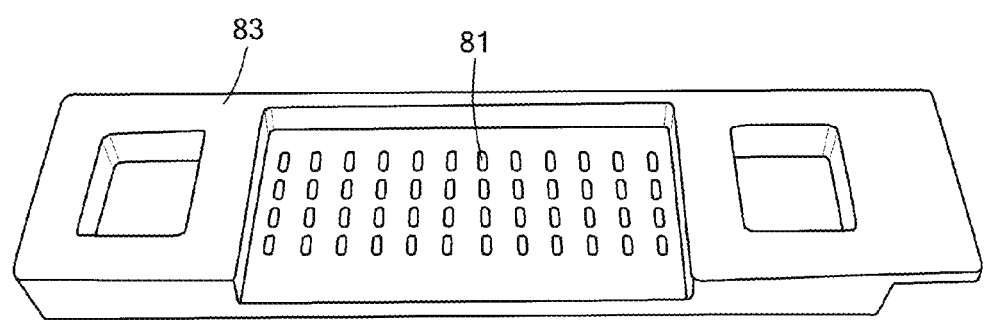
Figure 25C:
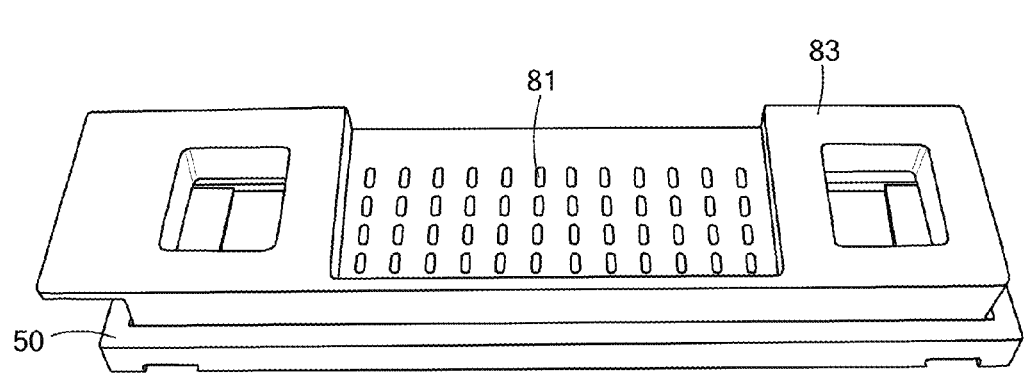

FIG. 25 shows embodiments of an inlet member in the form of a pipetting guide. It has a frame (83) that allows stacking on top of a slide chamber. The pipetting guide depicted in FIG. 25B includes a plurality of positioning means in form of through-holes (81) for the guidance and passing of pipette tips. The pipetting guide depicted in FIG. 25A further has a large through-hole (82) in the middle for better visibility. The guide may be fabricated with a transparent material in order to improve visibility, so that the user can see the location of the pipette tips. FIG. 25C depicts the pipetting guide shown in FIG. 25B positioned on top of a processing compartment (50) in the form of a slide chamber.

Figure 26A:
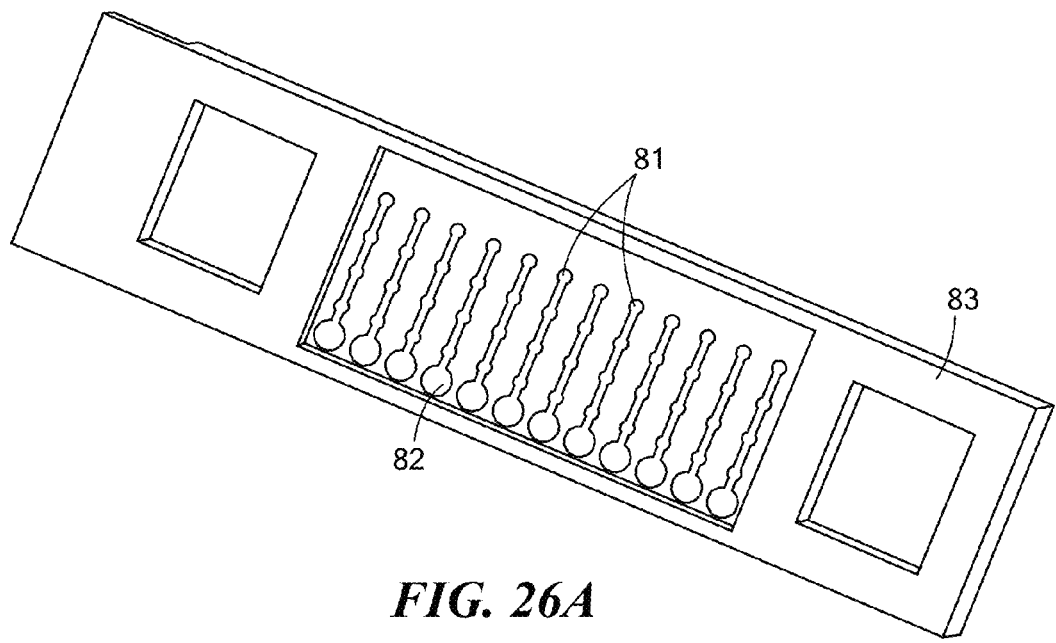
FIG. 26 shows a further embodiment of a pipetting guide (A), and the same positioned on top of a processing compartment (B).
Figure 26B:
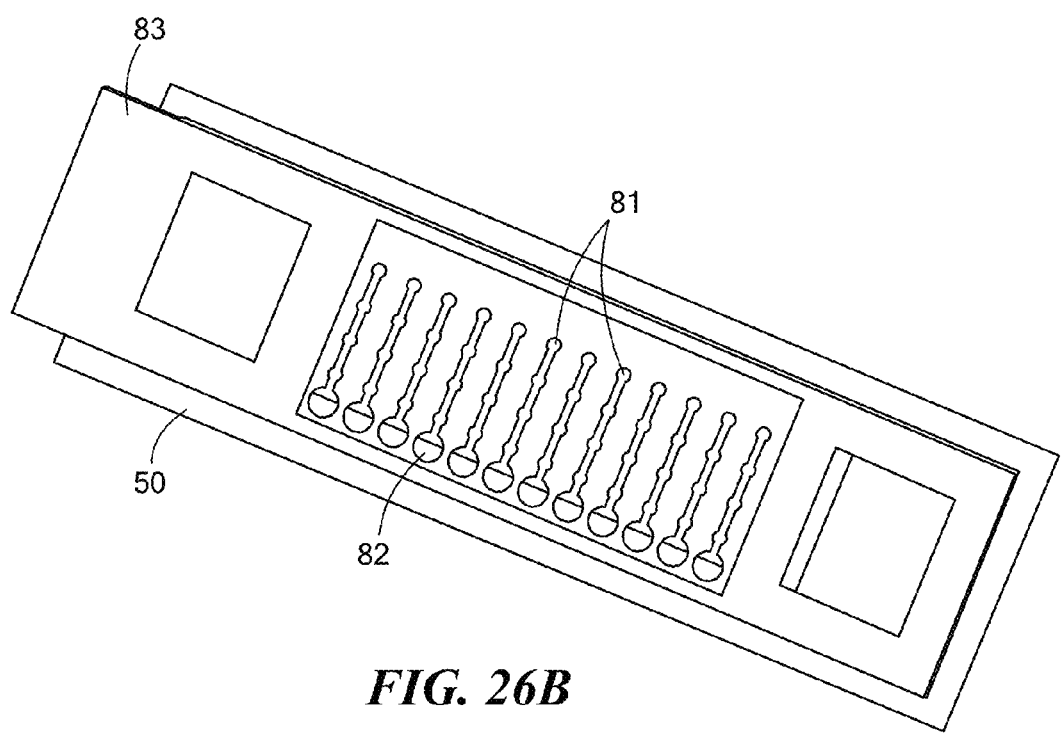

FIG. 26 shows a further embodiment of an inlet member in the form of a pipetting guide. The inlet member has a frame as depicted in FIG. 25, a plurality of large through-holes (82) for better visibility and an array of positioning means in form of through-holes (81) to guide and position pipette tip(s) slightly offset to the center(s) of the well(s) on the slide surface (FIG. 27), when the inlet member is placed on a processing compartment (50). This offset prevents the coating of the wells from being scratched by the pipetting tip(s). With the offset, however, the dispensed reagents can still reach the hydrophilic well surface and move onto the center of it by the surface tension of the liquid. A narrow slot is cut through the holes for each row. These slots are used to guide the pipette tip(s) from one dispensing location to the next. In addition, the diameter of the through-holes in the first column (Column A) of the array is larger than those of the rest (Columns B, C, D and E). These large holes facilitate the insertion of pipette tips into the guide. An array of 8 or 12 pipette tips can pass through the narrow slots, and rest in the positioning holes one by one during dispensing for a convenient and reliable pipetting operation. The guide has a frame that allows stacking on top of the slide chamber. It may have a large through-window in the middle for better visibility. Furthermore, the guide is preferably fabricated with a transparent material in order to improve visibility, so the user can see the location of the pipette tips.

Figure 29A:
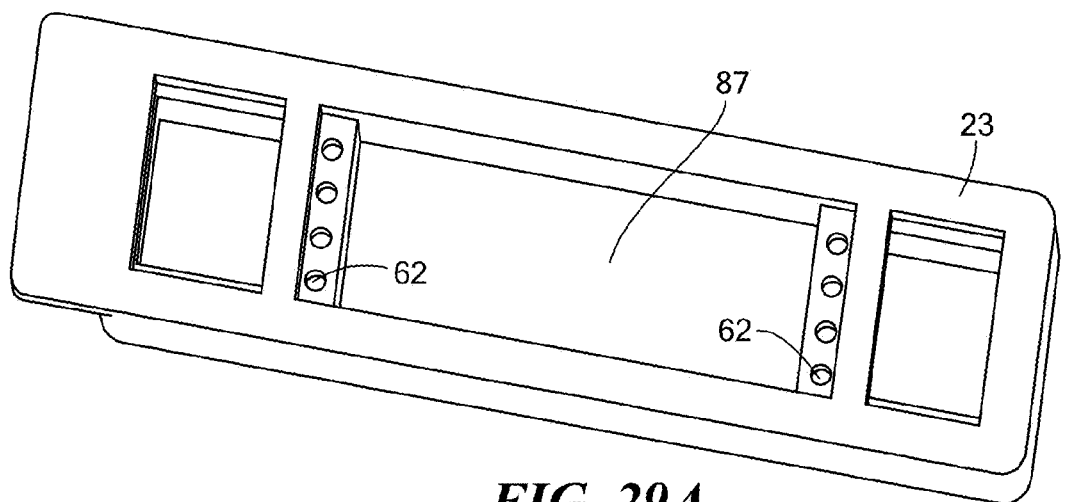
FIG. 29A depicts the frame (23) with pairs of bores (62) shown in FIG. 28.
Figure 29B:
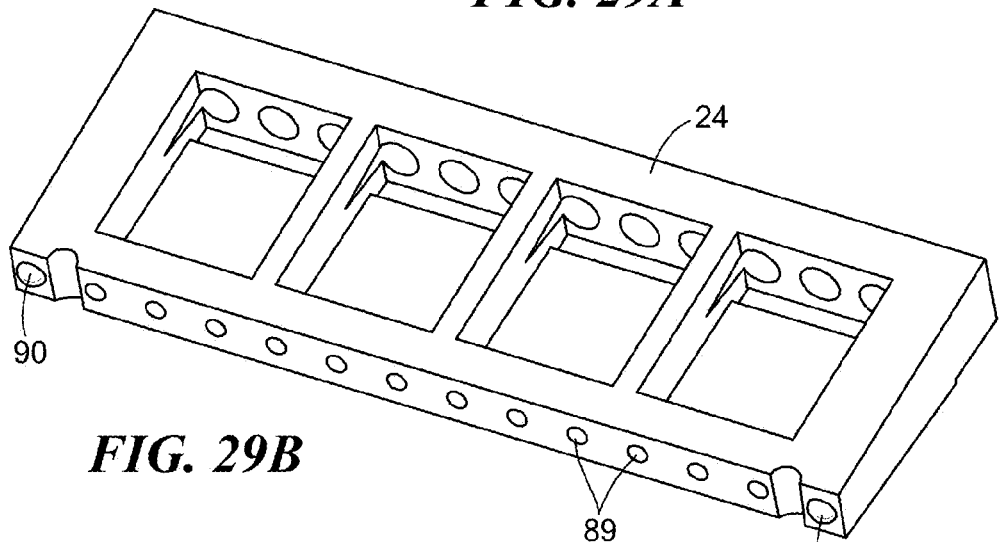
FIG. 29B depicts the mount (24) of FIG. 28 and FIG. 29C the mount (24) with pipette tips (86) inserted.
Figure 29C:
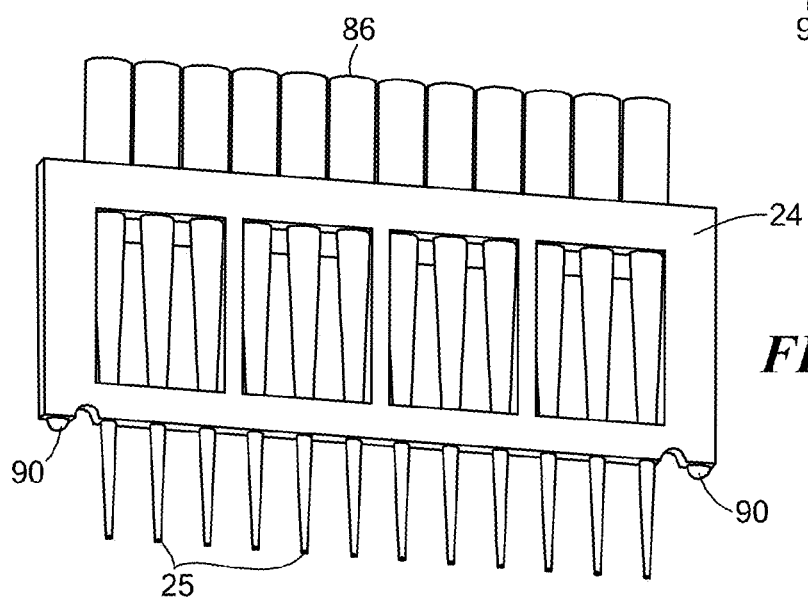

FIG. 28 shows another example of an inlet member in the form of a pipetting guide assembly. This inlet member includes a pair of interacting positioning means (23, 24). One positioning means is a frame (23) with a large opening (87). The frame is also depicted in FIG. 29A. It has further a plurality of bores (62), defining four pairs, which are designed to receive a mount (24). Each pair of the bores can be used to align the mount with one row of predefined immobilisation areas on an immobilisation member. The mount is designed to receive and position pipette tips (86) (FIG. 29B, FIG. 29C), thereby allowing guiding positioning a dispensing device. The large opening (87), designed as a through-window in the middle of the frame (23), allows the ends (25) of the pipette tips (86) (see FIG. 29C) to enter the processing compartment and, where desired, to approach the surface of an immobilisation member therein. The mount (24) is capable of holding the pipette tips (86) in a straight line with exactly the same and uniform pitches as that of the immobilisation areas on an immobilisation member, for example corresponding to wells of a conventional 384-well plate, 96-well plate or 48-well plate (cf. FIG. 2D). Except for a row of through-holes (89) to insert the pipette tips, the mount also has a dent (90) in the form of a small dome next to both ends of the through-hole array. The two dents (90) will respectively fit into each pair of bores (62) on the frame (23) to ensure that the pipette tips are aligned with the immobilisation areas on an immobilisation member before pipetting. When the inlet member (designed as a pipetting guide assembly) is fit into the chip holder of the reservoir, the air gap between the pipette tips and the wells is controlled at 0.1 mm to 1.0 mm—depending on the sizes of the droplets to be dispensed. By this way, the dispensed droplet array from the pipette tips can be easily and readily transferred and attached to the hydrophilic immobilisation areas.

Continuous Flow Method

Figure 30:
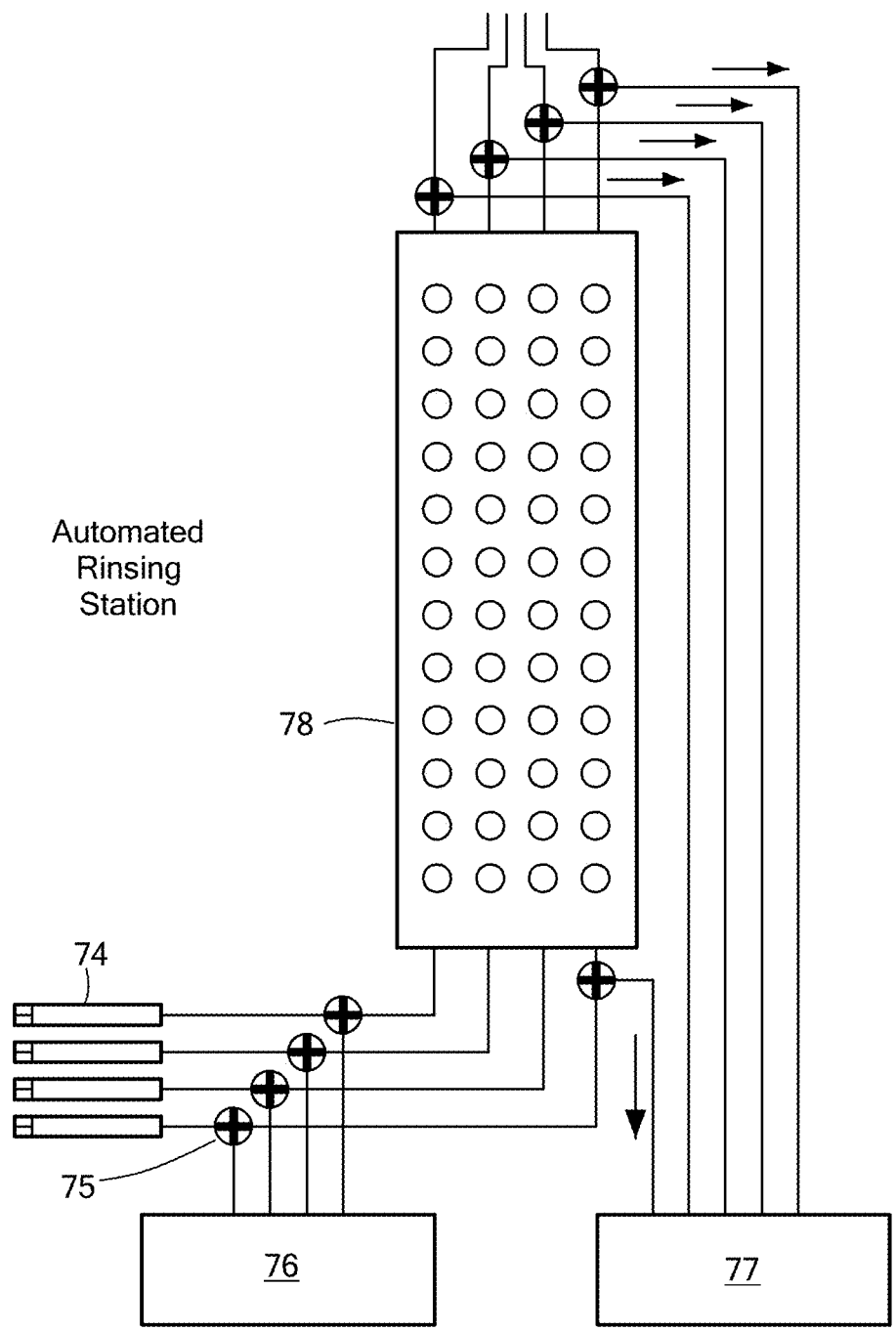
FIG. 30 shows an application of the apparatus and method of the present invention in a continuous flow process. Fresh rinsing solution (76) contacts the patterned surface of a slide (78) in flow. 3-way valves (75) allow inter alia the application of matter (samples, reagents, etc.) via syringes (74) and the direction of rinsing solution to the waste (77).

FIG. 30 illustrates a continuous flow method, which uses a continuous flow of a fresh rinsing solution that passes over the surface of the slide. It employs a slide chamber and pipetting guide similar to those for the batch shaking method with minimal modification. The design of the inlet member, however, is significantly different from that for the batch shaking method. In the batch shaking method, the inlet member typically has a rectangular design with a relatively big inner volume. In the continuous flow method, the inlet member is designed to be thin, whereby the distance from the slide surface to the inlet member is only 0.2-5 mm. Furthermore, it may be desired to obtain a flow within the assembled reservoir that is uniform throughout the exposed slide surface in order to maintain a similar rinsing effect for all the predefined surface areas of the immobilisation member ("wells"). This can be achieved by means of the depicted embodiment.

The examples of chamber cover are designed for a glass slide patterned with a 12×4 array of surface areas. The shape and geometry of a cover may vary depending on the arrangement of surface areas.

Figure 31A:
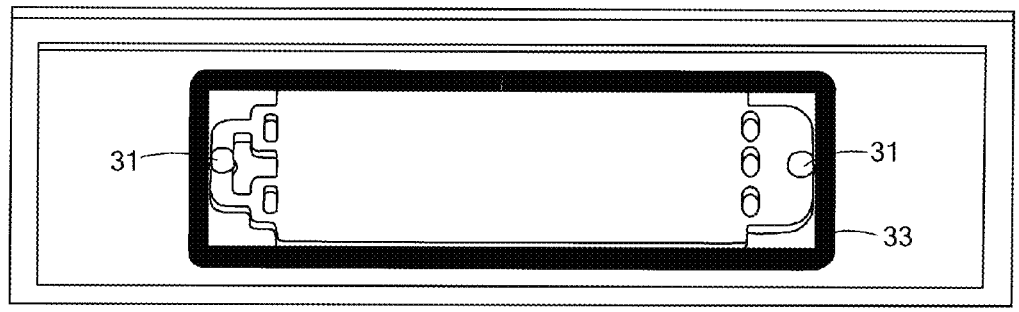
FIG. 31 depicts in bottom view (A), side view (B) and as a see-through image, when assembled with a slide chamber (C), an embodiment of an inlet member (34). It includes two inlets (31), one of which may function as an outlet, and embedded features and flow splitters and an O-ring (33) for sealing.
Figure 31B:
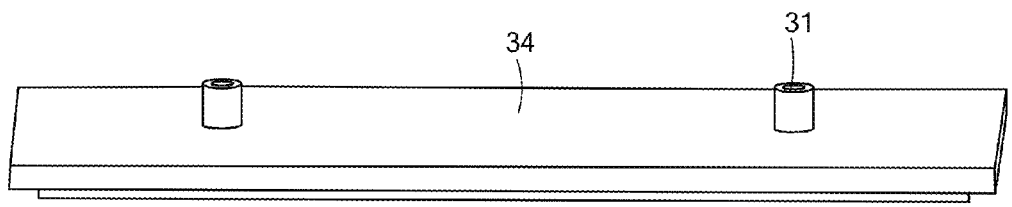
Figure 31C:
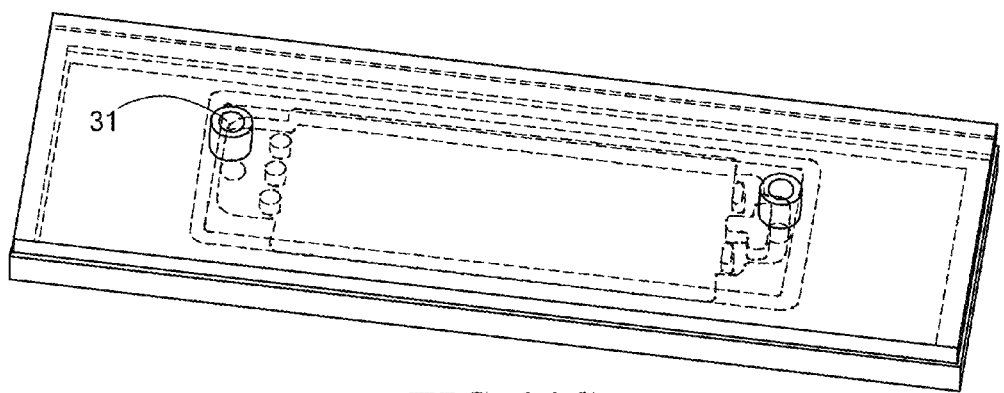

In one embodiment an inlet member has one inlet and one outlet, and includes embedded features and flow splitters (FIG. 31). The flow splitters at each end split the flow of a rinsing solution from the inlet into four uniform streams. Each stream is designed to flow along each row of 12 glass wells on the slide. Two examples of flow splitters are shown in FIG. 31. In the design, an O-ring contacts the edge of a pocket of the slide chamber for water-tight sealing as described in the batch shaking method. The flow splitters contact the surface of the patterned slide with minimal space between the slide surface and the surface of flow splitters. This is to minimize dead space, which can trap the rinsing solution during the flow of a fresh rinsing solution. For better contact between a slide and flow splitters, the splitters can be made of elastomeric materials.

Figure 32A:
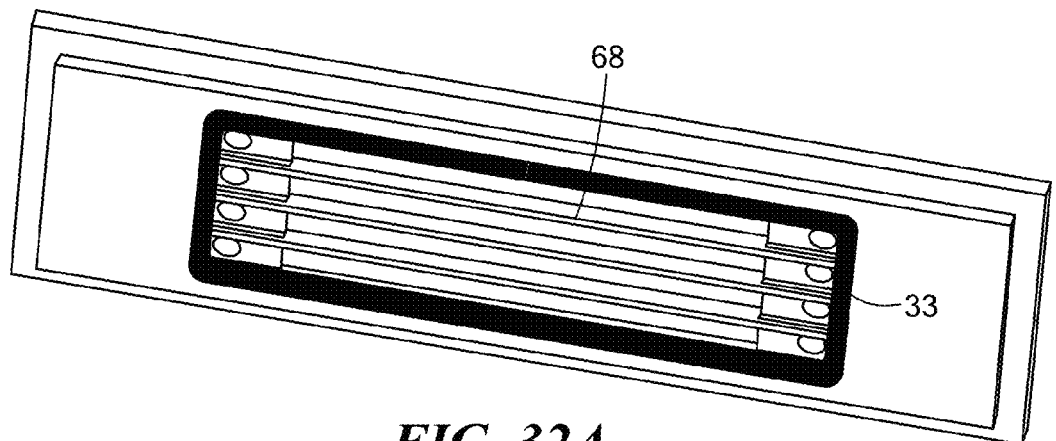
FIG. 32A depicts a further embodiment of an inlet member that includes eight inlets (four of which may for instance function as outlets), physical dividers (68) and an O-ring (33).
Figure 32B:
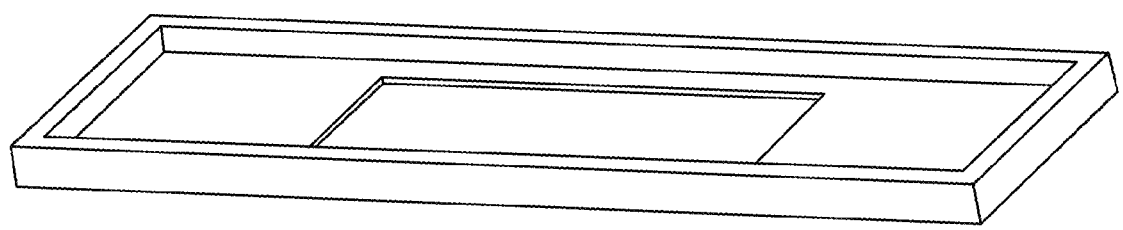
FIG. 32B depicts a corresponding slide chamber, to which the inlet member may be assembled.
Figure 32C:
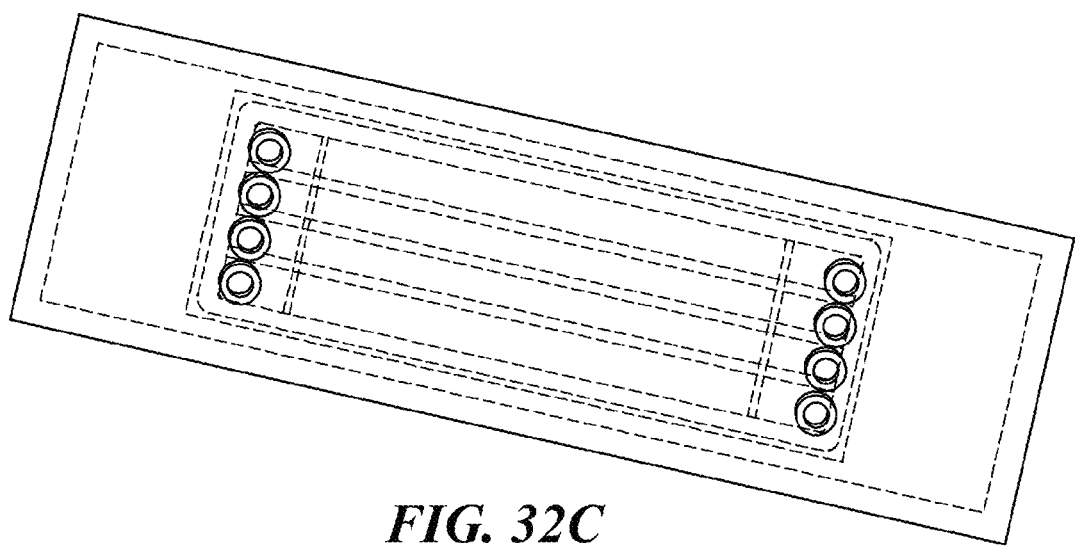
FIG. 32C depicts a see-through image of the inlet member and chamber when assembled.

In another embodiment, a cover has four inlets and four outlets, and contains physical dividers as shown in FIG. 32. Upon the assembly of the cover with the slide chamber, four isolated channels are generated along each row of 12 glass wells on the slide. The presence of individual inlet, outlet and physically separated channel would ensure uniform flows through each row of the array on the slide. The O-ring in the cover contacts the edge of the pocket of the slide chamber, and the three barriers contact the slide surface and chamber to minimize any dead space. For better sealing between the barriers and the slide and chamber, the barriers can be made of elastomeric materials.

In another embodiment, an inlet member can be modified from the design in FIG. 32 to contain only one inlet and one outlet. In this case, the cover may have a splitter, which splits the incoming and outgoing flow into four streams. Such a design can reduce the number of connections required between the cover and the external liquid-handling system.

EXAMPLES

Apparatus Used

The apparatus used in the following Examples is composed of an immobilisation member in form of a chip as depicted in FIG. 2E and FIG. 2F and a reservoir in form of a chip holder, as shown in FIGS. 2G and 2H. The chip can be positioned in a pocket of the holder or be attached to the holder. In most experiments the chip was made of glass due to ease of surface modification and transparency. The surface of a chip has a relatively hydrophilic pattern surrounded by a hydrophobic coating. The hydrophobic coating can be formed by perfluorosilane such as heptadecafluoro-1,1,2,2-tetrahydrodecyltrimethoxysilane or alkylsilane such as octadecyltriethoxysilane. Among the silanes for hydrophobic coating, the most suitable one in this illustrative experiment was the perfluorosilane coating formed by heptadecafluoro-1,1,2,2-tetrahydrodecyltrimethoxysilane. After cleaning with Piranha solution, $V(H_2SO_4)/V(H_2O_2)=7/3$, at 110° C. for 0.5 h, the chip was rinsed with Milli-Q $H_2O$ and dried with $N_2$. Next, the glass chips were coated with $TiO_x$ at room temperature or at 500° C. using a home-made sputter via a mask with 100-2000 µm diameter through-holes (step 11 in Scheme 1FIG. 2A). This step produced patterned coatings of amorphous $TiO_x$ or a mixture of anatase-amorphous $TiO_x$ on the glass surface (Luca, D. J., *Optoelectron. Adv. Mater.* (2005) 7, 62511). The power of Ti source was 200 W. The Ar and $O_2$ gas flows rates were 25.2 and 10.8 sccm, respectively. The chamber pressure for sputtering was 2 mTorr. After removal from the sputter chamber, the $TiO_x$-coated glass chips were vapour-coated with heptadecafluoro-1,1,2,2-tetrahydrodecyl)triethoxysilane (FTES, (Gelest, Inc., Morrisville, Pa.) at 115° C. for 2 h under 1 mTorr pressure to form a hydrophobic coating (step II IV in Scheme 1 FIG. 2A; Beck, M., et al., *Microelectron. Eng.* (2002) 61-62, 441).

In order to generate hydrophilic-hydrophobic micropatterns, the FTES-coated $TiO_x$-patterned glass chip was irradiated under UV for 2 h (wavelength=254 nm, 120 mJ/cm$^2$, XL-1500 UV Crosslinker, Krackeler Scientific, Inc., Albany, N.Y.). This resulted in the exposure of fresh $TiO_x$ on the hydrophilically patterned areas with minimal impact on the hydrophobically patterned areas. The advancing contact angle changed from 119±2° to 0°, suggesting complete removal of the hydrophobic FTES coating from the surface. During UV irradiation, the difference between advancing and receding angles increased dramatically before both angles approached 0°.

Alternatively, glass slides printed with polytetrafluoroethylene (PTFE) resin were purchased from Electron Microscopy Sciences (Hatfield, Pa., USA) and Tekdon (Myakka City, Fla., USA). The slides had a pattern of uncoated, bare glasses whose diameter varies from 1.5 mm to 3 mm. In general, PTFE-printed slides were used in these illustrative experiments over in-house perfluorosilane-coated slides because PTFE exhibited better surface hydrophobicity.

The development and tests were conducted largely at two different scales—sub-microliter level for hydrophilic spots of 500 µm-diameter and 1.2 mm-diameter, and 1-5 µL for a hydrophilic spot of 2 mm-diameter. A chip patterned with 500-mm spots or 1.2-mm spots had dimensions of 37.8 mm×17.8 mm, and an array of 15×6 features (FIG. 2A). The chip was fabricated following a method described in another application. A glass slide was patterned with $TiO_x$ followed by extensive cleaning in piranha solution and exposure to a vapour of heptadecafluoro-1,1,2,2-tetrahydrodecyltrimethoxysilane at 120-150° C. for 2 hours. Upon the coating of perfluorosilane, the chip is exposed to UV irradiation for 1-2 hours followed by vigorous rinsing under running DI water to remove perfluorosilane film on $TiO_x$ patterned area. Then, $TiO_x$ film is removed by exposing the chip to 1 M KOH or NaOH solution for 10-30 seconds. The freshly exposed glass areas surrounded by perfluorosilane coating can be further modified with another silane film for facilitating biological assays performed in the areas. A chip patterned with 2-mm spots has dimensions of 75 mm×25 mm, and an array of 12×3, 12×4 or 13×5 features depending on the supplier (FIG. 2B). The hydrophobic surface of the chip exposes printed PTFE resin and hydrophilic surface exposes bare glass surface. The chip was purchased from Electron Microscopy Sciences (Hatfield, Pa., USA) and Tekdon (Myakka City, Fla., USA). In some experiments the area of a chip actually used for the respective assay was smaller than the size of the chip.

The chip holder was made of an organic, inorganic or metallic substrate such as plastic, glass, silicon, anodized aluminium or stainless steel, and had a pocket in its centre for receiving a chip. In general, a chip was made of polycarbonate, (anodized) aluminium or stainless steel. A model chip holder for the 500 mm and 1.2 mm patterned chip had dimensions of 75 mm×25 mm, and a height of 5 mm. In the centre, there was a pocket of 38 mm×18 mm (FIG. 2A). This pocket was capped with a coverslip glass at the bottom and the chip was placed on top. For the housing of commercially available 2 mm-patterned chip, the chip holder dimensions are 75 mm×25 mm×5 mm, and the pocket size is 60 mm×21 mm (FIG. 2B). The 2 mm-patterned chip, which had the same dimensions as the chip holder, was adhered to the bottom of the chip holder, with the pocket exposing those spots used for the experiments.

Liquid Handling

PFCL was used as the hydrophobic medium that is immiscible with the liquid droplet. PFCL was dispensed into the chip holder to completely cover the surface of a chip placed within the pocket thereof. 0-40% perfluorocarbon-ethylene glycol surfactants were added to the PFCL. Specifically, a series of PFCL from 3M called Fluorinert™ were used. In the tests described below, FC-70, FC-40 and FC-3283 were used solely or as a mixture. As for surfactants, 10% of $CF_3(CF_2)_6$—$CH_2CH_2OH$ or $CF_3(CF_2)_8$—$CH_2CH_2OH$ were used for selected experiments.

The method used for dispensing and controlling liquid droplets depended on the scale of the assay. For volumes of 1 μL and above, manual dispensing using a pipette or mechanical dispensing employing a pipetting mechanism was employed, as depicted in FIG. 1C. For example, Eppendorf™ pipettors were used for dispensing liquid same as or above 1 μL. For the volume of less than 1 μL, liquid was dispensed with either Eppendorf™ pipettor or submicroliter dispenser, BioJet Plus™ by Biodot, Inc (USA). A reagent solution was directly placed onto a hydrophilic spot on the surface (FIG. 4C), and/or dispensed with a certain velocity above the surface to reach and adhere to a hydrophilic spot by inertia.

For volumes smaller than 1 mL, mechanical dispensing was used as it typically provides greater ease in achieving the necessary precision in fluidics control at such scale. Usually solenoid-based or piezoelectric dispensing was employed. When dispensed, a droplet of a reagent solution was attracted to the surface of the chip against the buoyancy force of the PFCL. When the droplet came in contact with the hydrophilic spot on the surface, it got anchored by hydrophilic-hydrophilic attraction.

Attraction of Droplets Through a Layer of PFCL

For attracting a droplet down to the surface of a chip pressure dispensing was mostly employed. A liquid droplet was dispensed onto a hydrophilic area on a surface at a speed sufficient to penetrate the PFCL layer and adhere to the hydrophilic area. In this configuration, the kinetic energy of the droplet is greater than the resistance of the immiscible liquid. In order to assist in the positioning of each dispensed drop, a Teflon chip was placed on top of the patterned chip ("3" in FIG. 4E).

In some experiments a high-voltage ionizer was employed in order to charge a droplet on the PFCL, and to move it down to the chip by electrostatic repulsion. A chip holder is placed on a flat ground electrode, a glass wafer coated with a thin film of Cr and Au sequentially by e-beam evaporation, where the film of Au functions as an electrode, and a high-voltage ionizer, Pulse Flow Controller™ with V-block ionizer by SIMCO is positioned above the chip. A droplet was charged either by a positive or a negative charge from the ionizer, and moved away from the ionizer by electrostatic repulsion. A ground electrode below the chip holder was generally used to help such downward movement of the droplet. Once a droplet moves down using this method, the entire system of chip and chip holder including the dispensed droplets is neutralized by a flow of positive and negative charges (FIG. 4G).

Assay Procedure

In a typical process of liquid handling, an immiscible liquid was added to cover the surface of a chip before or after the first dispensing, depending on the volume and evaporation rate of the dispensed drops. Once all the sample liquids were dispensed, they were incubated under a desired condition for a desired time period. Upon completion of the incubation, the sample was either read directly or after undergoing a series of processing before the signals were read. The representative processing steps applicable to a wide range of assays are presented below.

Addition of a New Solution After Removing an Existing Solution

FIG. 6 shows a general scheme for the rinsing of an existing sample and the addition of a new sample. PFCL was drained away by holding a chip and chip holder at an angle or taking a chip away from a chip holder and holding the chip at an angle. In some cases the PFCL used for incubation was highly viscous, so that it was replaced with PFCL of a lower viscosity by either adding low-viscosity PFCL onto the chip or rinsing the chip/chip holder in low-viscosity PFCL after draining an existing liquid. Once low-viscosity PFCL was drained from the surface of the chip, the chip (with or without chip holder) was immersed in a rinsing solution and shaken for 5-300 sec. as little PFCL as possible was used without drying up and exposing a naked chip surface. A dried and exposed chip surface can cause wetting of the dried area and destroying the pattern of isolated hydrophilic spots. Too much PFCL on the surface can inhibit free mixing of drops with a rinsing solution. With the right amount of PFCL left on the surface and appropriate viscosity (which can be easily determined by experiment), the drops can readily mix with a rinsing solution while the hydrophobic surface remains separated from the rinsing solution by a layer of PFCL.

In this regard it is noted that other embodiments than that of the present example have also been tested. In such embodiments a chip is processed without being attached to a chip holder. During incubation, a chip is immersed in PFCL in a Petri dish to avoid evaporation. During rinsing, the chip is then placed in a tube filled with a rinsing solution.

When rinsing was completed and the chip was removed from the solution, the hydrophilic areas were left with only a little amount of the rinsing solution, forming a thin layer. The amount of rinsing solution left to cover the hydrophilic area was negligible and comparable to the corresponding case in a multiwell plate. It is noted that if necessary, a chip can be exposed to a rinsing solution for an extended time without any wetting of the hydrophobic area, due to the presence of a thin PFCL layer. Such capability can be useful when the entire array of the chip needs to be incubated in a certain solution for an extended time. Before proceeding with the addition of a new solution, a chip was generally immersed in a PFCL to avoid any evaporation.

Following the same protocol, rinsing was usually performed repeatedly. In addition to the steps described above, addition of a solution to form a drop was necessary before secondary rinsing. This was to ensure that each hydrophilic area got well into contact with a rinsing solution. Without the addition step, the hydrophilic areas were so thin after the first rinse, some of the spots could be hidden below a thin layer of PFCL without mixing with a secondary rinsing solution.

Signal Detection

For most biological applications, optical detection is currently the preferred method used in the art for analyzing the reaction occurring in the droplets. Accordingly, the same method was employed in the present example of the invention. A chip holder was positioned on an inverted fluorescence microscope Fluoview IX 71 FV5-PSV (Olympus, Japan) or the microscope "Insight 3D Cell" (Evotec Technologies, Hamburg, Germany), an advanced inverted confocal fluorescence microscope. The signal within the drops could be examined from below.

Growth and Test of Cell Viability of NIH3T3 Cells (a) Creation of Cell Friendly Surface Fetal Bovine Serum (FBS) was spotted onto a Teflon or Teflon-coated chip followed by heating on a hotplate at 200° C. for 2 hours and UV irradiation for 30 minutes. This process generates hydrophilic 'sticky' protein film on a Teflon surface.

(b) Cell Preparation and Seeding

Confluent NIH3T3 cells growing in a tetraphenylporphyrin (TPP) tissue culture flask with a surface area of 75 cm$^2$ and a filtered cap (known as "T75 flask" to those skilled in the art) were rinsed twice with phosphate buffered saline. Thereafter, 1 mL of 0.25% trypsin and 0.2 g/l EDTA was applied to detach the cells. After cell detachment, trypsin was neutralized by the addition of 9 mL of DMEM medium (containing 10% Fetal Bovine Serum and 1% penicillin/streptomycin). Subsequently, the cells were counted using a haemocytometer, pelleted by centrifugation at 800 rpm for 5 minutes, and resuspended at a concentration of approximately 100 cells/µl in DMEM medium (containing 10% FBS and 1% penicillin/streptomycin).

(c) Cell Dispensing

Cells were dispensed onto the cell friendly surface using a piezodispenser, SciflexArrayer, from Scienion in Berlin, Germany.

(d) Cell Growth and Live/Dead Cell Assay

After cell seeding, the chip was covered with PFCL and placed in a cell culture incubator (37° C., 5% $CO_2$).

Cells were allowed to grow for 3 days on the chip. After 3 days, cell viability was performed using the Live/Dead cell assay kit from Molecular Probes (Invitrogen). Calcein AM and ethidium homodimer-1 were added to the cell drop to a final concentration of 2 uM. Live and dead cells were viewed using an Olympus IX71 microscope under illumination from a mercury lamp with the aid of the appropriate filters (blue fluorescent cube for live cells and green fluorescent cube for dead cells).

Cell-Staining Assay (a) Preparation

Cell-based assays can be performed at 20 nL-10 µL, depending on the size of hydrophilic patterns on the surface. In the present example a cell-based assay was run at 0.8 µL with a glass slide patterned with 1.2-mm hydrophilic features.

Before each experiment, all tools to be used were thoroughly cleaned and sterilized. Grease and other organic deposits were removed from the Teflon chip by soaking them in RBS 50 concentrate for 1 h, followed by rinsing with running water. The chip was then autoclaved at 105° C. for 30 min. Selective patterned chips were maintained clean throughout the manufacturing process; they were only rinsed in 100% ethanol, blown dry and UV sterilized. Chip holders were cleaned in isopropanol to remove residual debris; they were subjected to 25 kGy dose of gamma irradiation for sterilization.

Water-saturated PFCL was prepared by autoclaving 900 ml of PFCL with 50 ml of water in a bottle (1 liter) at 105° C. for 30 min. After autoclaving, it was filtered through a 0.2-µm filter.

(b) Comparison of Cell Growth on Patterned Slide and on 60-mm Dish

HepG2 cells were transfected with, a green fluorescent protein (GFP), maxGFP™, using Nucleofactor Kit V from Amaxa (Cologne, Germany). Cells were chemically selected for stable transgene integration with G418. Stably transfected HepG2-maxGFP cells were seeded on the hydrophilic areas. The drops were covered with PFCL and the whole slide was placed in a cell culture incubator (37° C., 5% $CO_2$). For comparison, the same cell volumes were seeded on a PFCL-covered 60-mm tissue culture treated Petri dish. The dish was left in a cell culture incubator for 30 min to allow the cells to adhere. PFCL was then removed and replaced with 5 mL of cell culture medium (DMEM containing 1000 mg/L glucose, 10% fetal bovine serum (FBS), 1% penicillin/streptomycin). The number of cells growing on the dish and on the patterned slide was counted every day using an inverted fluorescent microscope.

Figure 10:
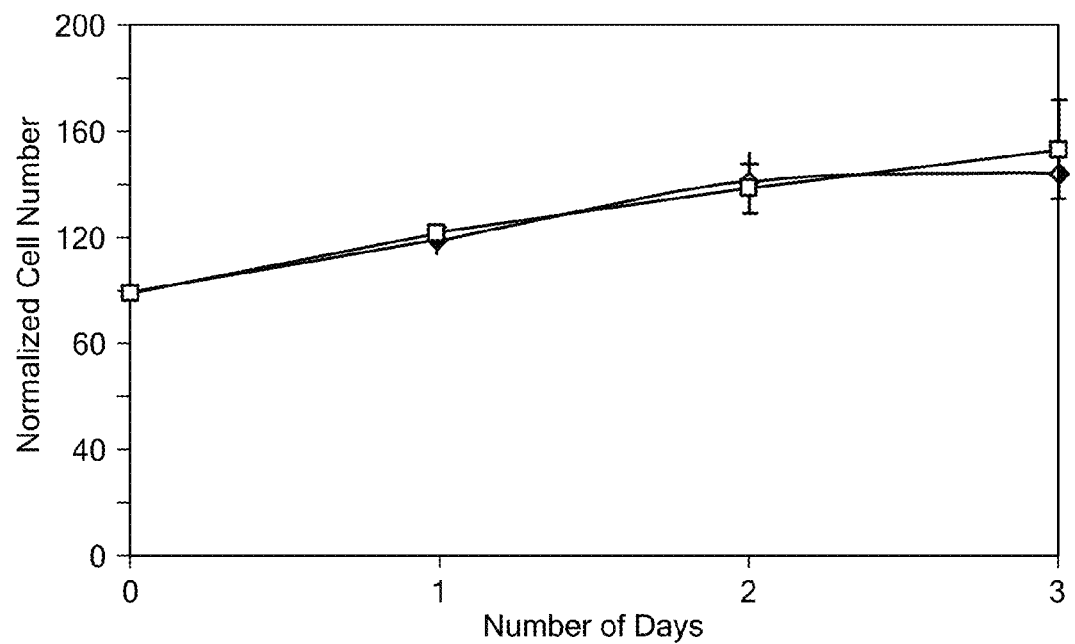
FIG. 10 shows a comparison of cell growth on a patterned immobilisation member (♦) in a volume of 0.8 ml and on a 60-mm dish in a volume of 5 ml (■).

Cells demonstrated very similar pattern of proliferation as a drop on the patterned slide and in bulk cell culture medium on a 60-mm tissue culture treated dish over a 3-day monitoring period (FIG. 10).

Immunofluorescence Staining of Cells Growing in a Droplet maxGFP™-transduced HepG2 cells were grown in drops on a patterned slide covered with PFCL (FIG. 11A). To begin staining, cell culture medium (DMEM containing 1000 mg/L glucose, 10% fetal bovine serum (FBS), 1% penicillin/streptomycin) in the drops was removed by rinsing with phosphate buffered saline (PBS) in a rinsing chamber. The cells were then fixed using 3.7% formaldehyde for 2 min or ice-cold ethanol for 1 min. To permeablize the cells, 0.1% Triton X in PBS was used. Next, the cells were blocked in 1% bovine serum albumin (BSA), 10% FBS in PBS for 5 min. This was followed by incubation of the cells with 0.8 µL of a rabbit anti-Ki67 polyclonal antibody for 15 min, and then rinsing in a rinsing chamber with PBS containing 0.1% Tween 20 three times for 10 sec each. Between rinsing steps, 0.8 µL of PBS was dispensed onto the "cell growth areas" to allow more effective mixing during rinsing in the rinsing chamber. Next, the cells were incubated for 10 min with 0.8 µL of a goat anti-rabbit IgG secondary antibody conjugated with the Alexa 633 dye (Molecular Probes). The patterned slide was then placed again into the rinsing chamber containing PBS with 0.1% Tween 20, and rinsed three times for 10 sec each. Fluorescently labelled cells were visualized on a fluorescent microscope.

The cell-staining assay was completed in just 30 min compared to over 2 h on wells of a 96-well plate. The rinsing method allowed multiple "cell growth areas" on the patterned slide to be rinsed in parallel, resulting in more even, efficient and rapid rinsing. The miniaturized format resulted in at least about 10 to 20-fold savings in the amount of antibodies required (1000-fold savings when staining was performed in a volume of 50-100 mL). The fluorescently stained cells are shown in FIG. 11B. The cells growing on the patterned slide expressed the cell proliferation marker Ki67, demonstrating further that they could proliferate in a small drop.

Rat IgG ELISA (a) Effective Rinsing and Addition at 50-nL Volume

A simple test with two different dyes, rhodamine 110 and fluorescein, was run to validate effective rinsing and addition in a microarray format. A glass chip was patterned to produce 500-mm hydrophilic spots surrounded by a hydrophobic perfluorosilane coating on the surface. The chip was attached to a chip holder to expose an area of array through a pocket in the middle. Dispensing of rhodamine 110 solution in PBS was performed following the addition of a PFCL to cover the surface. The dispensed chip was tilted perpendicular to the ground in order to drain the PFCL. The chip was then rinsed under a continuous stream of PBS buffer. Fluorescein solution was then dispensed following the addition of PFCL to cover the chip surface.

Fluorescent images of the chip after each dispensing and rinsing show the effectiveness of this novel rinsing method (FIG. 12). Upon rinsing of the rhodamine solution, the fluorescence from the hydrophilic area was as low as the background, suggesting that a negligible amount of dye was left at each hydrophilic area. Upon dispensing of a fluorescein solution, the fluorescence from the solution was identical to that of the bulk solution prior to dispensing. This suggested that the dilution of fluorescein solution by the solution left at the hydrophilic area from previous dispensing and/or rinsing solution was minimal. Furthermore, there was no wetting of hydrophobic surface, based on the same pattern of hydrophilic spots obtained.

(b) Rat IgG ELISA in a 96-Well Microtiter Plate

For a comparison, the assay in 96-well multiwell plate was run following the standard protocol of the ELISA quantitation kit, except that secAb-HRP (horse radish peroxidase) and TMB peroxidase were replaced with secAb-AP and FDP, respectively.

FIG. 13A shows a graph of a reference ELISA run in a Greiner's black 96-well microtiter plate at 100 mL following a standard protocol. The fluorescence signal from the assay increased with increasing concentration of rat serum. The assay could detect as low as 1.95 ng/mL of serum.

(c) Rat IgG ELISA on a Microscope Slide Patterned with 2-mm Hydrophilic Areas

ELISA assays can for example be performed at 20 nL-10 mL depending on the size of the hydrophilic patterns on the hydrophobic surface of the immobilisation member. In the present example an ELISA was performed at 3-6 mL with a glass slide patterned with 2-mm hydrophilic features.

All the reagents except for the secondary antibody conjugated with alkaline phosphatase (secAb-AP) and fluorescein diphosphate (FDP) were prepared following a standard protocol provided by the supplier of the ELISA quantitation kit (Bethyl Laboratories Inc., Montgomery, catalog-No. E110-128). The secAb-AP conjugate was prepared by diluting the stock solution of 0.1 mg/mL secAb-AP to the sample diluent containing 50 mM Tris, 0.14 M NaCl, 1% BSA, 0.05% Tween 20, pH 8.0, at a ratio of 1:500. FDP solution was prepared at 10 mM in the washing buffer containing 50 mM Tris, 0.14 M NaCl, 0.05% Tween 20, pH 8.0. A microscope glass slide with a pattern of 2-mm hydrophilic features is attached to a chip holder to expose the array area in the pocket.

The assay on a patterned glass slide with 2-mm features was run following a modified procedure. The primary antibody solution was dispensed to each hydrophilic area at 3 mL, followed by the addition of a PFCL (usually FC-3283) to cover the droplet sufficiently. The chip holder was capped with a microscope glass slide during incubation for 30 min. The chip/chip holder was inserted in a 50-mL falcon tube containing 45 mL of washing buffer. The tube was shaken for 30 sec at 90 rpm on a linear motion shaker. Upon completion of the rinse, the chip/chip holder was removed from the tube, and a PFCL is added to the chip to cover the surface. Postcoating solution was added to each well at 4 mL, and a PFCL was added to cover the dispensed drops completely. Subsequent rinsing and addition were performed in the same manner with 30 min of incubation at each step. A series of rat serum solutions was prepared, and dispensed onto a hydrophilic area in duplicates at 3 mL: 0 ng/mL, 0.46 ng/mL, 1.85 ng/mL, 7.8 ng/mL, 15.625 ng/mL, 31.25 ng/mL, 62.5 ng/mL, and 500 ng/mL. Both secAb-AP and FDP solution were dispensed onto each spot at 3 mL. Notably, the chip was rinsed twice before the addition of FDP solution. In this rinsing step, 3 mL of washing buffer was dispensed onto every hydrophilic area between the first and second rinsing. As a final step, 3 mL of FDP solution was added to each hydrophilic area, and the chip was placed in Evotec's Insight confocal reader after wiping the bottom side of the chip. The fluorescence from fluorescein produced by the reaction between FDP in solution and surface-immobilised secAb-AP was measured.

FIG. 13B shows a graph of an ELISA run on a chip patterned with 2-mm hydrophilic features at 3-4 mL. Similar to the assay in a microtiter plate, the fluorescence signal from the assay increased with increasing concentration of serum. However, the sensitivity of the assay had improved such that 0.46 ng/mL of serum could be detected. It is understood that the ELISA assay has not been optimised for the method of the invention, so that the depicted results may not reveal the entire potential of the method of the present invention. A lower consumption of reagents and a higher detection sensitivity, which is currently under further investigation, were nevertheless unequivocally apparent. In addition, the incubation time required for an assay at 3-4 mL was shortened to at least half of the time required for a conventional bulk assay. The duration of an assay was expected to decrease with decreasing assay volume; this is currently being investigated.

Affinity Purification of a Protein (Green Fluorescent Protein)

This example illustrates how a protein can be purified using the method of the present invention. A biochip as described above can be used as the immobilisation member of the apparatus of the invention.

An aqueous liquid droplet of 1 µl containing 50 mM Tris-HCl pH 7.7, 200 mM NaCl, 5 mM EDTA and Streptavidin-modified magnetic agarose beads (QIAGEN, equivalent to a 4% (w/v) suspension) can be prepared after washing the tagged agarose beads with 0.01 M phosphate-buffered saline (PBS). Ultrafiltrated mineral oil (Fluka) can be used as the immiscible medium that is filled into the reservoir as described above. A droplet containing 1 µl of a crude bacterial lysate (*E. coli*) containing biotinylated recombinant green fluorescent protein (GFP) in above buffer (50 mM Tris-HCl pH 7.7, 200 mM NaCl, 5 mM EDTA) can be added (see e.g. FIG. 4B) and merged with the droplet containing the magnetic agarose beads. The obtained droplet can be incubated at room temperature for 45 min. Thereafter, the immobilisation member is removed from the reservoir of the apparatus and a magnet is placed behind it, i.e. on the side of the immobilisation member that opposes the side of the hydrophobic surface that is patterned to include hydrophilic areas. The droplet can then be washed successively by rinsing three times with the above buffer (50 mM Tris-HCl pH 7.7, 200 mM NaCl, 5 mM EDTA) as described above and depicted in FIG. 6. Elution of the purified GFP in a droplet can be performed by replenishing the liquid droplet on the respective hydrophilic area (cf. above) with 25 µl containing 10 mM biotin in above buffer, and mixing by exposure to ultrasound. Thereafter the magnetic agarose beads can be removed by changing the position of the magnet that is placed behind the immobilisation member and subsequently removing the magnet while still attracting the magnetic beads. Quantification may be performed by any standard method such as the ratio of UV absorption at 280 and 260 nm according to Layne, by performing a colour reaction in a reference droplet, for example according to Bradford, separation by SDS-polyacrylamide-gel-electrophoresis and a subsequent stain, or by fluorescence detection using a reference solution of GFP of known concentration.

The listing or discussion of a previously published document in this specification should not necessarily be taken as an acknowledgment that the document is part of the state of the art or is common general knowledge. All documents listed, whether explicitly incorporated herein upon their citation or not, are hereby incorporated herein by reference in their entirety for all purposes.

The inventions illustratively described herein may suitably be practiced in the absence of any element or elements, limitation or limitations, not specifically disclosed herein. Thus, for example, the terms "comprising", "including," containing", etc. shall be read expansively and without limitation, and are not limited to only the listed components they directly reference, but include also other non-specified components or elements. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. An apparatus for processing a biological and/or chemical sample in a liquid droplet, the apparatus comprising a processing compartment and a medium disposed in said processing compartment, wherein said processing compartment is defined by a reservoir and an immobilisation member, wherein said medium is (i) immiscible with said liquid droplet, and (ii) of a lower surface energy than the liquid of the liquid droplet; wherein said reservoir is defined by a circumferential wall and a base, and wherein said immobilisation member is (i) arranged within said reservoir, and (ii) comprises a surface, wherein the surface is patterned in such a way that it comprises at least one predefined immobilisation area, wherein (a) the at least one predefined immobilisation area within said surface is (i) of a higher surface energy than said medium, (ii) of a higher surface energy than the remaining surface, and (iii) of a sufficient surface energy and a sufficient width in the plane of the surface to allow, in said medium, the immobilisation of the liquid droplet on the at least one predefined immobilisation area via interfacial interactions, and (b) the remaining surface is of at most the same surface energy as said medium.

2. The apparatus of claim 1, wherein said remaining surface of the immobilisation member is of a lower surface energy than the liquid of the liquid droplet.

3. The apparatus of claim 1, wherein said predefined immobilisation area within said patterned surface is characterised by an advancing contact angle for water that is at least 5° lower than the advancing contact angle for water of the remaining surface.

4. The apparatus of claim 1, wherein said predefined immobilisation area within said patterned surface is characterised by an advancing contact angle for water that is at least 5° lower than the advancing contact angle for water of the said medium.

5. The apparatus of claim 1, wherein the liquid of said liquid droplet is hydrophilic.

6. The apparatus of claim 1, wherein said medium, which is of lower surface energy than the liquid of the liquid droplet, is hydrophobic.

7. The apparatus of claim 1, wherein said interfacial interactions allowing the immobilisation of the liquid droplet are at least one of hydrophilic-hydrophilic, hydrophobic-hydrophobic, oleophilic-oleophilic and perfluorophobic-perfluorophobic.

8. The apparatus of claim 1, wherein said interfacial interactions allowing the immobilisation of the liquid droplet are attraction forces.

9. The apparatus of claim 1, wherein the medium comprises a hydrophobic medium, wherein said hydrophobic medium is (i) immiscible with said liquid droplet, and (ii) of higher hydrophobicity than the liquid of the liquid droplet; wherein said reservoir is defined by a circumferential wall and a base, and wherein said immobilisation member is (i) arranged within said reservoir, and (ii) comprises a hydrophobic surface, the hydrophobic surface being patterned in such a way that it comprises at least one predefined hydrophilic immobilisation area, wherein (a) the at least one predefined hydrophilic immobilisation area within said hydrophobic surface is of a sufficient wettability and a sufficient width in the plane of the surface to allow, in said hydrophobic medium, the immobilisation of the liquid droplet on the predefined hydrophilic immobilisation area via hydrophilic-hydrophilic interactions, and (b) the remaining hydrophobic surface is of at least the same hydrophobicity as said hydrophobic medium.

10. The apparatus of claim 1, wherein said predefined immobilisation area is of such a high wettability for the liquid of the liquid droplet and of such a width in the plane of the surface of the immobilisation member that the maximal force, which said interfacial interactions are capable of exerting on said droplet in said medium, is higher than the buoyancy force.

11. The apparatus of claim 10, wherein said predefined immobilisation area is of such a high wettability for the liquid of the liquid droplet and of such a width in the plane of the surface of the immobilisation member that the maximal force, which said interfacial interactions are capable of exerting on said droplet in said medium, is higher than the Bernoulli force (flow force) exerted by said medium upon moving said immobilisation member or said apparatus.

12. The apparatus of claim 1, wherein said predefined immobilisation area is of such a high wettability for the liquid of the liquid droplet and of such a width in the plane of the surface of the immobilisation member that the maximal force, which said interfacial interactions are capable of exerting on said droplet in said medium, is higher than the force exerted by said medium upon rinsing said immobilisation member therewith.

13. The apparatus of claim 1, wherein said predefined immobilisation area is designed to allow the immobilisation of target matter that is suspected to be comprised in said biological and/or chemical sample.

14. The apparatus of claim 1, wherein the immobilisation member is removably arranged within the apparatus.

15. The apparatus of claim 1, further comprising an upper inlet on top of the reservoir of the processing compartment, wherein the upper inlet is capable of providing a fluid communication between the processing compartment and the environment of the apparatus.

16. The apparatus of claim 15, wherein the upper inlet is an opening of a size sufficient to allow the insertion and/or removal of said immobilisation member.

17. The apparatus of claim 1, wherein said surface of the immobilisation member, including both the predefined immobilisation area of a higher surface energy than the remaining surface and the remaining surface that has at most about the same surface energy as said medium, is at least essentially flat.

18. The apparatus of claim 1, wherein the immobilisation member is selected from the group consisting of a plate, a brick and a disk.

19. The apparatus of claim 1, wherein the immobilisation member comprises a material selected from the group consisting of plastic, glass, quartz, silicon, metal and composites thereof.

20. The apparatus of claim 1, wherein the surface of the immobilisation member comprises a plurality of predefined immobilisation areas.

21. The apparatus of claim 1, wherein the circumferential wall of the reservoir is adapted to support the immobilisation member.

22. The apparatus of claim 21, wherein the circumferential wall comprises a support dent, a reception recess or a step, wherein said step is defined by an extension of the circumferential wall into the interior of the reservoir.

23. The apparatus of claim 1, further comprising an electrode that is capable of providing an electric field.

24. The apparatus of claim 23, wherein said electrode is comprised in the base of the reservoir.

25. The apparatus of claim 1, wherein the inner wall surface has a surface energy of at most 24 dynes/cm.

26. The apparatus of claim 1, wherein the inner wall surface has a surface energy of at most 18 dynes/cm.

27. The apparatus of claim 1, wherein the inner wall surface has a surface energy of less than 72 dynes/cm.

28. The apparatus of claim 1, wherein the remaining surface is formed by a perfluorocarbon-containing coating.

29. The apparatus of claim 1, wherein the at least one predefined immobilisation area is covered by the medium.

* * * * *